United States Patent
Jia et al.

(10) Patent No.: US 11,104,682 B2
(45) Date of Patent: Aug. 31, 2021

(54) SALTS OF TAM INHIBITORS

(71) Applicant: Incyte Corporation, Wilmington, DE (US)

(72) Inventors: Zhongjiang Jia, Kennett Square, PA (US); Yongzhong Wu, Glen Mills, PA (US); Yongchun Pan, Wilmington, DE (US); Jiacheng Zhou, Newark, DE (US); Qun Li, Newark, DE (US)

(73) Assignee: Incyte Corporation, Wilmington, DE (US)

(*) Notice: Subject to any disclaimer, the term of this patent is extended or adjusted under 35 U.S.C. 154(b) by 0 days.

(21) Appl. No.: 16/823,751

(22) Filed: Mar. 19, 2020

(65) Prior Publication Data
US 2020/0347065 A1 Nov. 5, 2020

Related U.S. Application Data

(62) Division of application No. 16/142,514, filed on Sep. 26, 2018, now Pat. No. 10,633,387.

(60) Provisional application No. 62/714,196, filed on Aug. 3, 2018, provisional application No. 62/564,070, filed on Sep. 27, 2017.

(51) Int. Cl.
*C07D 487/04* (2006.01)
*A61P 35/00* (2006.01)

(52) U.S. Cl.
CPC ............ *C07D 487/04* (2013.01); *A61P 35/00* (2018.01); *C07B 2200/13* (2013.01)

(58) Field of Classification Search
CPC .............................. C07D 487/04; A61K 31/53
USPC .......................................... 544/183; 514/243
See application file for complete search history.

(56) References Cited

U.S. PATENT DOCUMENTS

| | | | |
|---|---|---|---|
| 9,708,333 B2 | 7/2017 | Li et al. | |
| 9,840,503 B2 | 12/2017 | Sun et al. | |
| 9,981,975 B2 * | 5/2018 | Li | C07D 487/04 |
| 10,053,465 B2 | 8/2018 | Li et al. | |
| 10,138,248 B2 | 11/2018 | Buesking et al. | |
| 10,442,810 B2 * | 10/2019 | Li | A61K 31/53 |
| 10,633,387 B2 * | 4/2020 | Jia | A61P 35/00 |
| 10,844,069 B2 | 11/2020 | Li et al. | |
| 2010/0298334 A1 | 11/2010 | Rodgers et al. | |
| 2011/0015212 A1 | 1/2011 | Li et al. | |
| 2011/0059951 A1 | 3/2011 | Rodgers et al. | |
| 2011/0183985 A1 | 7/2011 | Li et al. | |
| 2011/0224190 A1 | 9/2011 | Huang et al. | |
| 2012/0015937 A1 | 1/2012 | Ding et al. | |
| 2012/0088768 A1 | 4/2012 | Singh et al. | |
| 2012/0149681 A1 | 6/2012 | Rodgers et al. | |
| 2012/0149682 A1 | 6/2012 | Rodgers et al. | |
| 2012/0157430 A1 | 6/2012 | Li et al. | |
| 2012/0184535 A1 | 7/2012 | Brzozka et al. | |
| 2012/0219522 A1 | 8/2012 | Xi | |
| 2012/0230993 A1 | 9/2012 | Graham et al. | |
| 2012/0264740 A1 | 10/2012 | Goff et al. | |
| 2012/0283261 A1 | 11/2012 | Bearss et al. | |
| 2013/0018034 A1 | 1/2013 | Yao et al. | |
| 2013/0018051 A1 | 1/2013 | Singh et al. | |
| 2013/0045963 A1 | 2/2013 | Rodgers et al. | |
| 2013/0059835 A1 | 3/2013 | Li et al. | |
| 2013/0090330 A1 | 4/2013 | Ding et al. | |
| 2013/0197070 A1 | 8/2013 | De Franciscis et al. | |
| 2013/0281468 A1 | 10/2013 | Goff et al. | |
| 2014/0005166 A1 | 1/2014 | Rodgers et al. | |
| 2014/0018365 A1 | 1/2014 | Schultz-Fademrecht et al. | |
| 2014/0121198 A1 | 5/2014 | Li et al. | |
| 2014/0128390 A1 | 5/2014 | Lin | |
| 2014/0128400 A1 | 5/2014 | Singh et al. | |
| 2014/0275023 A1 | 9/2014 | Namdev et al. | |
| 2016/0333008 A1 | 11/2016 | Sun et al. | |
| 2017/0044164 A1 | 2/2017 | Li et al. | |
| 2017/0057965 A1 | 3/2017 | Li et al. | |
| 2017/0275290 A1 | 9/2017 | Li et al. | |
| 2018/0009815 A1 | 1/2018 | Li et al. | |
| 2018/0327412 A1 | 11/2018 | Li et al. | |
| 2019/0031663 A1 | 1/2019 | Li et al. | |
| 2019/0112313 A1 | 4/2019 | Jia et al. | |
| 2020/0000812 A1 | 1/2020 | Rocco et al. | |
| 2020/0131185 A1 | 4/2020 | Li et al. | |
| 2020/0181151 A1 | 6/2020 | Li et al. | |

FOREIGN PATENT DOCUMENTS

| | | |
|---|---|---|
| CL | 2018000949 | 12/2018 |
| CL | 2019000043 | 6/2019 |
| CL | 2019000115 | 6/2019 |
| CN | 101084218 | 12/2007 |
| CN | 102408411 | 4/2012 |
| CN | 102918045 | 2/2013 |

(Continued)

OTHER PUBLICATIONS

Affouard et al., "Multi-Kilo Delivery of AMG 925 Featuring a Buchwald-Hartwig Amination and Processing with Insoluble Synthetic Intermediates," Organic Process Research & Development, 2015, 19: 476-485.

(Continued)

*Primary Examiner* — Paul V Ward
(74) *Attorney, Agent, or Firm* — Fish & Richardson P.C.

(57) ABSTRACT

The present application provides salt forms of N-(4-(4-Amino-7-(1-isobutyrylpiperidin-4-yl)pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide and N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide, which are useful as inhibitors of TAM kinases, as well as processes and intermediates related thereto.

35 Claims, 34 Drawing Sheets
Specification includes a Sequence Listing.

(56) References Cited

FOREIGN PATENT DOCUMENTS

| | | |
|---|---|---|
| CN | 103124729 | 5/2013 |
| CN | 105732634 | 7/2016 |
| EP | 2465505 | 6/2012 |
| EP | 2484679 | 8/2012 |
| EP | 2552922 | 2/2013 |
| JP | 2008-501703 | 1/2008 |
| JP | 2009-518303 | 5/2009 |
| JP | 2009-519222 | 5/2009 |
| JP | 2009-519905 | 5/2009 |
| JP | 2012-525400 | 10/2012 |
| JP | 2014-525902 | 10/2014 |
| JP | 2015-532287 | 11/2015 |
| WO | WO 2001/019828 | 3/2001 |
| WO | WO 2002/000196 | 1/2002 |
| WO | WO 2004/035580 | 4/2004 |
| WO | WO 2005/025515 | 3/2005 |
| WO | WO 2006/046023 | 5/2006 |
| WO | WO 2007/061737 | 5/2007 |
| WO | WO 2007/070514 | 6/2007 |
| WO | WO 2007/120752 | 10/2007 |
| WO | WO 2007/125315 | 11/2007 |
| WO | WO 2008/076392 | 6/2008 |
| WO | WO 2009/023269 | 2/2009 |
| WO | WO 2009/047514 | 4/2009 |
| WO | WO 2009/053737 | 4/2009 |
| WO | WO 2009/054864 | 4/2009 |
| WO | WO 2009/085185 | 7/2009 |
| WO | WO 2009/087225 | 7/2009 |
| WO | WO 2009/127417 | 10/2009 |
| WO | WO 2010/005876 | 1/2010 |
| WO | WO 2010/005879 | 1/2010 |
| WO | WO 2010/008454 | 1/2010 |
| WO | WO 2010/014755 | 2/2010 |
| WO | WO 2010/025073 | 3/2010 |
| WO | WO 2010/071885 | 6/2010 |
| WO | WO 2010/090764 | 8/2010 |
| WO | WO 2011/038185 | 3/2011 |
| WO | WO 2011/045084 | 4/2011 |
| WO | WO 2011/139273 | 11/2011 |
| WO | WO 2012/028332 | 3/2012 |
| WO | WO 2012/048129 | 4/2012 |
| WO | WO 2012/129344 | 9/2012 |
| WO | WO 2012/135800 | 10/2012 |
| WO | WO 2013/052417 | 4/2013 |
| WO | WO 2013/074633 | 5/2013 |
| WO | WO 2013/085802 | 6/2013 |
| WO | WO 2013/115280 | 8/2013 |
| WO | WO 2013/162061 | 10/2013 |
| WO | WO 2014/062774 | 4/2014 |
| WO | WO 2014/079545 | 5/2014 |
| WO | WO 2014/109858 | 7/2014 |
| WO | WO 2014/164729 | 10/2014 |
| WO | WO 2015/012298 | 1/2015 |
| WO | WO 2015/068767 | 5/2015 |
| WO | WO 2015/132799 | 9/2015 |
| WO | WO 2016/097918 | 6/2016 |
| WO | WO 2016/183071 | 11/2016 |
| WO | WO 2017/027717 | 2/2017 |
| WO | WO 2017/062797 | 4/2017 |
| WO | WO 2017/083788 | 5/2017 |
| WO | WO 2017/083789 | 5/2017 |
| WO | WO 2017/172596 | 10/2017 |
| WO | WO 2017/184934 | 10/2017 |
| WO | WO 2019/067594 | 4/2019 |

OTHER PUBLICATIONS

Angelillo-Scherrer et al., "Role of Gas6 in erythropoiesis and anemia in mice," J. Clin. Invest., 2008, 118: 583-596.
Ash and Ash, "Handbook of Pharmaceutical Additives," Gower Publishing Company, 2007, 3rd Edition, 1 page, Title Page.
Australian Office Action in Australian Application No. 2017241524, dated Jun. 26, 2020, 4 pages.
Avilla et al., "Activation of TYRO3/AXL tyrosine kinase receptors in thyroid cancer," Cancer Res., Mar. 1, 2011, 71(5):1792-1804.
Badaway et al., "Salt Selection for Pharmaceutical Compounds," Preformulation in Solid Dosage Form Development(Informa Healthcare), 2008, Chapter 2.3, 63-80.
Baladi et al., "State-of-the-art of small molecule inhibitors of the TAM family: The point of view of the chemist," European Journal of Medicinal Chemistry, Oct. 2015, 105: 220-237.
Balupuri et al., "Molecular modeling study on Mer kinase inhibitors using 3D-QSAR and docking approaches," Medicinal Chemistry Research, Jul. 2015, 24(10): 3730-3742.
Bastin et al., "Salt Selection and Optimization Procedures for Pharmaceutical New Chemicalls Entities," Organic Process Research & Development, 2000, 4(5):427-435.
Ben-Batalla et al., "Axl Blockade by BGB324 Inhibits BCR-ABL Tyrosine Kinase Inhibitor-Sensitive and -Resistant Chronic Myeloid Leukemia," Clinical Cancer Research, May 1, 2017, 23(9):2289-2300.
Ben-Batalla., "Axl, a prognostic and therapeutic target in acute myeloid leukemia mediates paracrine crosstalk of leukemia cells with bone marrow stroma," Blood, Oct. 3, 2013, 122(14):2443-2452.
Berge, "Pharmaceutical Salts," Journal of Pharmaceutical Science, 1997, 66(1):1-19.
Blom et al., "Optimizing Preparative LC/MS Configurations and Methods for Parallel Synthesis Purification," J. Comb. Chem., 2003, 5: 670-683.
Blom et al., "Preparative LC-MS Purification: Improved Compound-Specific Method Optimization," J. Comb. Chem., 2004, 6: 874-883.
Blom, "Two-Pump at-Column-Dilution Configuration for Preparative Liquid Chromatography-Mass Spectrometry," J. Comb. Chem., 2002, 4: 295-301.
Borovik et al., "Pyrimidines. XLIX. Synthesis of 9-phenylpyrimido [4,5-b] indoles," Izvestiya Sibirskogo Otdeleniya Akademii Nauk SSSR, Seriya Khimicheskikh Nauk 1975, 137-41 (English abstract only).
Borovik et al., "Synthesis of 2-substituted pyrimido[4,5-b]indoles and N-phenyl-2,2-diethoxy-3- arylideneindolines," v sb., Khimiya i Farmakol. Indol'n. Soedinenii, 1975, 50 (English abstract only).
Brunton et al., "Chemotherapy of Neoplastic Diseases," Goodman & Gilman's. The Pharmacological Basis of Therapeutics, 2008, pp. 853-908.
Burbridge et al., "S49076 is a Novel Kinase Inhibitor of MET, AXL, and FGFR with Strong Preclinical Activity Alone and in Association with Bevacizumab," AACR Journals, 2013, 1749-1762.
Cecil Textbook of Medicine, edited by Bennet, J.C., and Plum F., 20th edition, vol. 1, 1004-1010, 1996.
Chambers et al., "Lymphoproliferation in CTLA-4-deficient mice is mediated by costimulation-dependent activation of CD4+ T cells," Immunity, Dec. 1997, 7(6): 885-95.
Chow et al., "Engineered of Pharmaceutical Materials: an Industrial Perspective," J Pharmaceutical Sciences., Aug. 2008, 97(8):2855-2877.
Chung et al., "Synthesis of certain [6:5:6] linear tricyclic nucleosides as potential antitumor agents," Journal of Medicinal Chemistry, Nov. 1980, 23(11): 1158-66.
Cohen, "The development and therapeutic potential of protein kinase inhibitors," Current Opinion in Chemical Biology, 1999, 3: 459-465, 1999.
Colombian Office Action in Colombian Application No. NC2018/0011550, dated May 29, 2020, 16 pages.
Cook et al., "MerTK inhibition in tumor leukocytes decreases tumor growth and metastasis," J. Clin. Invest., Aug. 2013, 123(8): 3231-42.
Cosemans et al., "Potentiating role of Gas6 and Tryo3, Axl and Mer (TAM) receptors in human and murine platelet activation and thrombus stabilization," J. of Thrombosis and Haemostasis, 2010, 8: 1797-1808.
Cruz-Cabeza et al., "Facts and Fictions about Polymorphism," Chemical Society Reviews, 2015, 44:8619-8635.
Datta et al., "Crystal Structures of Drugs: Advances in Determination, Prediction and engineering," Nature, Jan. 2004, 3:42-57.

(56) References Cited

OTHER PUBLICATIONS

Demarest et al., "Evaluation of Tyro3 expression, Gas6-mediated Akt phosphorylation, and the impact of anti-Tyro3 antibodies in melanoma cell lines," Biochemistry, May 2013, 52(18): 3102-18.
Dermer et al., "Another Anniversary for the War on Cancer," Bio/Technology, Mar. 1994, 12: 320.
Devi et al, "Poloxamer: A Novel Functional Molecule for Drug Delivery and Gene Therapy," J. Pharm. Sci. & Res., 2013, 5(8):159-165.
Divine et al., "AXL modulates extracellular matrix protein expression and is essential for invasion and metastasis in endometrial cancer," Oncotarget, Nov. 22, 2016, 7(47):77291-77305.
Dodonova et al., "Synthesis of 4-aryl-, 2, 4-diaryl-and 2, 4, 7-triarylpyrrolo [2, 3-d] pyrimidines by a combination of the Suzuki cross-coupling and N-arylation reactions," Tetrahedron, 2012, 68(1):329-339.
Dufies et al., "Mechanisms of AXL overexpression and function in Imatinib-resistant chronic myeloid leukemia cells," Oncotarget, Nov. 2011, 2(11):874-885.
Eurasian Office Action in Eurasian Application No. 201892188, dated Oct. 21, 2019, 6 pages.
Feneyrolles et al., "Axl kinase as a key target for oncology: focus on small molecule inhibitors," Mol Cancer Therapy, Sep. 2014, 13(9): 2141-8.
Freshney et al., "Culture of Animal Cells," A Manual of Basic Technique, Alan R. Liss, Inc., 1983, New York p. 4.
Ghosh, "Synthesis of 4-oxazolinephenylboronic acid and heterobiaryl oxazolines via a Suzuki reaction," Journal of Chemical Research, Apr. 2009, 4:205-207.
Gibson et al., "Pharmaceutical Preformulation and Formulation," CRC Press LLC: Boca Raton, Fla., 2009, 2nd Edition, 559 pages.
Golub et al., "Molecular Classification of Cancer: Class Discovery and Class Prediction by Gene Expression Monitoring," Science, 1999, 286: 531-537.
Gould, "Salt Selection for Basic Drugs," Int J Therapeutics, 1986, 33:201-217.
Graham et al., "Ectopic expression of the proto-oncogene Mer in pediatric T-cell acute lymphoblastic leukemia," Clinical Cancer Research, May 1, 2006 12(9):2662-2669.
Graham et al., "Cloning and developmental expression analysis of the murine c-mer tyrosine kinase," Oncogene, Jun. 1995, 10(12): 2349-59.
Graham et al., "The TAM family: phosphatidylserine sensing receptor tyrosine kinases gone awry in cancer," Nat. Rev. Cancer, Dec. 2014, 14(12): 769-85.
Gustafsson et al., "Differential expression of Axl and Gas6 in renal cell carinoma reflecting tumor advancement and survival," Clin. Cancer Res., 2009, 15: 4742-4749.
Holland et al., "R428, a Selective Small Molecule Inhibitor of Axl Kinase, Blocks Tumor Spread and Prolongs Survival in Models of Metastatic Breast Cancer," Cancer Research, Feb. 2010, 70(4): 1544-1554.
Hsieh et al., "The AXL receptor tyrosine kinase is associated with adverse prognosis and distant metastasis in esophageal squamous cell carcinoma," Oncotarget, Jun. 14, 2016, 7(24):36956-36970.
Huang et al., "Structural insights into the inhibited states of the Mer receptor tyrosine kinase," Journal of Structural Biology, 2009, 165: 88-96.
Hutterer et al., "Axl and growth arrest-specific gene 6 are frequently overexpressed in human gliomas and predict poor prognosis in patients with glioblastoma multiforme," Clinical Cancer Research, Jan. 1, 2008, 14(1):130-138.
International Search Report and Written Opinion in International Application No. PCT/US2016/031625, dated Jul. 7, 2016, 11 pages.
International Search Report and Written Opinion in International Application No. PCT/US2016/046574, dated Oct. 21, 2016, 14 pages.
International Search Report and Written Opinion in International Application No. PCT/US2016/048716, dated Nov. 2, 2016, 12 pages.
International Search Report and Written Opinion in International Application No. PCT/US2017/024270, dated Jun. 14, 2017, 18 pages.
International Search Report and Written Opinion in International Application No. PCT/US2018/052925, dated Nov. 5, 2018, 14 pages.
International Search Report and Written Opinion in International Application No. PCT/US2019/039825, dated Nov. 11, 2019, 14 pages.
International Preliminary Report on Patentability in International Application No. PCT/US2016/048716, dated Nov. 2, 2016, 12 pages.
International Preliminary Report on Patentability in International Application No. PCT/US2017/024270, dated Oct. 2, 2018, 10 pages.
International Preliminary Report on Patentability in International Application No. PCT/US2018/052925, dated Mar. 31, 2020, 8 pages.
Johnson et al., "Relationships between drug activity in NCI preclinical in vitro and in vivo models and early clinical trials," British J. of Cancer., May 18, 2001, 84(10):1424-1431.
Keegan et al., "Preclinical Evaluation of AMG 925, a FLT3/CDK4 Kinase Inhibitor for Treating Acute Myeloid Leukemia," Molecular Cancer Therapeutics, Apr. 2014, 13(4): 880-889.
Kerekes et al., "Aurora kinase inhibitors based on the imidazo[1,2-a]pyrazine core: fluorine and deuterium incorporation improve oral absorption and exposure," J. Med. Chem., 2011, 54: 201-210.
Klimke and Ludemann, "Further evidence for a S-syn correlation in the purine (β) ribosides: the solution conformation of two tricyclic analogs of adenosine and guanosine," Journal of Biosciences, 1979, 34C(9-10): 653-7.
Koorstra et al., "The Axl receptor tyrosine kinase confers an adverse prognostic influence in pancreatic cancer and represents a new threapeutic target," Cancer Biol. Ther., Apr. 2009, 8(7): 618-626.
Lai and Lemke, "An extended family of protein-tyrosine kinase genes differentially expressed in the vertebrate nervous system," Neuron, May 1991, 6(5): 691-704.
Lee-Sherick et al., "Aberrant Mer receptor tyrosine kinase expression contributes to leukemogenesis in acute myeloid leukemia," Oncogene, Nov. 2013, 32(46):5359-5368.
Lemke, "Biology of the TAM Receptors," Cold Spring Harb Perspect Biol., 2013, 5: 1-17.
Lew et al., "Differential TAM receptor-ligand-phospholipid interactions delimit differential TAM bioactivities," Elife, Sep. 2014, 3:e03385.
Li et al., "Axl as a potential therapeutic target in cancer: role of Axl in tumor growth, metastasis and angiogenesis," Oncogene, Oct. 2009, 28(39): 3442-55.
Li et al., "Discovery of AMG 925, a FLT3 and CDK4 Dual Kinase Inhibitor with Preferential Affinity for the Activated State of FLT3," Journal of Medicinal Chemistry, 2014, 57(8): 3430-3449.
Linger et al., "Mer or Axl receptor tyrosine kinase inhibition promotes apoptosis, blocks growth and enhances chemosensitivity of human non-small cell lung cancer," Oncogene, Jul. 2013, 32(29): 3420-3431.
Linger et al., "Taking aim at Mer and Axl receptor tyrosine kinases as novel therapeutic targets in solid tumors," Expert Opin. Ther. Targets, Oct. 2010, 14(10): 1073-1090.
Linger et al., "TAM Receptor Tyrosine Kinases: Biologic Functions, Signaling, and Potential Therapeutic Targeting in Human Cancer," Adv. Cancer Research, 2008, 100: 35-83.
Lippincott Williams & Wilkins, "Remington: The Science and Practice of Pharmacy," 2005, 21st ed., 1 page, Title page.
Liu et al., "Axl Expression Stratifies Patients with Poor Prognosis after Hepatectomy for Hepatocellular Carcinoma," PLOS One, May 16, 2016, 1-13.
Liu et al., "Induction, regulation, and biologic function of Axl receptor tyrosine kinase in Kaposi sarcoma," Blood, Jul. 15, 2010, 116(2):297-305.
Liu et al., "Discovery of Novel Small Molecule Mer Kinase Inhibitors for the Treatment of Pediatric Acute Lymphoblastic Leukemia," ACS Med. Chem. Lett., 2012, 3(2): 129-134.

(56) References Cited

OTHER PUBLICATIONS

Liu et al., "Discovery of Novel Small Molecule Mer Kinase Inhibitors for the Treatment of Pediatric Acute Lymphoblastic Leukemia," Supporting Information, ACS Med. Chem. Lett., 2012, 53 pages.
Liu et al., "Discovery of Small Molecule Mer Kinase Inhibitors for the Treatment of Pediatric Acute Lymphoblastic Leukemia," ACS Medicinal Chemistry Letters, 2012, 3: 129-134 Duplicate.
Liu et al., "UNC1062, a new and potent Mer inhibitor," European Journal of Medicinal Chemistry, 2013, 65: 83-93.
Lu and Lemke, "Homeostatic regulation of the immune system by receptor tyrosine kinases of the Tyro 3 family," Science, Jul. 2001, 293(5528): 306-11.
Ludwig, et al., "Small-Molecule Inhibition of Axl Targets Tumor Immune Suppression and Enhances Chemotherapy in Pancreatic Cancer," Cancer Research, Jan. 1, 2018, 78(1):246-255.
Mao et al., "Quantitation of poloxamers in pharmaceutical formulations using size exclusion chromatography and colorimetric methods," Journal of Pharmaceutical and Biomedical Analysis, 2004, 35: 1127-1142.
Mollard et al., "Design, Synthesis, and Biological Evaluation of a Series of Novel AXL Kinase Inhibitors," ACS Medicinal Chemistry Letters, 2011, 2: 907-912.
Morissette et al., "High-throughput crystallization: polymorphs, salts, co-crystals and solvates of pharmaceutical solids," Advanced Drug Delivery Reviews, 2004, 56:257-300.
Morris et al., "An Integrated Approach to the Selection of Optimal Salt Form for a New Drug Candidate," Int J Pharm., 1994, 105:209-217.
Mudduluru et al., "Myeloid zinc finger 1 induces migration, invasion, and in vivo metastasis through Axl gene expression in solid cancer," Mol. Cancer Res., Feb. 2010, 8(2): 159-169.
Myers et al., "AXL inhibitors in cancer: A medicinal chemistry perspective," Journal of Medicinal Chemistry, 2015, pp. 1-53.
Neau "Pharmaceutical Salts," Water-Insoluble Drug Formulation, 2008, 417-435.
Nishimura et al., "Autoimmune dilated cardiomyopathy in PD-1 receptor-deficient mice," Science, 2001, 291(5502): 319-22.
O'Bryan et al., "axl, a transforming gene isolated from primary human myeloid leukemia cells, encodes a novel receptor tyrosine kinase," Mol. Cell Biol., Oct. 1991, 11(10): 5016-31.
Okamoto et al., "Oligonucleotides containing 7-vinyl-7-deazaguanine as a facile strategy for expanding the functional diversity of DNA," Bioorganic & Medicinal Chemistry Letters, 2002, 12(15): 1895-1896.
Paolino et al., "The E3 ligase Cbl-b and TAM receptors regulate cancer metastasis via natural killer cells," Nature, 2014, 19 pages.
Pardoll, "The blockade of immune checkpoints in cancer immunotherapy," Nat. Rev. Cancer, Mar. 2012, 12(4): 252-64.
Powell et al., "Highly selective 2,4-diaminopyrimidine-5-carboxamide inhibitors of Sky kinase," Bioorganic & Medicinal Chemistry Letters, 2013, 23: 1046-1050.
Powell et al., "Novel and selective spiroindoline-based inhibitors of sky kinase," Bioorganic & Medicinal Chemistry Letters, 2012, 22: 190-193.
Rankin et al., "AXL is an essential factor and therapeutic target for metastatic ovarian cancer," Cancer Research, Oct. 1, 2010, 70(19), 7570-7579.
Remington's Pharmaceutical Sciences, 17th ed., Mack Publishing Company, Easton, Pa., 1985, p. 1418.
Rho et al., "MET and AXL Inhibitor NPS-1034 Exerts Efficacy against Lung Cancer Cells Resistant to EGFR Kinase Inhibitors Because of MET or AXL Activation," AARC Journals, 2013, 253-262.
Rowe et al., "Handbook of Pharmaceutical Excipients," The Pharmaceutical Press and the American Pharmaceutical Association, 2009, 6th edition, 917 pages.
Sausville et al., "Contributions of human tumor xenografts to anticancer drug development," Cancer Research, Apr. 1, 2006, 66(7):3351-3354.
Schlegel et al., "MERTK receptor tyrosine kinase is a therapeutic target in melanoma," The Journal of Clinical Investigation, May 2013, 123(5): 2257-2267.
Schroeder et al., "Discovery of N-(4-(2-Amino-3-chloropyridin-4-yloxy)-3-fluorophenyl)-4-ethoxy-1-(4-fluorophenyl)-2-oxo-1,2-dihydropyridine-3-carboxamide (BMS-777607), a Selective and Orally Efficacious Inhibitor of the Met Kinase Superfamily," J. Med. Chem., 2009, 52: 1251-1254.
Singer et al., "Photochromism of Diarylethene-Functionalized 7-Deazaguanosines," European Journal of Organic Chemistry, 2013, 14: 2766-2769.
Shibata et al., "Axl receptor blockade ameliorates pulmonary pathology resulting from primary viral infection and viral exacerbation of asthma," The Journal of Immunology, 2014, 192: 3569-3581.
Skardziute, "Optical study of the formation of pyrrolo[2,3-d]pyrimidine-based fluorescent nanoaggregates," Tetrahedron, 2013, 69(46):9566-9572.
Storey et al., "Solid State Characterization of Pharmaceuticals," 2011, 170 pages.
Strassmaier and Karpen, "Novel N7- and N1-Substituted cGMP Derivatives are Potent Activators of Cyclic Nucleotide-Gated Channels," Journal of Medicinal Chemistry, Aug. 2007, 50: 4186-4194.
Suarez et al., "Inhibitors of the TAM subfamily of tyrosine kinsases: Synthesis and biological evaluation," European Journal of Medicinal Chemistry, 2013, 61: 2-25.
Swarbrick et al., "Salt Forms of Drugs and Absorption," Encyclopedia of Pharmaceutical Technology, 1996, 13:453-499.
Tai et al., "Axl promotes cell invasion by inducing MMP-9 activity through activation of NF-kappaB and Brg-1," Oncogene, Jul. 2008, 27(29): 4044-55.
Traore et al., "New aminopyrimidine derivatives as inhibitors of the TAM family," European Journal of Medicinal Chemistry, 2013, 70: 789-801.
Tumkevicius, "Pyrrolo [2, 3-d] pyrimidine-Core-Extended n-Systems: Synthesisof 2, 4, 7-Triarylpyrrolo [2, 3-d] pyrimidines," Synlett, 2011, 12:1705-1708.
Tumkevicius, "Synthesis and photophysical properties of oligoarylenes with a pyrrolo [2, 3-d] pyrimidine core," Tetrahedron Letters (2010), 51(30), 3902-3906.
Urbonas et al., "A Novel Highly Site-Selective Synthesis of 2,4,7-Triarylpyrrolo[2,3-d]pyrimidines by a Combination of Palladium(0)-, Nickel(0)-, and Copper(I)-Catalyzed Cross-Coupling Reactions," Synlett, 2013, 24(11):1383-1386.
Waizeneggar et al., "Role of Growth arrest-specific gene 6-Mer axis in multiple myeloma," Leukemia, 2015, 29: 696-704.
Wang et al., "Mer receptor tyrosine kinase promotes invasion and survival in glioblastoma multiforme," Oncogene, Feb. 2013, 32(7): 872-882.
Wu et al., "Multisubstituted quinoxalines and pyrido[2,3-d]pyrimidines: Synthesis and Sar study as tyrosine kinase c-Met inhibitors," Bioorganic & Medicinal Chemistry Letters, 2012, 22: 6368-6372.
Xu et al., "Design, synthesis and biological evaluation of deuterated nintedanib for improving pharmacokinetic properties," J. Label Compd. Radiopharm., 2015, 58: 308-312.
Yamazoe et al., "Mechanism of formation and structural characterization of DNA adducts derived from peroxidative activation of benzidine," Carcinogenesis, Sep. 1988, 9(9): 1635-41.
Zhang et al., "Activation of the AXL kinase causes resistance to EGFR-targeted therapy in lung cancer," Nat. Genet., 2012, 44(8): 852-860.
Zhang et al., "Discovery of Mer Specific Tyrosine Kinase Inhibitors for the Treatment and Prevention of Thrombosis," Journal of Medicinal Chemistry, 2013, 56: 9693-9700.
Zhang et al., "Discovery of novel type II c-Met inhibitors based on BMS-777607," European Journal of Medicinal Chemistry, 2014, 80: 254-266.
Zhang et al., "Pseudo-Cyclization through Intramolecular Hydrogen Bond Enables Discovery of Pyridine Substituted Pyrimidines as New Mer Kinase Inhibitors," Journal of Medicinal Chemistry, 2013, 56: 6983-9692.

(56) References Cited

OTHER PUBLICATIONS

Zhang et al., "UNC20205, a Potent and Orally Bioavailable MER/FLT3 Dual Inhibitor," Journal of Medicinal Chemistry, 2014, 57: 7031-7041.

Zhang et al., "Knockdown of AXL receptor tyrosine kinase in osteosarcoma cells leads to decreased proliferation and increased apoptosis," Int. J. Immunopathol. Pharmacol., Jan.-Mar. 2013, 26(1):179-188.

Zhao, et al., "Discovery of novel Bruton's tyrosine kinase (BTK) inhibitors bearing a pyrrolo [2, 3-d]pyrimidine scaffold," Bioorganic & Medicinal Chemistry, Feb. 2015, 23(4):891-901.

Zhou et al., "Synthesis and evaluation of Janus type nucleosides as potential HCV NS5B polymerase inhibitors," Bioorganic & Medicinal Chemistry Letters, Jun. 2013, 23: 3385-3388.

Chinese Office Action in Chinese Application No. 201780031476.3, dated Oct. 28, 2020, 16 pages.

European Office Action in European Application No. 17715620.5 dated Sep. 24, 2020, 4 pages.

International Preliminary Report on Patentability in International Application No. PCT/US2019/039825, dated Jan. 7, 2021, 8 pages.

Israeli Office Action in Israeli Application No. 261,957, dated Oct. 28, 2020, 10 pages.

Japanese Office Action in Japanese Application No. 2018-550711, dated Feb. 22, 2021, 6 pages.

Ukraine Office Action in Ukraine Application No. a201810566, dated Dec. 15, 2020, 8 pages.

\* cited by examiner

XRPD: Compound I Maleic Acid Salt, Form I

TGA: Compound I Maleic Acid Salt, Form I

TGA: Compound II Phosphoric Acid Salt

XRPD: Compound II Maleic Acid Salt

DSC: Compound II Maleic Acid Salt

TGA: Compound II Maleic Acid Salt

XRPD: Compound II Hemi-Sulfuric Acid Salt

XRPD: Compound II Hydrochloric Acid Salt

DSC: Compound II Hydrochloric Acid Salt

TGA: Compound III Hydrochloric Acid Salt

XRPD: Compound II Salicylic Acid Salt

DSC: Compound II Salicylic Acid Salt

TGA: Compound II Salicylic Acid Salt

XRPD: Compound II Methanesulfonic Acid Salt

DSC: Compound II Methanesulfonic Acid Salt

TGA: Compound II Methanesulfonic Acid Salt

DSC: Compound II Ethanesulfonic Acid Salt

TGA: Compound II Ethanesulfonic Acid Salt

XRPD: Compound I Maleic Acid Salt, Form II

XRPD: Compound I Maleic Acid Salt, Form III

DSC: Compound I Maleic Acid Salt, Form III

TGA: Compound I Maleic Acid Salt, Form III

DSC: Compound I Maleic Acid Salt, Form IV

TGA: Compound I Maleic Acid Salt, Form IV

XRPD: Compound I Maleate Salt, Form V

DSC: Compound I Maleic Acid Salt, Form V

TGA: Compound I Maleic Acid Salt, Form V

SALTS OF TAM INHIBITORS

FIELD OF THE INVENTION

This disclosure provides salt forms of N-(4-(4-Amino-7-(1-isobutyrylpiperidin-4-yl)pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide and N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide, which are useful as inhibitors of TAM kinases, as well as processes and intermediates related thereto.

BACKGROUND

Receptor tyrosine kinases (RTKs) are cell surface proteins that transmit signals from the extracellular environment to the cell cytoplasm and nucleus to regulate cellular events such as survival, growth, proliferation, differentiation, adhesion and migration.

The TAM subfamily consists of three RTKs including Tyro3, AXL and Mer (Graham et al., 2014, Nature Reviews Cancer 14, 769-785; Linger et al., 2008, Advances in Cancer Research 100, 35-83). TAM kinases are characterized by an extracellular ligand binding domain consisting of two immunoglobulin-like domains and two fibronectin type III domains. Two ligands, growth arrest specific 6 (GAS6) and protein S (PROS1), have been identified for TAM kinases. GAS6 can bind to and activate all three TAM kinases, while PROS1 is a ligand for Mer and Tyro3 (Graham et al., 2014, Nature Reviews Cancer 14, 769-785).

AXL (also known as UFO, ARK, JTK11 and TYRO7) was originally identified as a transforming gene from DNA of patients with chronic myelogenous leukemia (O'Bryan et al., 1991, Mol Cell Biol 11, 5016-5031; Graham et al., 2014, Nature Reviews Cancer 14, 769-785; Linger et al., 2008, Advances in Cancer Research 100, 35-83). GAS6 binds to AXL and induces subsequent auto-phosphorylation and activation of AXL tyrosine kinase. AXL activates several downstream signaling pathways including PI3K-Akt, Raf-MAPK, PLC-PKC (Feneyrolles et al., 2014, Molecular Cancer Therapeutics 13, 2141-2148; Linger et al., 2008, Advances in Cancer Research 100, 35-83).

MER (also known as MERTK, EYK, RYK, RP38, NYK and TYRO12) was originally identified as a phospho-protein from a lymphoblastoid expression library (Graham et al., 1995, Oncogene 10, 2349-2359; Graham et al., 2014, Nature Reviews Cancer 14, 769-785; Linger et al., 2008, Advances in Cancer Research 100, 35-83). Both GAS6 and PROS1 can bind to Mer and induce the phosphorylation and activation of Mer kinase (Lew et al., 2014). Like AXL, MER activation also conveys downstream signaling pathways including PI3K-Akt and Raf-MAPK (Linger et al., 2008, Advances in Cancer Research 100, 35-83).

TYRO3 (also known as DTK, SKY, RSE, BRT, TIF, ETK2) was originally identified through a PCR-based cloning study (Lai et al., Neuron 6, 691-70, 1991; Graham et al., 2014, Nature Reviews Cancer 14, 769-785; Linger et al., 2008, Advances in Cancer Research 100, 35-83). Both ligands, GAS6 and PROS1, can bind to and activate TYRO3. Although the signaling pathways downstream of TYRO3 activation are the least studied among TAM RTKs, it appears that both PI3K-Akt and Raf-MAPK pathways are involved (Linger et al., 2008, Advances in Cancer Research 100, 35-83). AXL, MER and TYRO3 are found to be over-expressed in cancer cells.

Accordingly, there is a need for compounds and methods of use thereof for the modulation of TAM kinases in the treatment of cancer.

SUMMARY

The present application provides salts of a compound of Formula I:

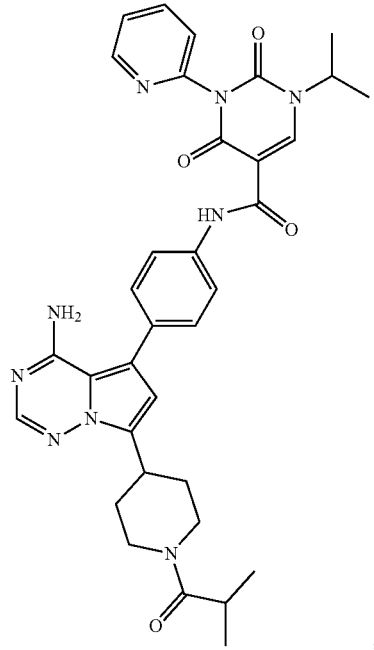

I which is useful as an inhibitor of TAM.

The present application further provides a maleic acid salt of the compound of Formula I.

The present application further provides processes of preparing salts of the compound of Formula I.

The present application provides salts of a compound of Formula II:

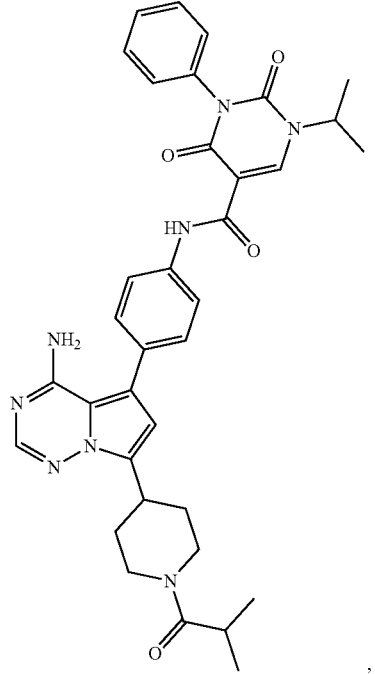

II which is useful as an inhibitor of TAM.

The present application further provides a hemi-sulfuric acid salt of the compound of Formula II.

The present application further provides a phosphoric acid salt of the compound of Formula II.

The present application further provides a maleic acid salt of the compound of Formula II.

The present application further provides a hydrochloric acid salt of the compound of Formula II.

The present application further provides a salicylic acid salt of the compound of Formula II.

The present application further provides a methanesulfonic acid salt (i.e., mesylate salt) of the compound of Formula II.

The present application further provides an ethanesulfonic acid salt (i.e., esylate salt) of the compound of Formula II.

The present application further provides processes of preparing salts of the compound of Formula II.

The present application further provides pharmaceutical compositions comprising any of the salts of the compounds of Formulae I and II.

The present application also provides methods for inhibiting TAM kinases, wherein the methods comprise contacting the TAM kinase with any of the salts of the compounds of Formulae I and II.

The present application also provides methods for inhibiting AXL and MER kinase, wherein the methods comprise contacting the AXL or MER kinase with any of the salts of the compounds of Formulae I and II.

The present application also provides methods for treating cancer in a patient, comprising administering to the patient a therapeutically effective amount of any of the salts of the compounds of Formulae I and II.

DETAILED DESCRIPTION

Compounds and Salts

Figure 1:
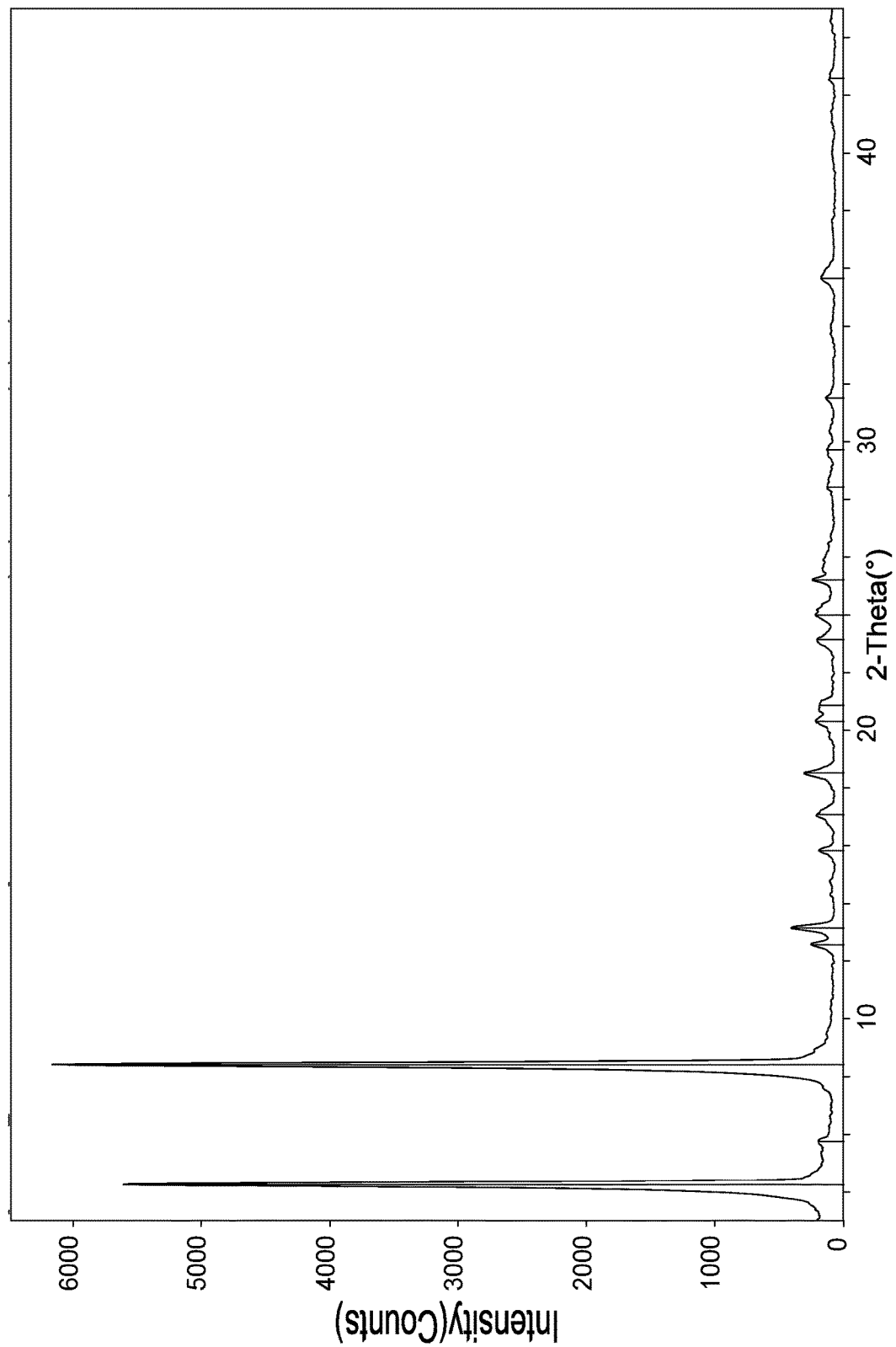
FIG. 1 shows an XRPD pattern representative of Compound I maleic acid salt, Form I.

The present application provides salts of a compound of Formula I:

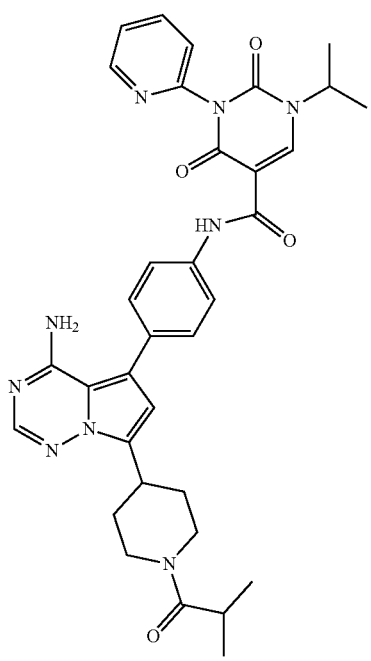

I or pharmaceutically acceptable hydrates and solvates thereof, which are useful as inhibitors of TAM.

Accordingly, in some embodiments, the present application provides N-(4-(4-Amino-7-(1-isobutyrylpiperidin-4-yl)pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide maleic acid salt (also referred to herein as maleate salt of the compound of Formula I, maleate salt of Compound I, Compound I maleate salt, or any variation thereof).

In some embodiments, the salt is a 1:1 stoichiometric ratio of N-(4-(4-Amino-7-(1-isobutyrylpiperidin-4-yl)pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide to maleic acid.

Different forms of the same substance have different bulk properties relating to, for example, hygroscopicity, solubility, stability, and the like. Forms with high melting points often have good thermodynamic stability which is advantageous in prolonging shelf-life drug formulations containing the solid form. Forms with lower melting points often are less thermodynamically stable, but are advantageous in that they have increased water solubility, translating to increased drug bioavailability. Forms that are weakly hygroscopic are desirable for their stability to heat and humidity and are resistant to degradation during long storage. The solid forms (e.g., crystalline forms) described herein can have certain advantages, for example, they may have desirable properties, such as ease of handling, ease of processing, storage stability, and ease of purification. Moreover, the crystalline forms can be useful for improving the performance characteristics of a pharmaceutical product such as dissolution profile, shelf-life, and bioavailability.

In some embodiments, the maleic acid salt of the compound of Formula I provided herein is crystalline. As used herein, "crystalline" or "crystalline form" is meant to refer to a certain lattice configuration of a crystalline substance. Different crystalline forms of the same substance typically have different crystalline lattices (e.g., unit cells) which are attributed to different physical properties that are characteristic of each of the crystalline forms. In some instances, different lattice configurations have different water or solvent content.

The different salt forms can be identified by solid state characterization methods such as by X-ray powder diffraction (XRPD). Other characterization methods such as differential scanning calorimetry (DSC), thermogravimetric analysis (TGA), dynamic vapor sorption (DVS), and the like further help identify the form as well as help determine stability and solvent/water content.

An XRPD pattern of reflections (peaks) is typically considered a fingerprint of a particular crystalline form. It is well known that the relative intensities of the XRPD peaks can widely vary depending on, inter alia, the sample preparation technique, crystal size distribution, various filters used, the sample mounting procedure, and the particular instrument employed. In some instances, new peaks may be observed or existing peaks may disappear, depending on the type of the instrument or the settings. As used herein, the term "peak" refers to a reflection having a relative height/intensity of at least about 4% of the maximum peak height/intensity. Moreover, instrument variation and other factors can affect the 2-theta values. Thus, peak assignments, such as those reported herein, can vary by plus or minus about 0.2° (2-theta), and the term "substantially" and "about" as used in the context of XRPD herein is meant to encompass the above-mentioned variations.

In the same way, temperature readings in connection with DSC, TGA, or other thermal experiments can vary about ±3° C. depending on the instrument, particular settings, sample preparation, etc. Accordingly, a crystalline form reported herein having a DSC thermogram "substantially" as shown in any of the Figures or the term "about" is understood to accommodate such variation.

In some embodiments, the salts and compounds described herein (e.g., the compound of Formula I or the maleic acid salt of the compound of Formula I) are substantially isolated. By "substantially isolated" is meant that the salt or compound is at least partially or substantially separated from the environment in which it was formed or detected. Partial separation can include, for example, a composition enriched in the salts described herein. Substantial separation can include compositions containing at least about 50%, at least about 60%, at least about 70%, at least about 80%, at least about 90%, at least about 95%, at least about 97%, or at least about 99% by weight of the salts described herein, or salt thereof. Methods for isolating compounds and their salts are routine in the art.

The maleic acid salt of the compound of Formula I can be prepared in various crystalline forms including, e.g., Form I, Form II, Form III, Form IV, or Form V.

Compound of Formula I Maleic Acid Salt, Form I:

Provided herein are embodiments (i)-(x) of a crystalline form of Compound of Formula I, referred to as Form I, which is described below in Examples 1 and 7.

(i) In some embodiments, the maleic acid salt of the compound of Formula I has at least one XRPD peak, in terms of 2-theta, selected from about 4.3°, about 8.4°, about 12.6°, about 13.2°, and about 18.5°.

(ii) In some embodiments, the maleic acid salt of the compound of Formula I has at least two XRPD peaks, in terms of 2-theta, selected from about 4.3°, about 8.4°, about 12.6°, about 13.2°, and about 18.5°.

(iii) In some embodiments, the maleic acid salt of the compound of Formula I has at least three XRPD peaks, in terms of 2-theta, selected from about 4.3°, about 8.4°, about 12.6°, about 13.2°, and about 18.5°.

(iv) In some embodiments, the maleic acid salt of the compound of Formula I has at least four XRPD peak, in terms of 2-theta, selected from about 4.3°, about 8.4°, about 12.6°, about 13.2°, and about 18.5°.

(v) In some embodiments, the maleic acid salt of the compound of Formula I comprises the following XRPD peaks, in terms of 2-theta: about 4.3°, about 8.4°, about 12.6°, about 13.2°, and about 18.5°.

(vi) In some embodiments, the maleic acid salt of the compound of Formula I comprises the following XRPD peaks, in terms of 2-theta: about 4.3°, about 8.4°, and about 13.2°.

(vii) In some embodiments, the maleic acid salt of the compound of Formula I has an XRPD profile substantially as shown in FIG. 1.

(viii) In some embodiments, the maleic acid salt of the compound of Formula I has a DSC thermogram having an endothermic peak at about 211° C.

Figure 2:
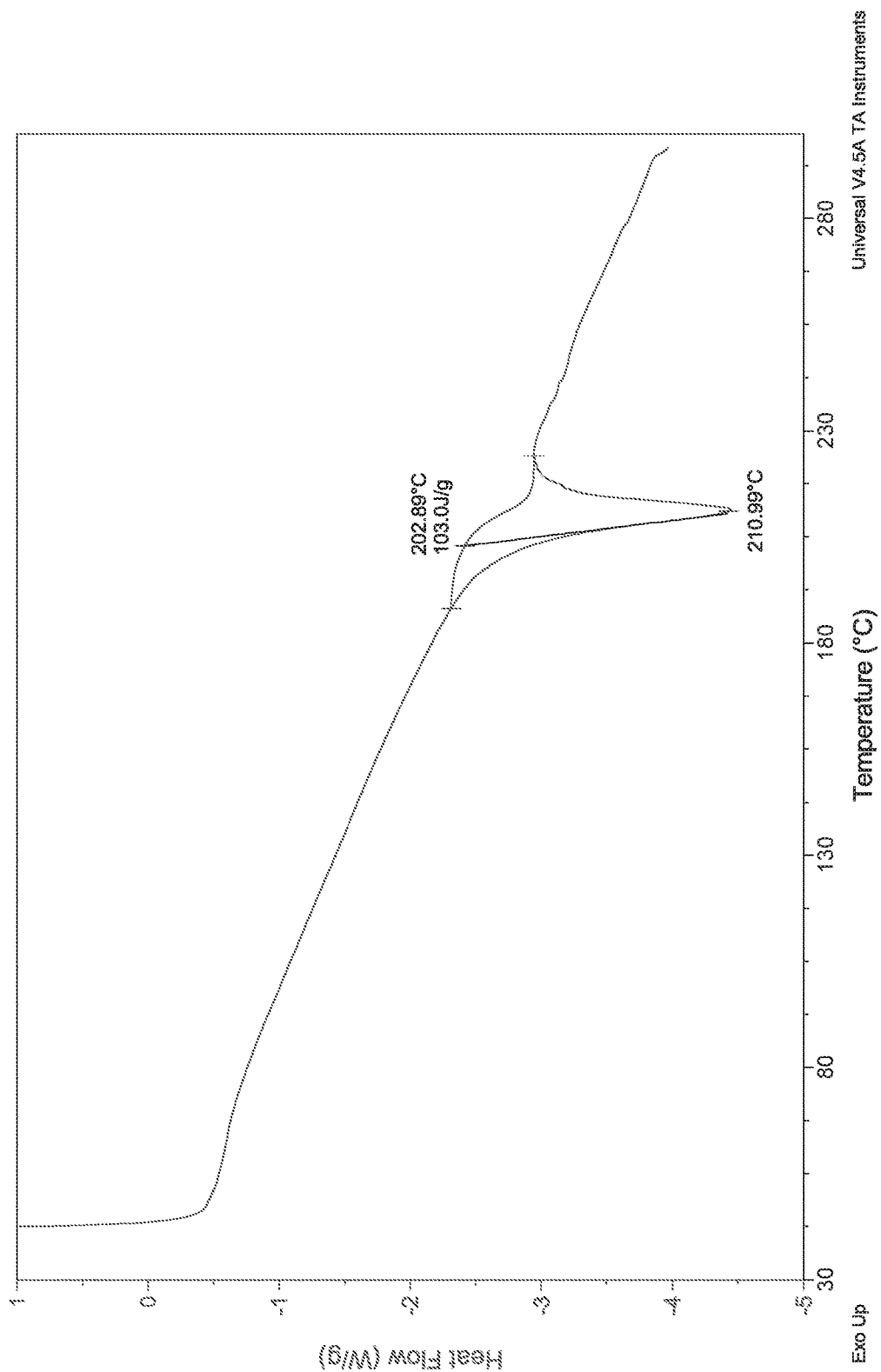
FIG. 2 shows a DSC thermogram representative of Compound I maleic acid salt, Form I.

(ix) In some embodiments, the maleic acid salt of the compound of Formula I has a DSC thermogram substantially as shown in FIG. 2.

Figure 3:
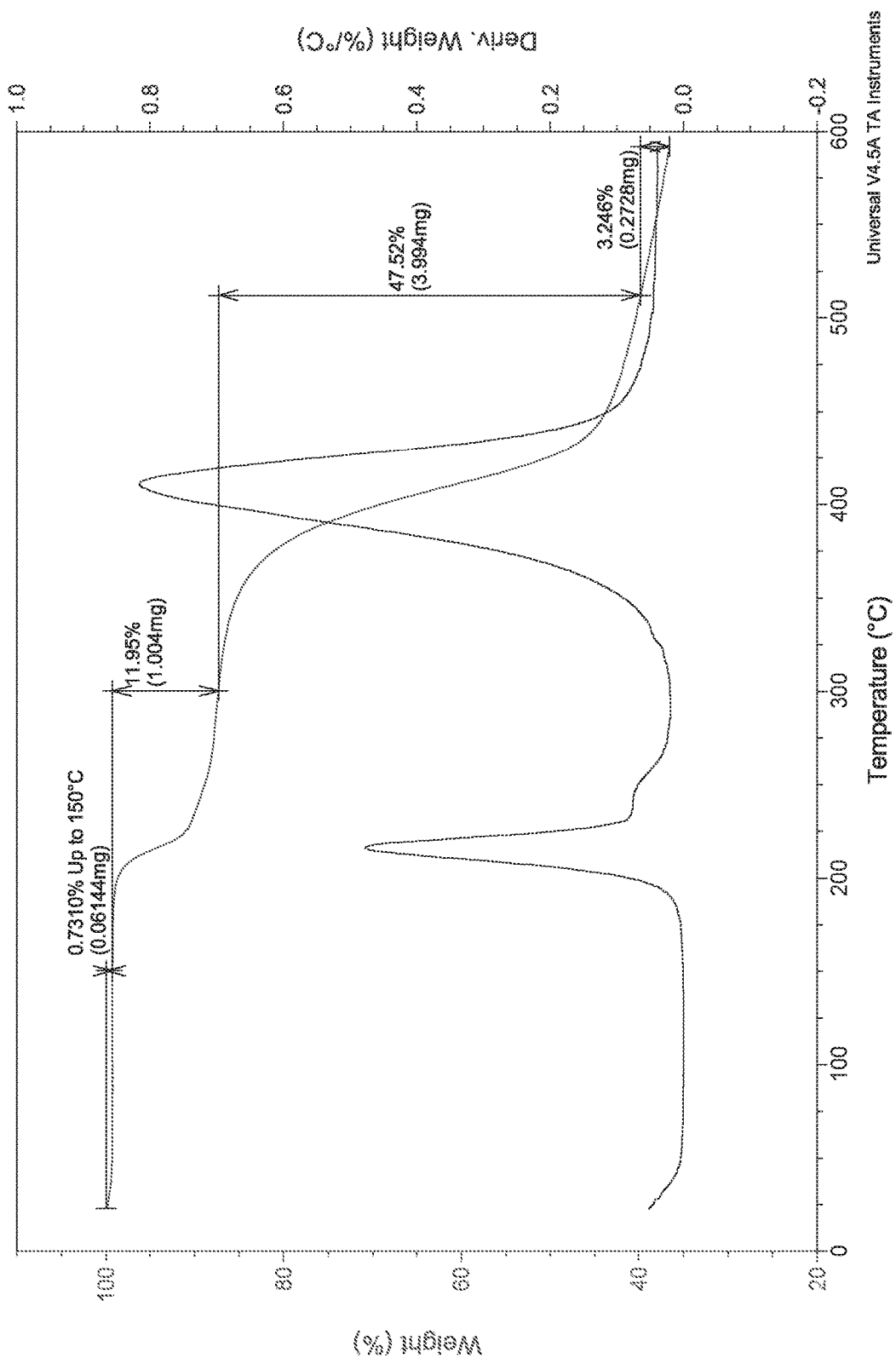
FIG. 3 shows TGA data representative of Compound I maleic acid salt, Form I.

(x) In some embodiments, the maleic acid salt of the compound of Formula I has a TGA thermogram substantially as shown in FIG. 3.

Compound of Formula I Maleic Acid Salt, Form II:

Provided herein is a crystalline form of Compound I, referred to as Form II, which is described below in Examples 16 and 17.

In some embodiments, Form II of the maleic acid salt of the compound of Formula I has at least one XRPD peak, in terms of 2-theta, selected from about 3.8°, about 7.8°, about 23.5°, and about 26.0°.

In some embodiments, Form II of the maleic acid salt of the compound of Formula I has at least two XRPD peaks, in terms of 2-theta, selected from about 3.8°, about 7.8°, about 23.5°, and about 26.0°.

In some embodiments, Form II of the maleic acid salt of the compound of Formula I has at least three XRPD peaks, in terms of 2-theta, selected from about 3.8°, about 7.8°, about 23.5°, and about 26.0°.

In some embodiments, Form II the maleic acid salt of the compound of Formula I comprises the following XRPD peaks, in terms of 2-theta: about 3.8°, about 7.8°, about 23.5°, and about 26.0°.

In some embodiments, Form II of the maleic acid salt of the compound of Formula I comprises the following XRPD peaks, in terms of 2-theta: about 3.8°, about 7.8°, and about 23.5°.

Figure 25:
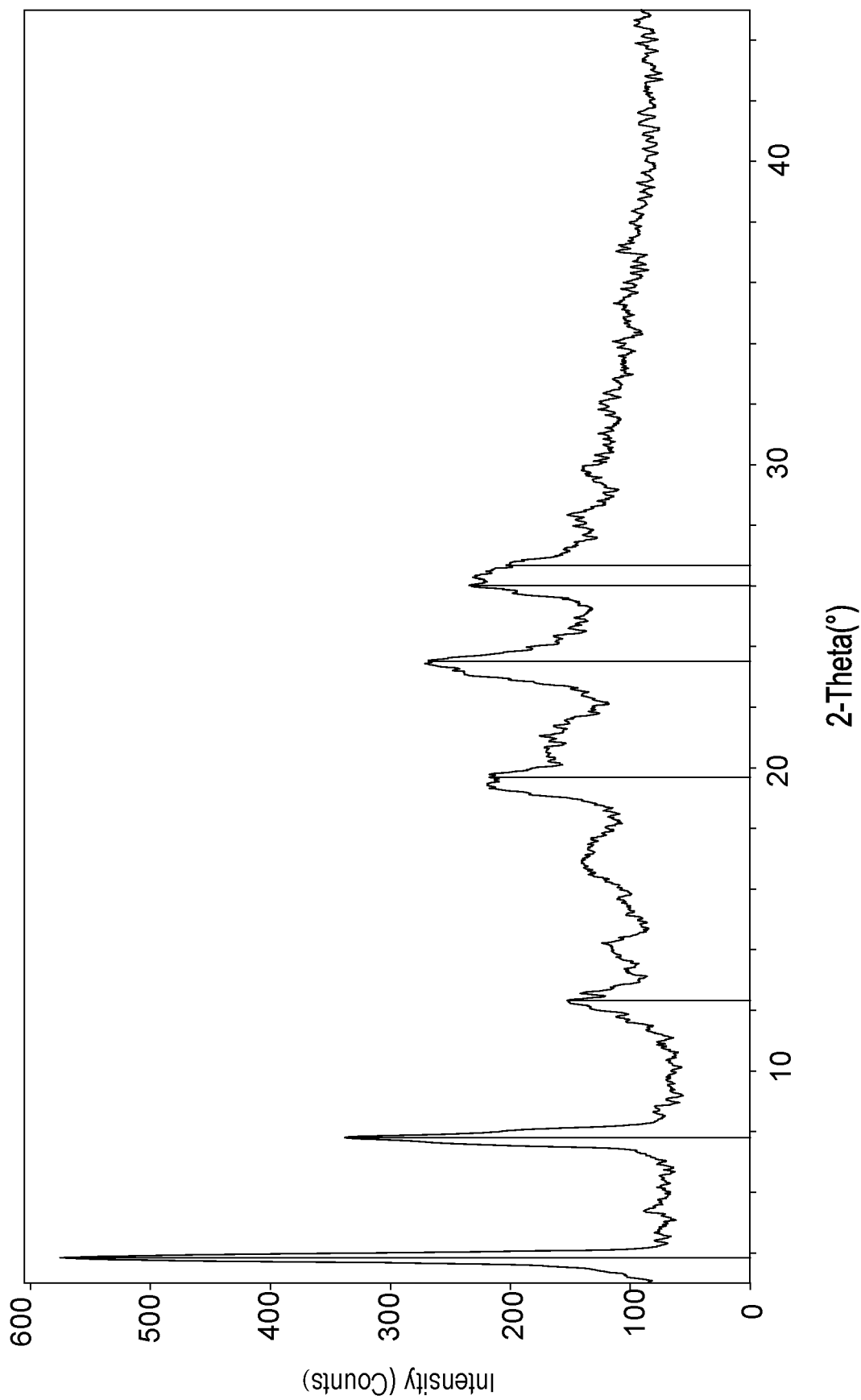
FIG. 25 shows an XRPD pattern representative of Compound I maleic acid salt, Form II.

In some embodiments, Form II of the maleic acid salt of the compound of Formula I has an XRPD profile substantially as shown in FIG. 25.

Compound of Formula I Maleic Acid Salt, Form III:

Provided herein is a crystalline form of Compound I, referred to as Form III, which is described below in Examples 16 and 18.

In some embodiments, Form III of the maleic acid salt of the compound of Formula I has at least one XRPD peak, in terms of 2-theta, selected from about 3.8°, about 7.7°, about 12.1°, about 18.9°, and about 20.6°.

In some embodiments, Form III of the maleic acid salt of the compound of Formula I has at least two XRPD peaks, in terms of 2-theta, selected from about 3.8°, about 7.7°, about 12.1°, about 18.9°, and about 20.6°.

In some embodiments, Form III of the maleic acid salt of the compound of Formula I has at least three XRPD peaks, in terms of 2-theta, selected from about 3.8°, about 7.7°, about 12.1°, about 18.9°, and about 20.6°.

In some embodiments, Form III of the maleic acid salt of the compound of Formula I has at least four XRPD peaks, in terms of 2-theta, selected from about 3.8°, about 7.7°, about 12.1°, about 18.9°, and about 20.6°.

In some embodiments, Form III the maleic acid salt of the compound of Formula I comprises the following XRPD peaks, in terms of 2-theta: 3.8°, about 7.7°, about 12.1°, about 18.9°, and about 20.6°.

In some embodiments, Form III of the maleic acid salt of the compound of Formula I comprises the following XRPD peaks, in terms of 2-theta: about 3.8°, about 7.7°, about 12.1° and about 18.9°.

Figure 26:
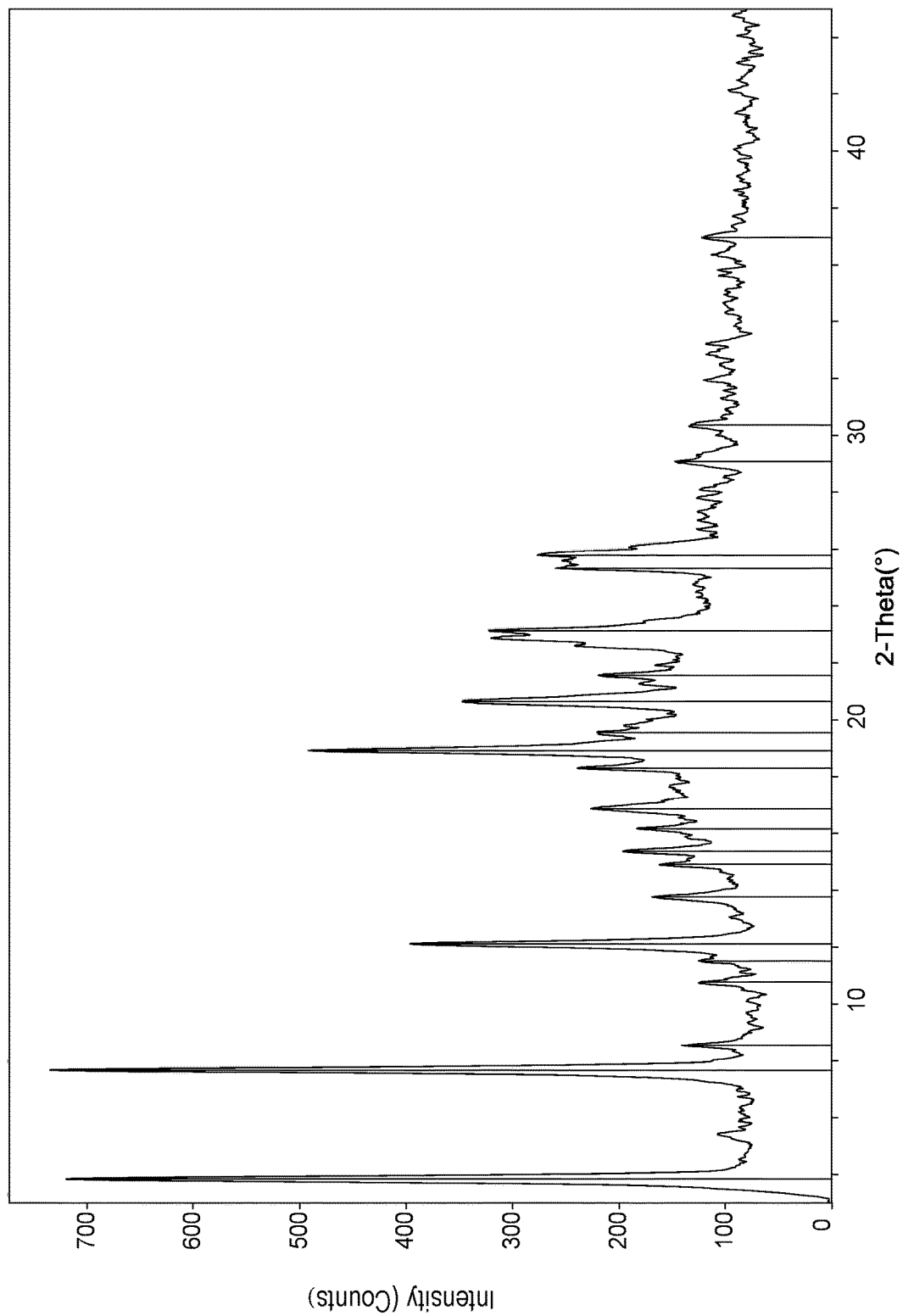
FIG. 26 shows an XRPD pattern representative of Compound I maleic acid salt, Form III.

In some embodiments, Form III of the maleic acid salt of the compound of Formula I has an XRPD profile substantially as shown in FIG. 26.

In some embodiments, Form III of the maleic acid salt of the compound of Formula I has a DSC thermogram having endothermic peaks at about 165.4° C. and about 195.4° C. In some embodiments, Form III of the maleic acid salt of the compound of Formula I has a DSC thermogram having an endothermic peak at about 165.4° C. In some embodiments, Form III of the maleic acid salt of the compound of Formula I has a DSC thermogram having an endothermic peak at about 195.4° C.

Figure 27:
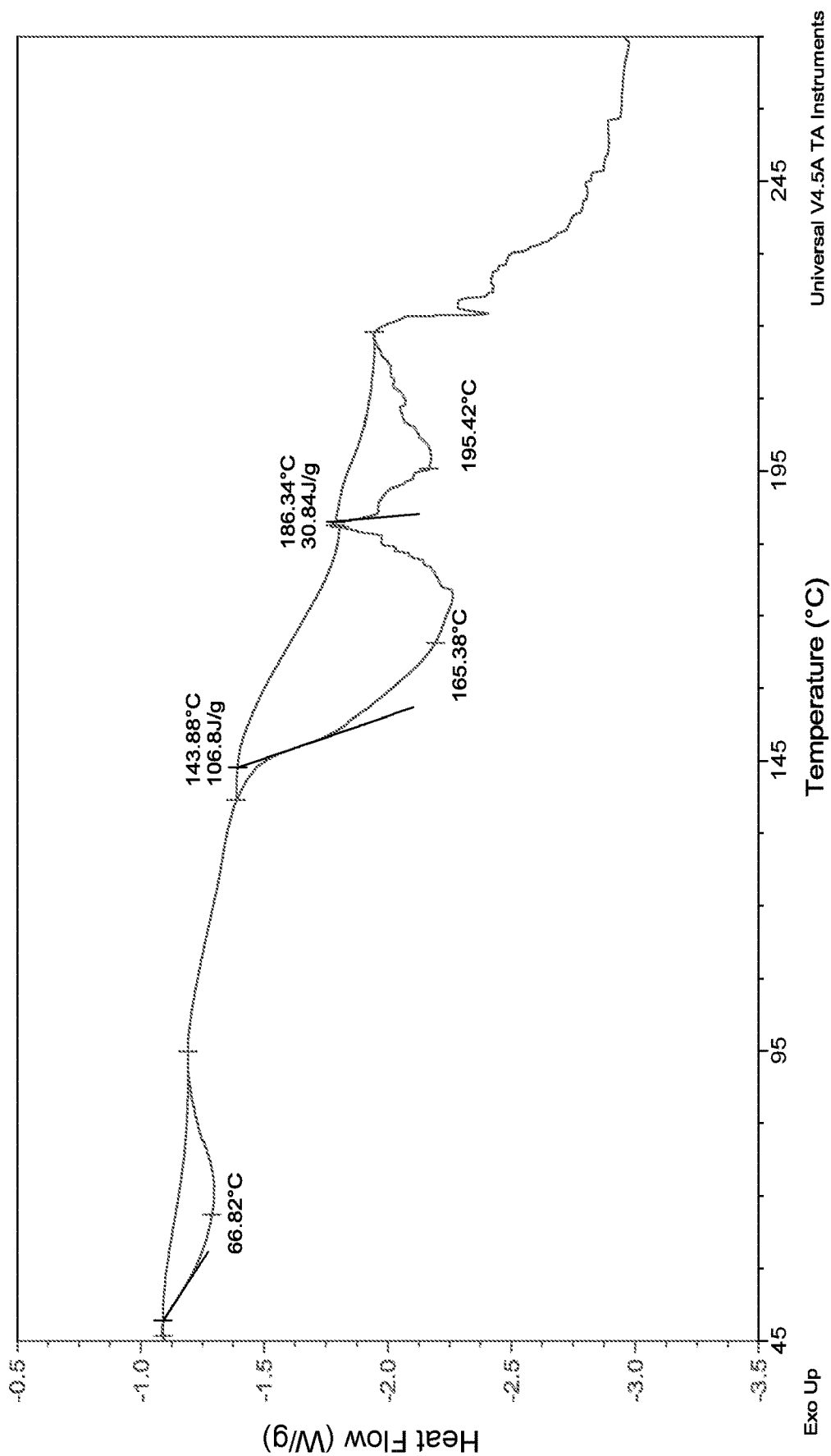
FIG. 27 shows a DSC thermogram representative of Compound I maleic acid salt, Form III.

In some embodiments, Form III of the maleic acid salt of the compound of Formula I has a DSC thermogram substantially as shown in FIG. 27.

Figure 28:
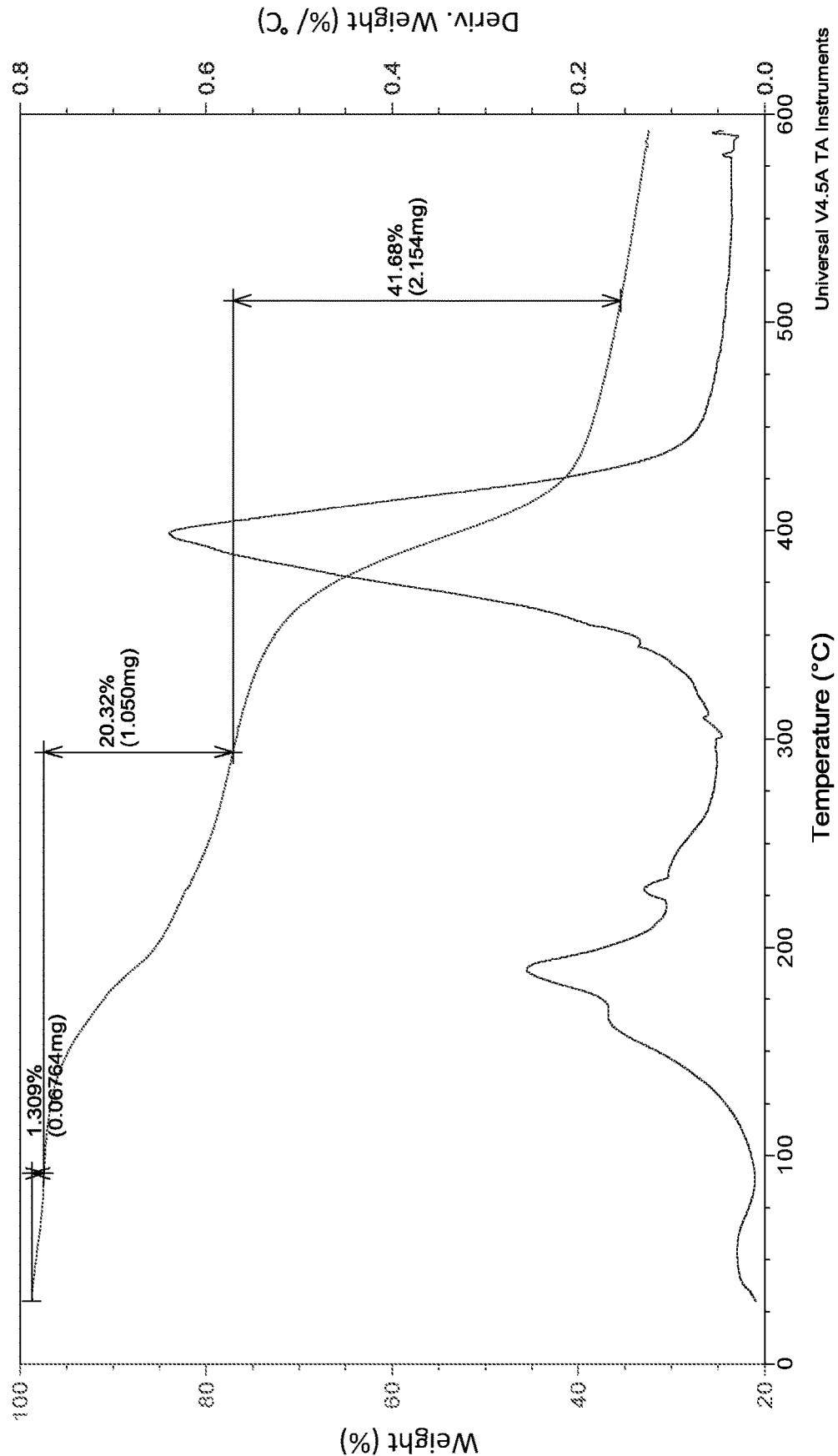
FIG. 28 shows TGA data representative of Compound I maleic acid salt, Form III.

In some embodiments, Form III of the maleic acid salt of the compound of Formula I has a TGA thermogram substantially as shown in FIG. 28.

Compound of Formula I Maleic Acid Salt, Form IV:

Provided herein is a crystalline form of Compound I, referred to as Form IV, which is described below in Examples 16 and 19.

In some embodiments, Form IV of the maleic acid salt of the compound of Formula I has at least one XRPD peak, in terms of 2-theta, selected from about 3.9°, about 4.6°, about 7.8°, about 9.1°, and about 22.8°.

In some embodiments, Form IV of the maleic acid salt of the compound of Formula I has at least two XRPD peaks, in terms of 2-theta, selected from about 3.9°, about 4.6°, about 7.8°, about 9.1°, and about 22.8°.

In some embodiments, Form IV of the maleic acid salt of the compound of Formula I has at least three XRPD peaks, in terms of 2-theta, selected from about 3.9°, about 4.6°, about 7.8°, about 9.1°, and about 22.8°.

In some embodiments, Form IV of the maleic acid salt of the compound of Formula I has at least four XRPD peaks, in terms of 2-theta, selected from about 3.9°, about 4.6°, about 7.8°, about 9.1°, and about 22.8°.

In some embodiments, Form IV the maleic acid salt of the compound of Formula I comprises the following XRPD peaks, in terms of 2-theta: about 3.9°, about 4.6°, about 7.8°, about 9.1°, and about 22.8°.

In some embodiments, Form IV of the maleic acid salt of the compound of Formula I comprises the following XRPD peaks, in terms of 2-theta: about 3.9°, about 4.6°, about 7.8°, and about 9.1°.

Figure 29:
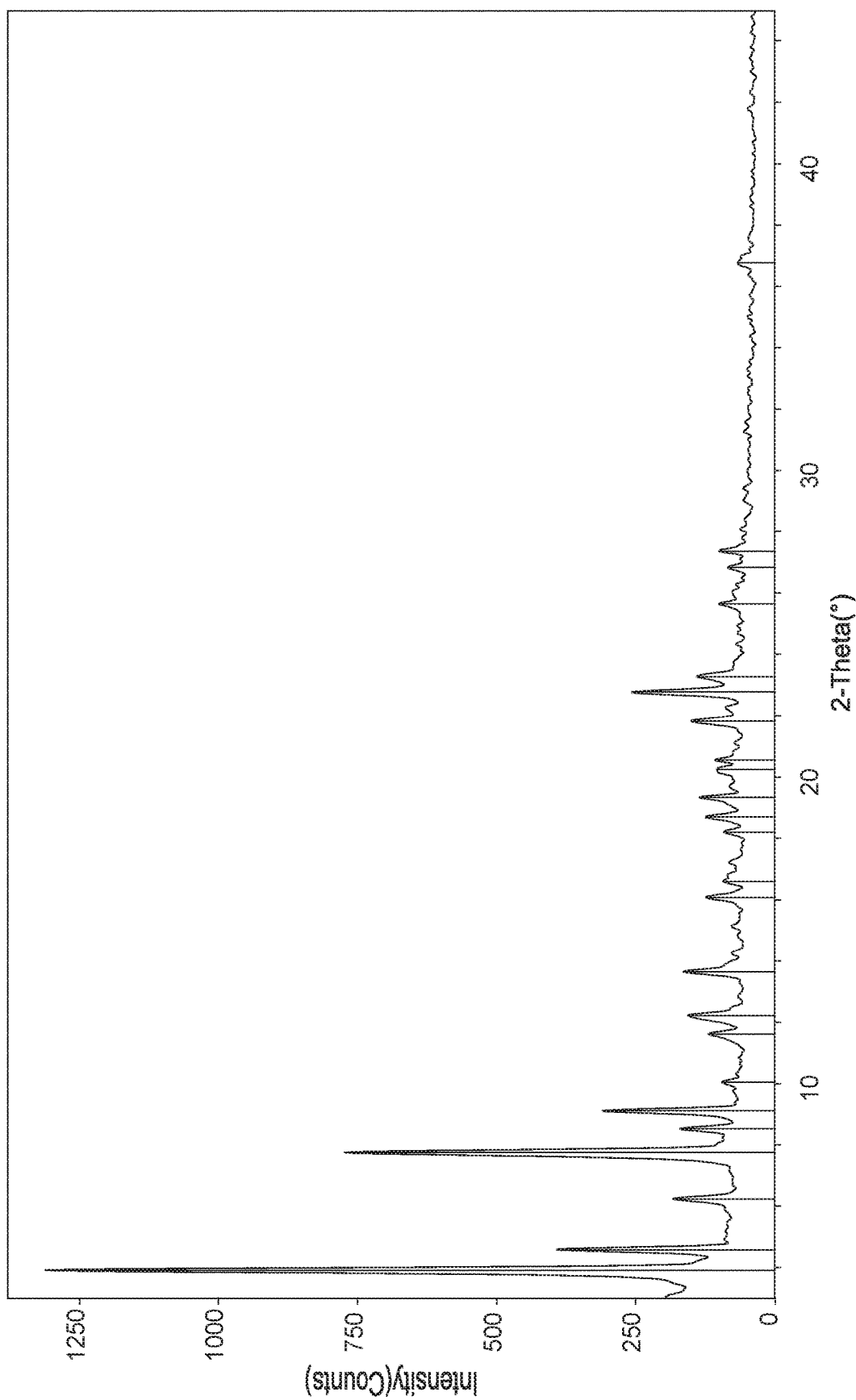
FIG. 29 shows an XRPD pattern representative of Compound I maleic acid salt, Form IV.

In some embodiments, Form IV of the maleic acid salt of the compound of Formula I has an XRPD profile substantially as shown in FIG. 29.

In some embodiments, Form IV of the maleic acid salt of the compound of Formula I has a DSC thermogram having endothermic peaks at about 152.1° C. and 202.6° C. In some embodiments, Form IV of the maleic acid salt of the compound of Formula I has a DSC thermogram having an endothermic peak at about 152.1° C. In some embodiments, Form IV of the maleic acid salt of the compound of Formula I has a DSC thermogram having an endothermic peak at about 202.6° C.

Figure 30:
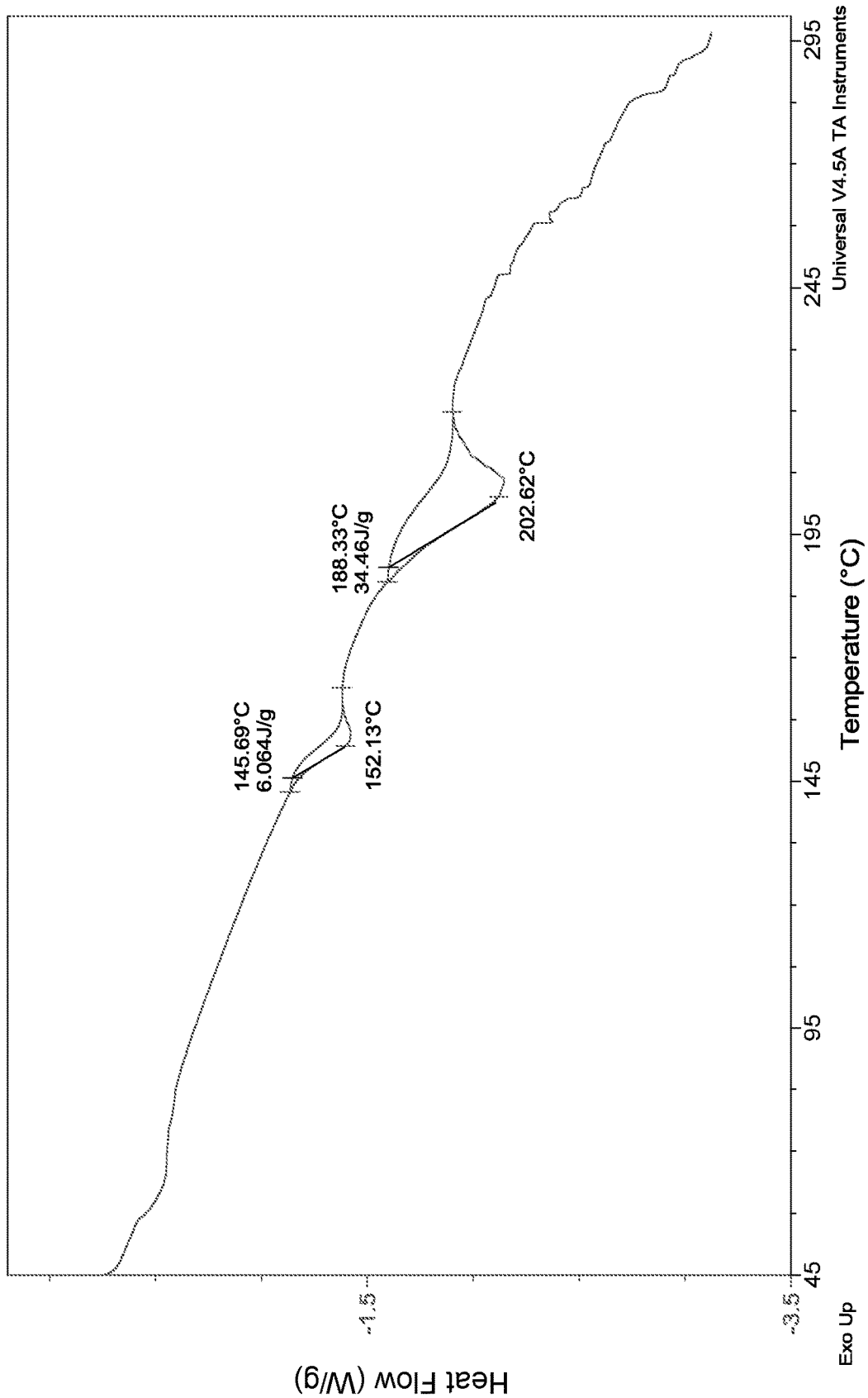
FIG. 30 shows a DSC thermogram representative of Compound I maleic acid salt, Form IV.

In some embodiments, Form IV of the maleic acid salt of the compound of Formula I has a DSC thermogram substantially as shown in FIG. 30.

Figure 31:
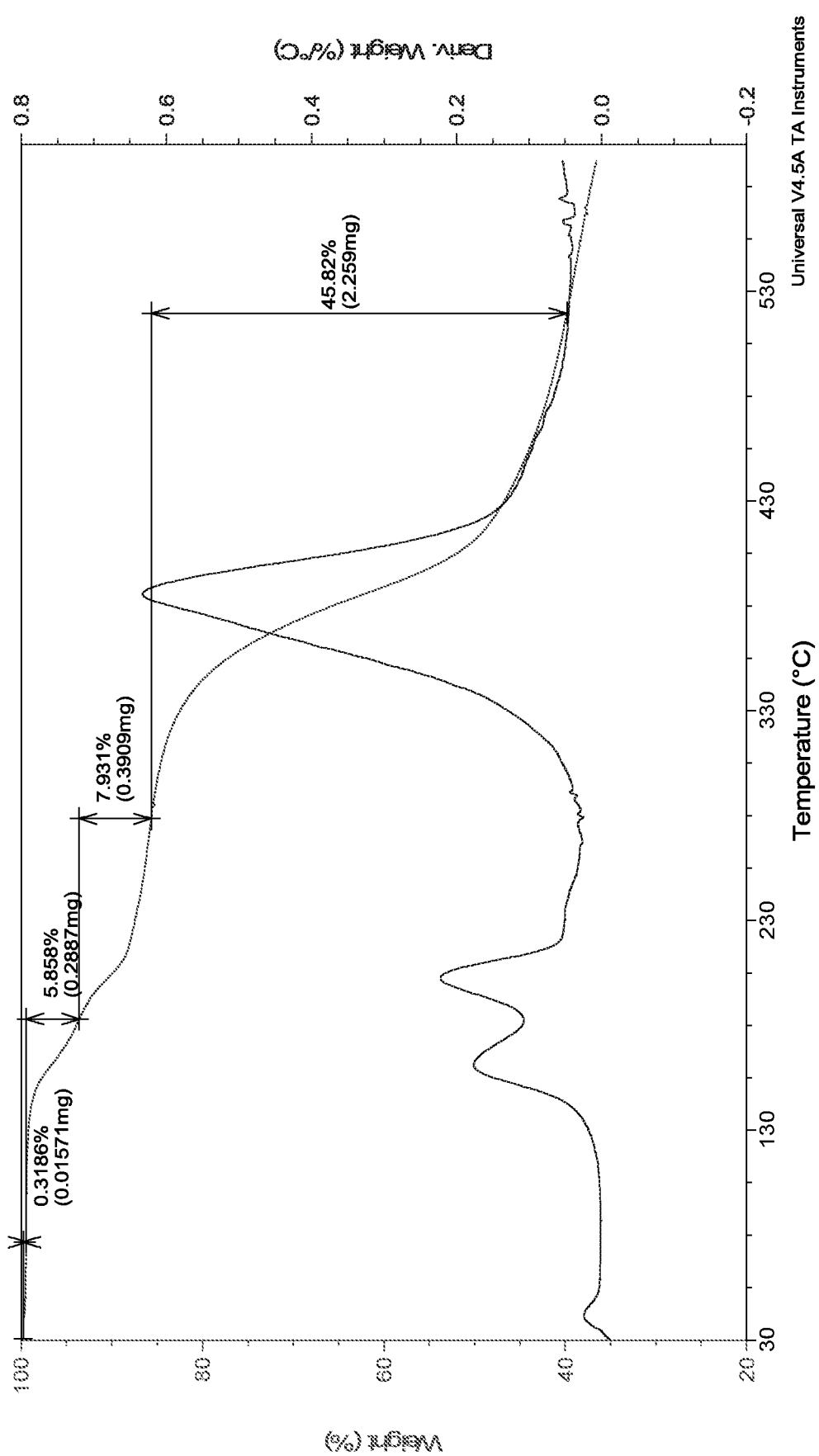
FIG. 31 shows TGA data representative of Compound I maleic acid salt, Form IV.

In some embodiments, Form IV of the maleic acid salt of the compound of Formula I has a TGA thermogram substantially as shown in FIG. 31.

Compound of Formula I Maleic Acid Salt, Form V.

Provided herein is a crystalline form of Compound I, referred to as Form V, which is described below in Examples 16 and 20.

In some embodiments, Form V of the maleic acid salt of the compound of Formula I has at least one XRPD peak, in terms of 2-theta, selected from about 4.1°, about 8.3°, about 8.8°, about 18.0°, and about 27.3°.

In some embodiments, Form V of the maleic acid salt of the compound of Formula I has at least two XRPD peaks, in terms of 2-theta, selected from about 4.1°, about 8.3°, about 8.8°, about 18.0°, and about 27.3°.

In some embodiments, Form V of the maleic acid salt of the compound of Formula I has at least three XRPD peaks, in terms of 2-theta, selected from about 4.1°, about 8.3°, about 8.8°, about 18.0°, and about 27.3°.

In some embodiments, Form V of the maleic acid salt of the compound of Formula I has at least four XRPD peaks, in terms of 2-theta, selected from about 4.1°, about 8.3°, about 8.8°, about 18.0°, and about 27.3°.

In some embodiments, Form V the maleic acid salt of the compound of Formula I comprises the following XRPD peaks, in terms of 2-theta: about 4.1°, about 8.3°, about 8.8°, about 18.0°, and about 27.3°.

In some embodiments, Form V of the maleic acid salt of the compound of Formula I comprises the following XRPD peaks, in terms of 2-theta: about 4.1°, about 8.3°, about 8.8°, and about 27.3°.

Figure 32:
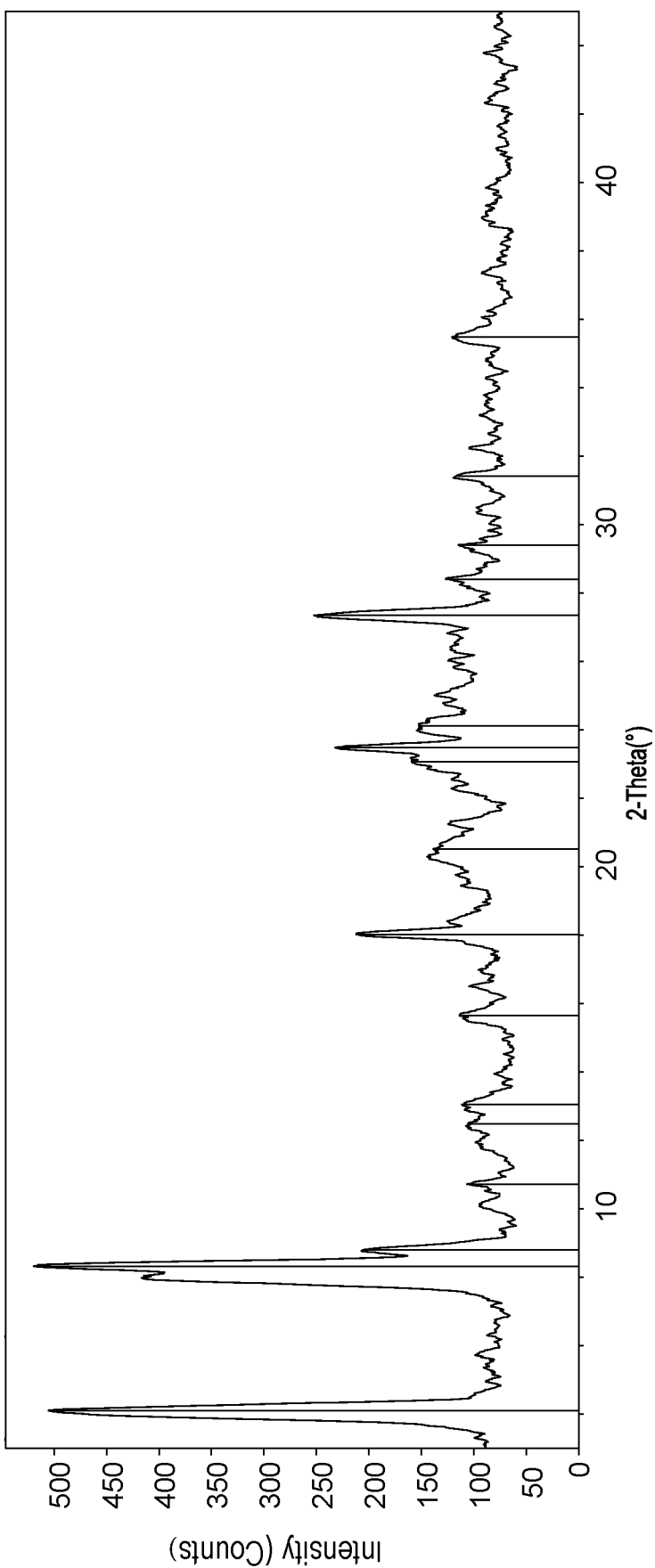
FIG. 32 shows an XRPD pattern representative of Compound I maleic acid salt, Form V.

In some embodiments, Form V of the maleic acid salt of the compound of Formula I has an XRPD profile substantially as shown in FIG. 32.

In some embodiments, Form V of the maleic acid salt of the compound of Formula I has a DSC thermogram having an endothermic peak at about 200.1° C.

Figure 33:
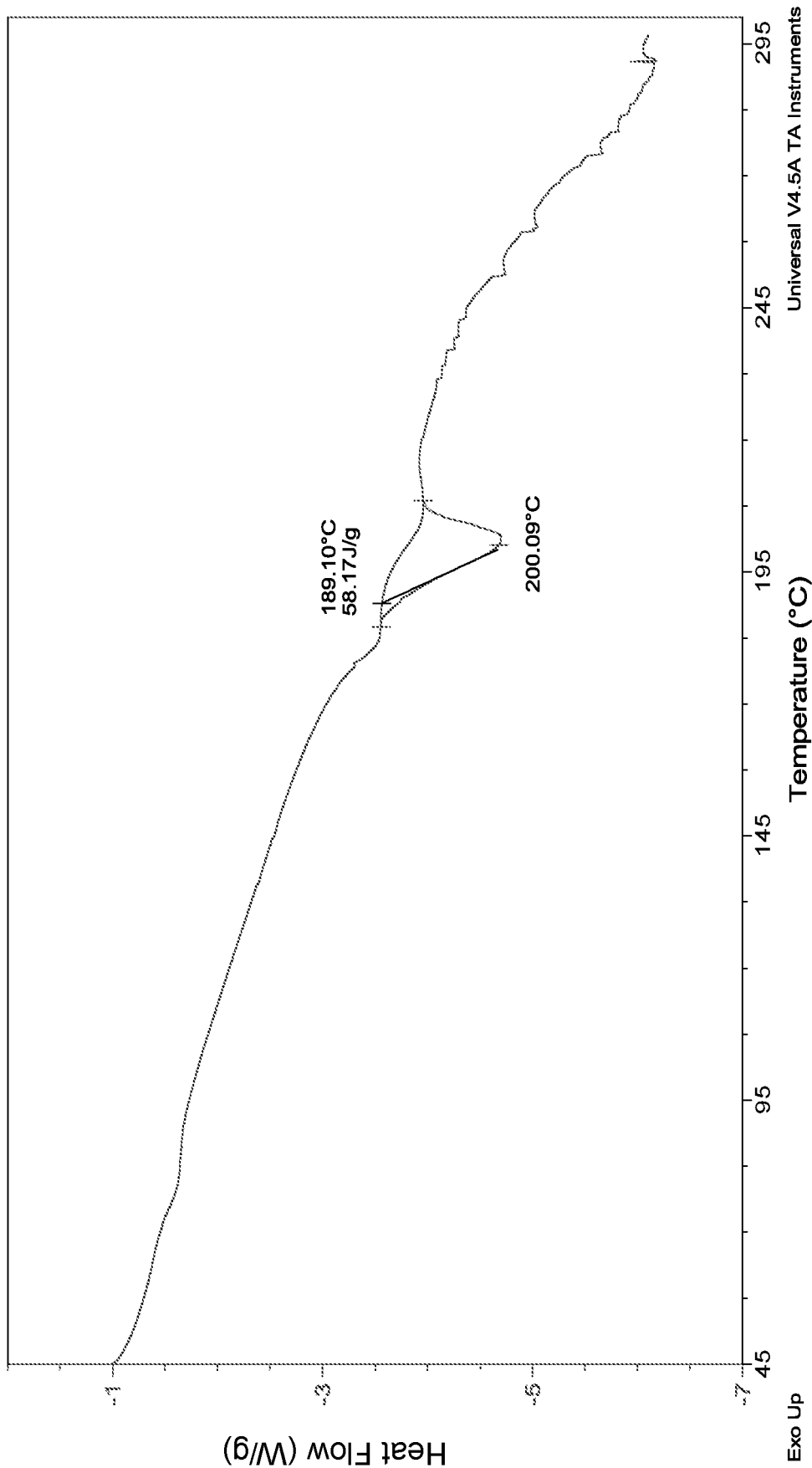
FIG. 33 shows a DSC thermogram representative of Compound I maleic acid salt, Form V.

In some embodiments, Form V of the maleic acid salt of the compound of Formula I has a DSC thermogram substantially as shown in FIG. 33.

Figure 34:
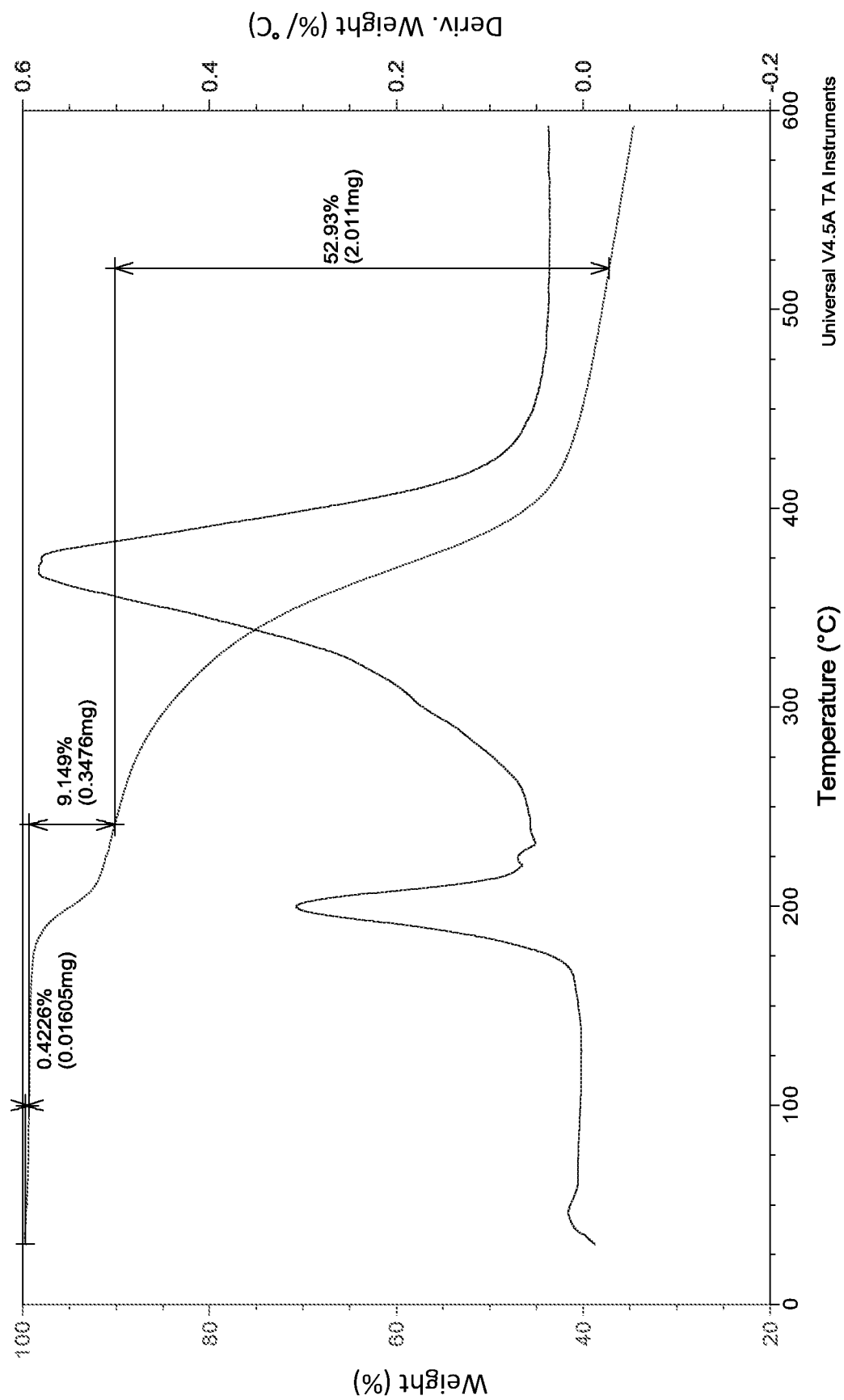
FIG. 34 shows TGA data representative of Compound I maleic acid salt, Form V.

In some embodiments, Form V of the maleic acid salt of the compound of Formula I has a TGA thermogram substantially as shown in FIG. 34.

The present application also provides salts of a compound of Formula II:

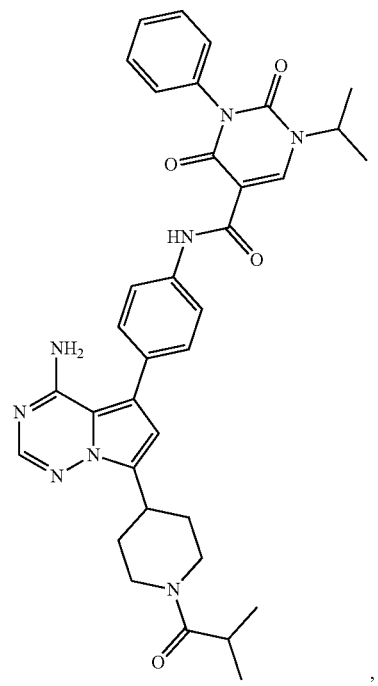

or pharmaceutically acceptable hydrates and solvates thereof, which are useful as inhibitors of TAM.

Accordingly, in some embodiments, the present application provides a salt selected from:

N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide phosphoric acid salt;

N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide maleic acid salt;

N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide hemisulfuric acid salt;

N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide hydrochloric acid salt;

N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide salicylic acid salt;

N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide methanesulfonic acid salt; and N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide ethanesulfonic acid salt, or pharmaceutically acceptable solvates and hydrates thereof.

In some embodiments, the present application provides N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide phosphoric acid salt (also referred to herein as phosphate salt of the compound of Formula II, phosphate salt of Compound II, Compound II phosphate salt, or any variation thereof).

In some embodiments, the salt is a 1:1 stoichiometric ratio of N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide to phosphoric acid.

In some embodiments, the phosphoric acid salt of the compound of Formula II is crystalline.

In some embodiments, the phosphoric acid salt of the compound of Formula II is substantially isolated.

In some embodiments, the phosphoric acid salt of the compound of Formula II has at least one XRPD peak, in terms of 2-theta, selected from about 5.3°, about 9.1°, about 14.9°, about 15.8°, and about 19.3°. In some embodiments, the phosphoric acid salt of the compound of Formula II has at least two XRPD peaks, in terms of 2-theta, selected from about 5.3°, about 9.1°, about 14.9°, about 15.8°, and about 19.3°. In some embodiments, the phosphoric acid salt of the compound of Formula II has at least three XRPD peaks, in terms of 2-theta, selected from about 5.3°, about 9.1°, about 14.9°, about 15.8°, and about 19.3°. In some embodiments, the phosphoric acid salt of the compound of Formula II has at least four XRPD peaks, in terms of 2-theta, selected from about 5.3°, about 9.1°, about 14.9°, about 15.8°, and about 19.3°. In some embodiments, the phosphoric acid salt of the compound of Formula II comprises the following XRPD peaks, in terms of 2-theta: 5.3°, about 9.1°, about 14.9°, about 15.8°, and about 19.3°.

Figure 4:
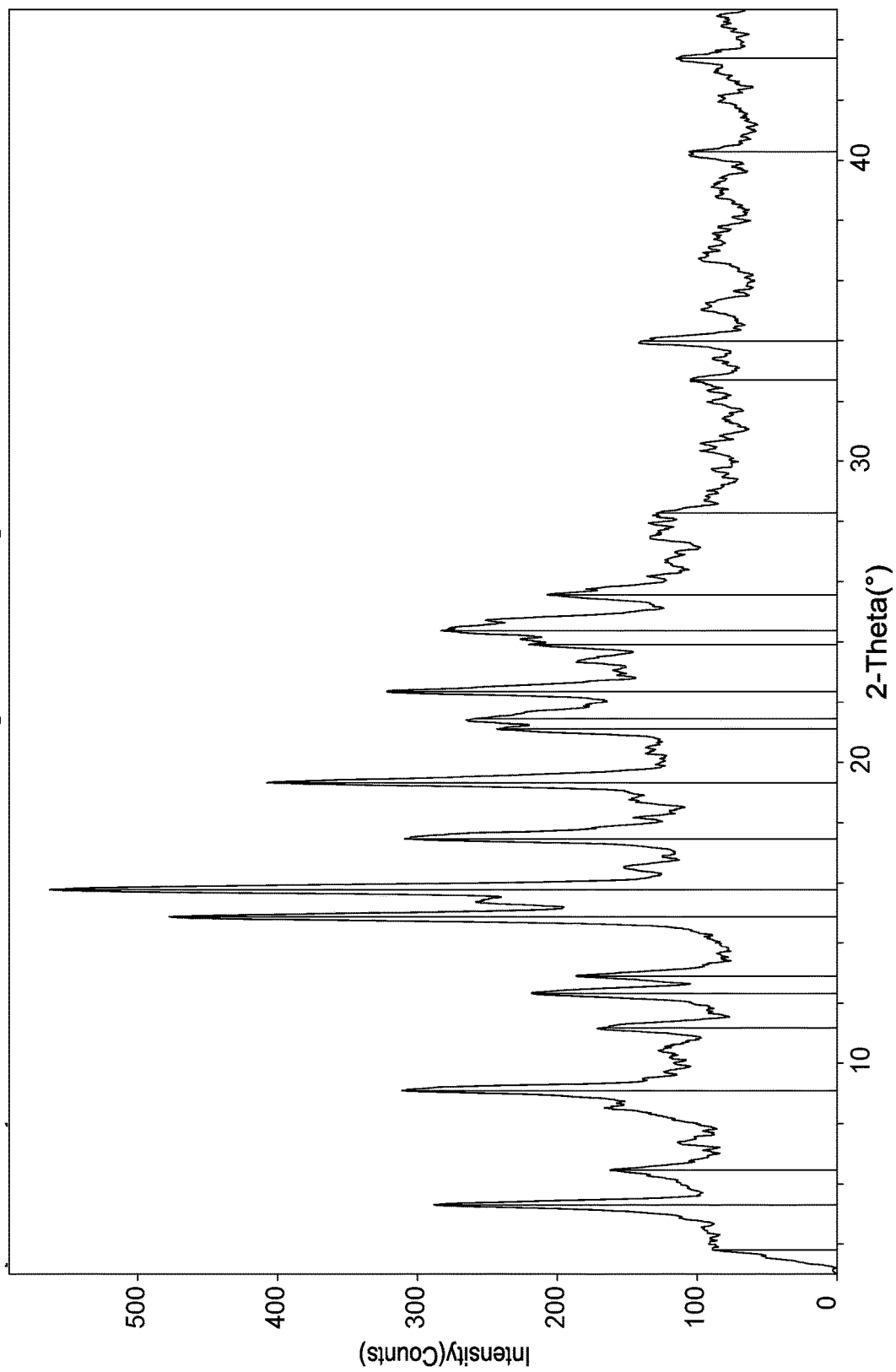
FIG. 4 shows an XRPD pattern representative of Compound II phosphoric acid salt.

In some embodiments, the phosphoric acid salt of the compound of Formula II has an XRPD profile substantially as shown in FIG. 4.

Figure 5:
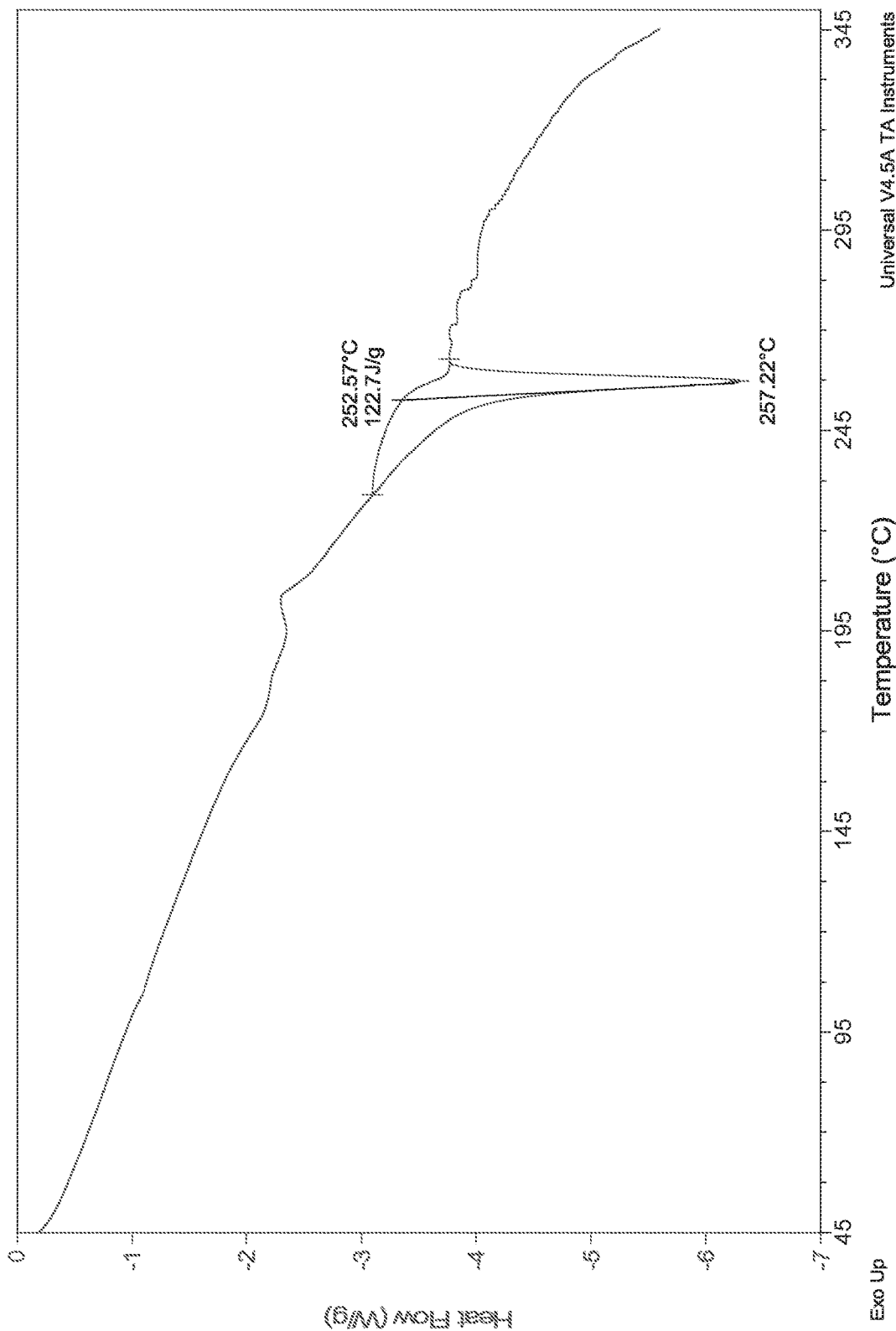
FIG. 5 shows a DSC thermogram representative of Compound II phosphoric acid salt.
Figure 6:
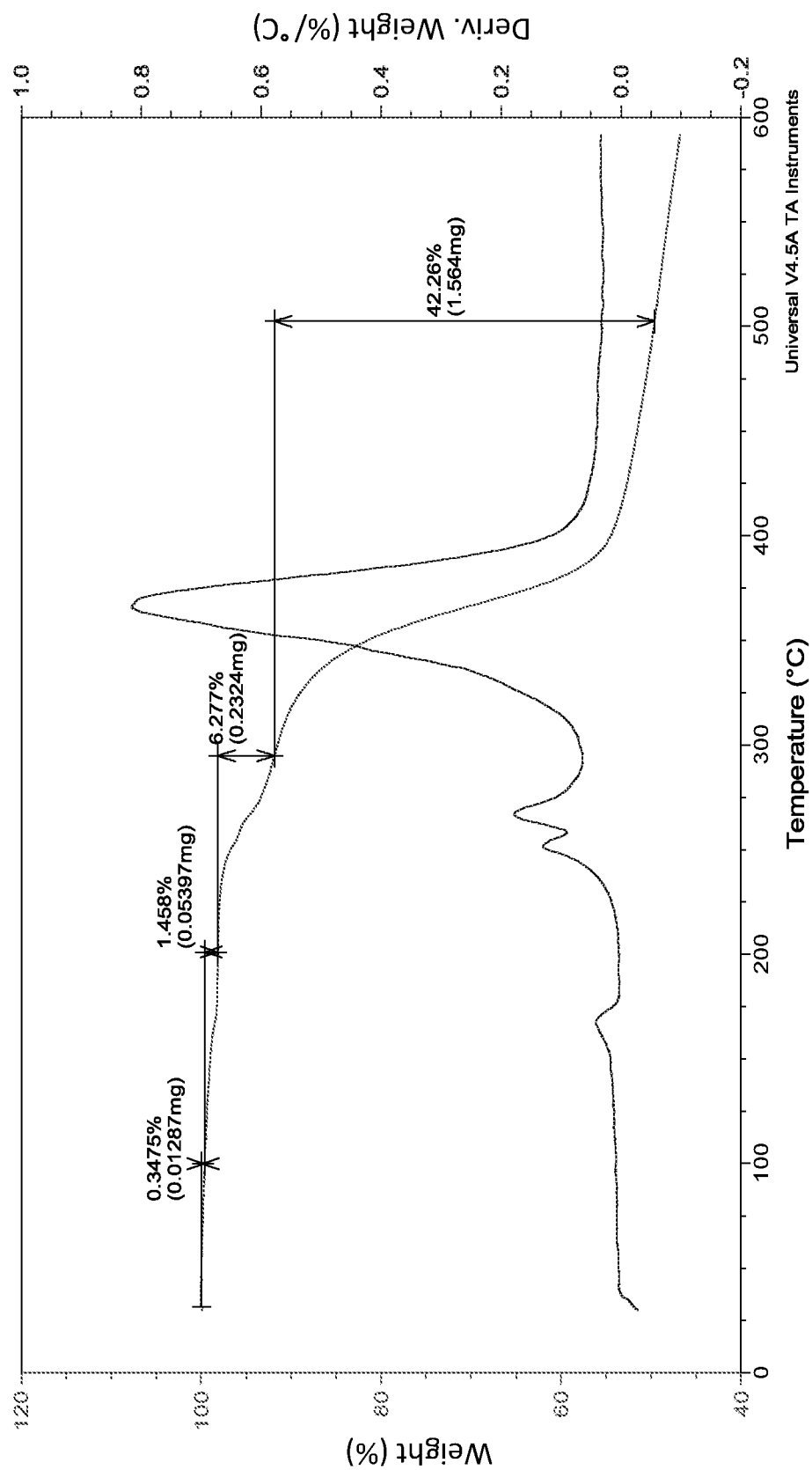
FIG. 6 shows TGA data representative of Compound II phosphoric acid salt.

In some embodiments, the phosphoric acid salt of the compound of Formula II has a DSC thermogram having an endothermic peak at about 257.2° C. In some embodiments, the phosphoric acid salt of the compound of Formula II has a DSC thermogram substantially as shown in FIG. 5. In some embodiments, the phosphoric acid salt of the compound of Formula II has a TGA thermogram substantially as shown in FIG. 6.

In some embodiments, the present application provides N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide maleic salt (also referred to herein as maleate salt of the compound of Formula II, mealeate salt of Compound II, Compound II maleate salt, or any variation thereof).

In some embodiments, the salt is a 1:1 stoichiometric ratio of N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide to maleic acid.

In some embodiments, the maleic acid salt of the compound of Formula II is crystalline.

In some embodiments, the maleic acid salt of the compound of Formula II is substantially isolated.

In some embodiments, the maleic acid salt of the compound of Formula II has at least one XRPD peak, in terms of 2-theta, selected from about 4.5°, about 6.5°, about 14.1°, about 24.0°, and about 28.2°. In some embodiments, the maleic acid salt of the compound of Formula II has at least two XRPD peaks, in terms of 2-theta, selected from about 4.5°, about 6.5°, about 14.1°, about 24.0°, and about 28.2°. In some embodiments, the maleic acid salt of the compound of Formula II has at least three XRPD peaks, in terms of 2-theta, selected from about 4.5°, about 6.5°, about 14.1°, about 24.0°, and about 28.2°. In some embodiments, the maleic acid salt of the compound of Formula II has at least four XRPD peaks, in terms of 2-theta, selected from about 4.5°, about 6.5°, about 14.1°, about 24.0°, and about 28.2°. In some embodiments, the maleic acid salt of the compound of Formula II comprises the following XRPD peaks, in terms of 2-theta: about 4.5°, about 6.5°, about 14.1°, about 24.0°, and about 28.2°.

Figure 7:
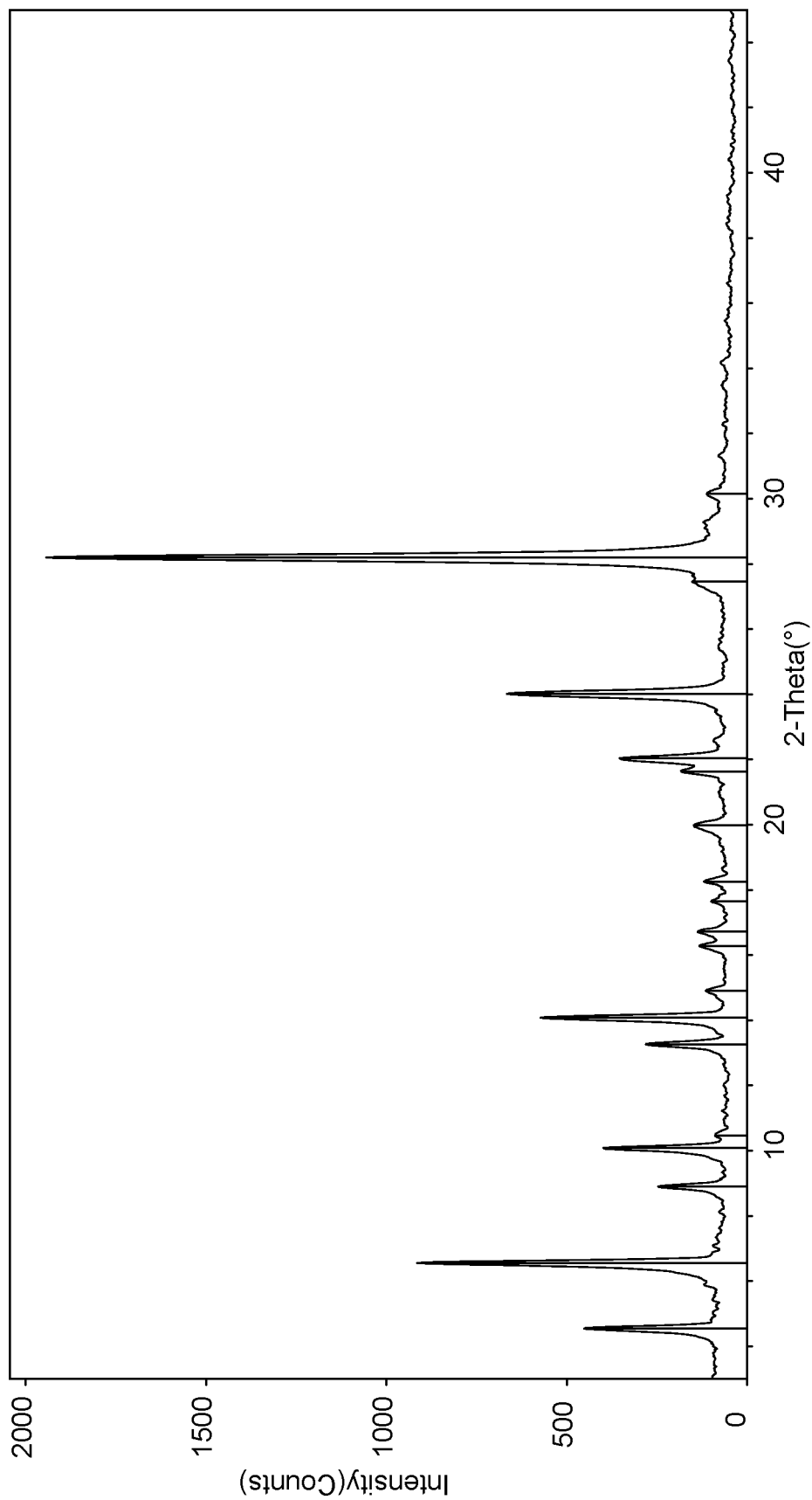
FIG. 7 shows an XRPD pattern representative of Compound II maleic acid salt.

In some embodiments, the maleic acid salt of the compound of Formula II has an XRPD profile substantially as shown in FIG. 7.

Figure 8:
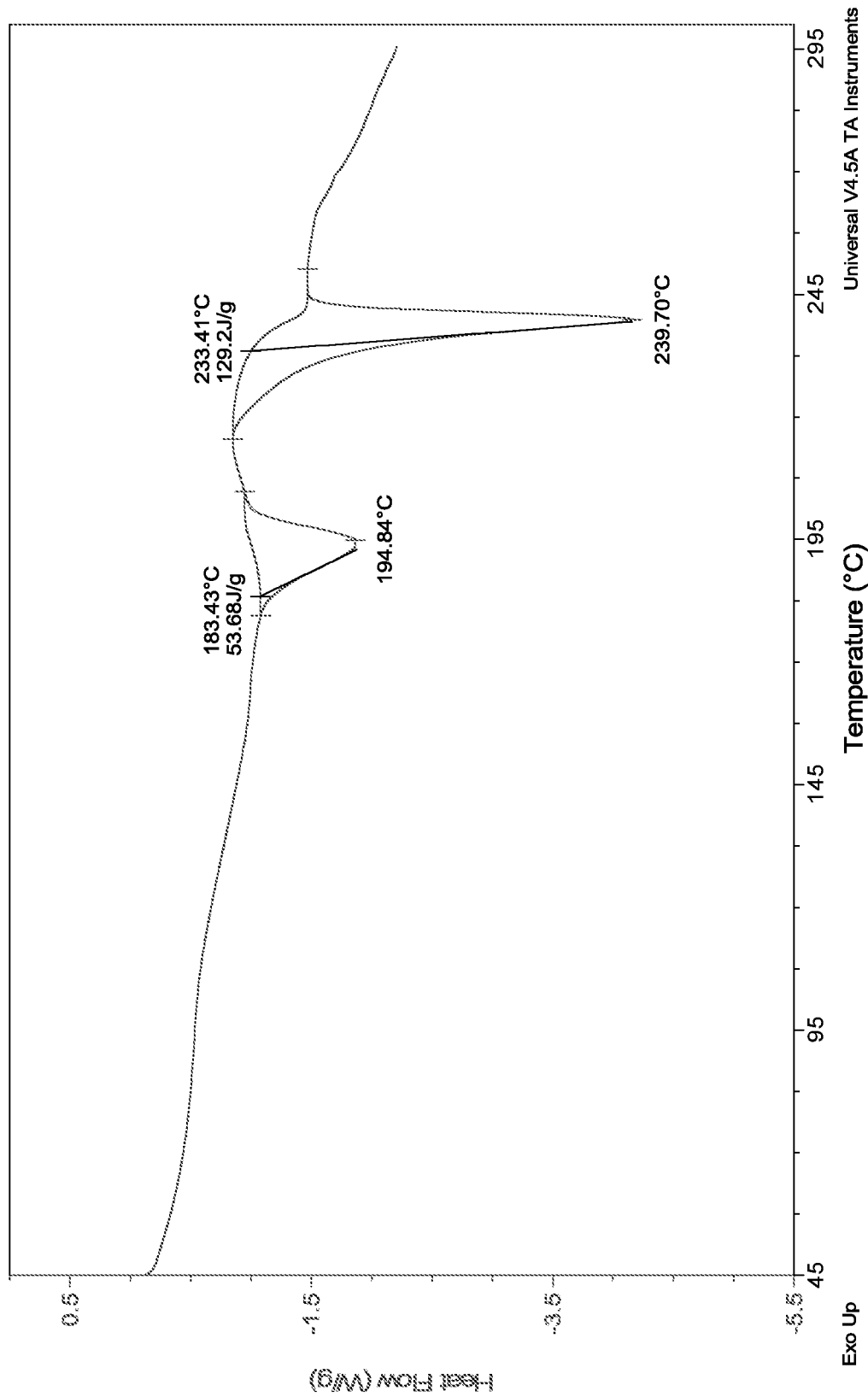
FIG. 8 shows a DSC thermogram representative of Compound II maleic acid salt.
Figure 9:
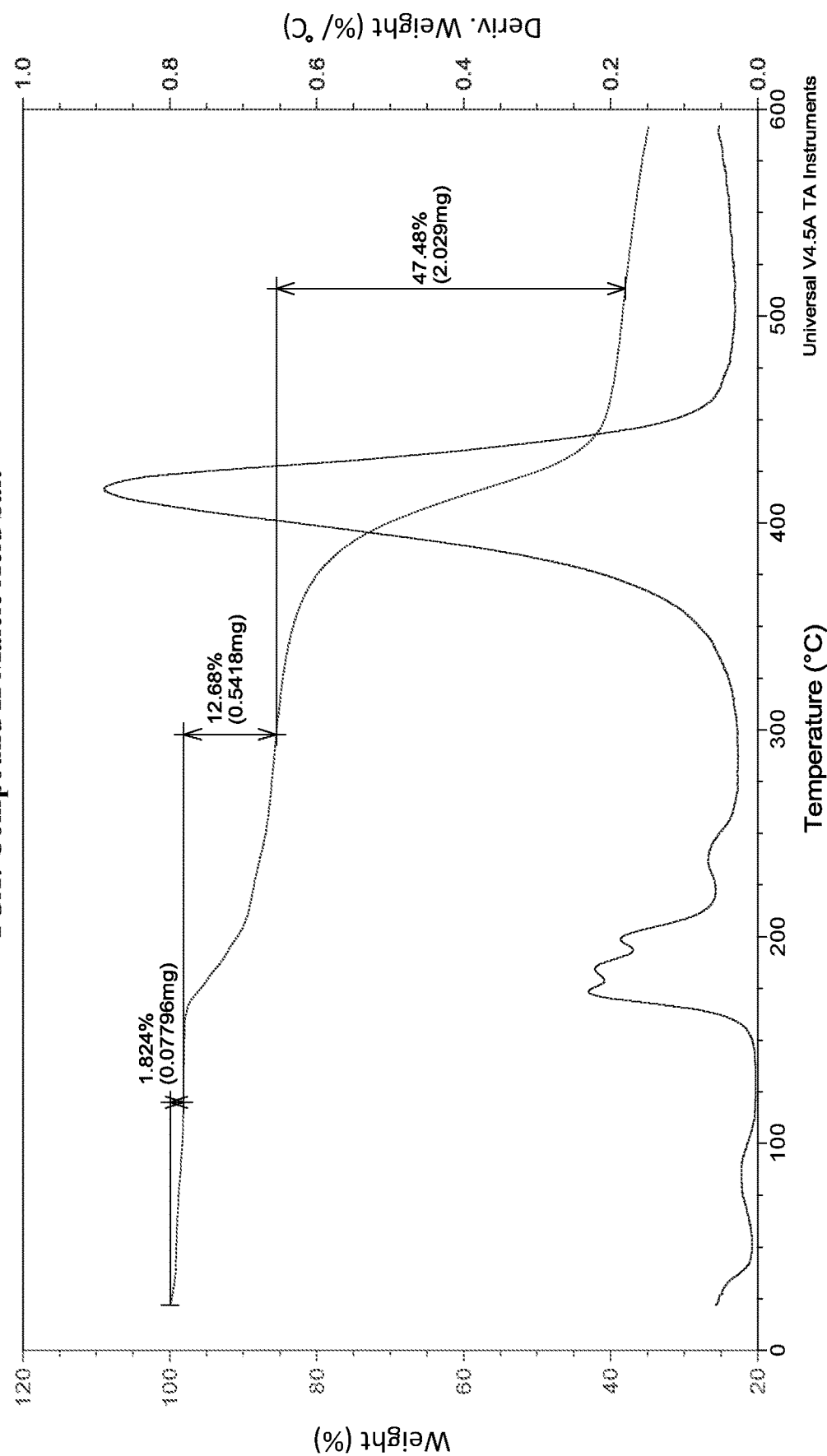
FIG. 9 shows TGA data representative of Compound II maleic acid salt.

In some embodiments, the maleic acid salt of the compound of Formula II has a DSC thermogram having an endothermic peak at about 194.8° C. and/or about 239.7° C. In some embodiments, the maleic acid salt of the compound of Formula II has a DSC thermogram substantially as shown in FIG. 8. In some embodiments, the maleic acid salt of the compound of Formula II has a TGA thermogram substantially as shown in FIG. 9.

In some embodiments, the present application provides N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide hemi-sulfuric acid salt (also referred to herein as hemi-sulfate salt of the compound of Formula II, hemi-sulfate salt of Compound II, Compound II hemi-sulfate salt, or any variation thereof).

In some embodiments, the salt is a 1:0.5 (i.e., 2:1) stoichiometric ratio of N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide to sulfuric acid.

In some embodiments, the hemi-sulfuric acid salt of the compound of Formula II is crystalline.

In some embodiments, the hemi-sulfuric acid salt of the compound of Formula II is substantially isolated.

In some embodiments, the hemi-sulfuric acid salt of the compound of Formula II has at least one XRPD peak, in terms of 2-theta, selected from about 5.3°, about 8.5°, about 15.3°, about 20.1°, and about 24.9°. In some embodiments, the hemi-sulfuric acid salt of the compound of Formula II has at least two XRPD peaks, in terms of 2-theta, selected from about 5.3°, about 8.5°, about 15.3°, about 20.1°, and about 24.9°. In some embodiments, the hemi-sulfuric acid salt of the compound of Formula II has at least three XRPD peaks, in terms of 2-theta, selected from about 5.3°, about 8.5°, about 15.3°, about 20.1°, and about 24.9°. In some embodiments, the hemi-sulfuric acid salt of the compound of Formula II has at least four XRPD peaks, in terms of 2-theta, selected from about 5.3°, about 8.5°, about 15.3°, about 20.1°, and about 24.9°. In some embodiments, the hemi-sulfuric acid salt of the compound of Formula II comprises the following XRPD peaks, in terms of 2-theta: about 5.3°, about 8.5°, about 15.3°, about 20.1°, and about 24.9°.

Figure 10:
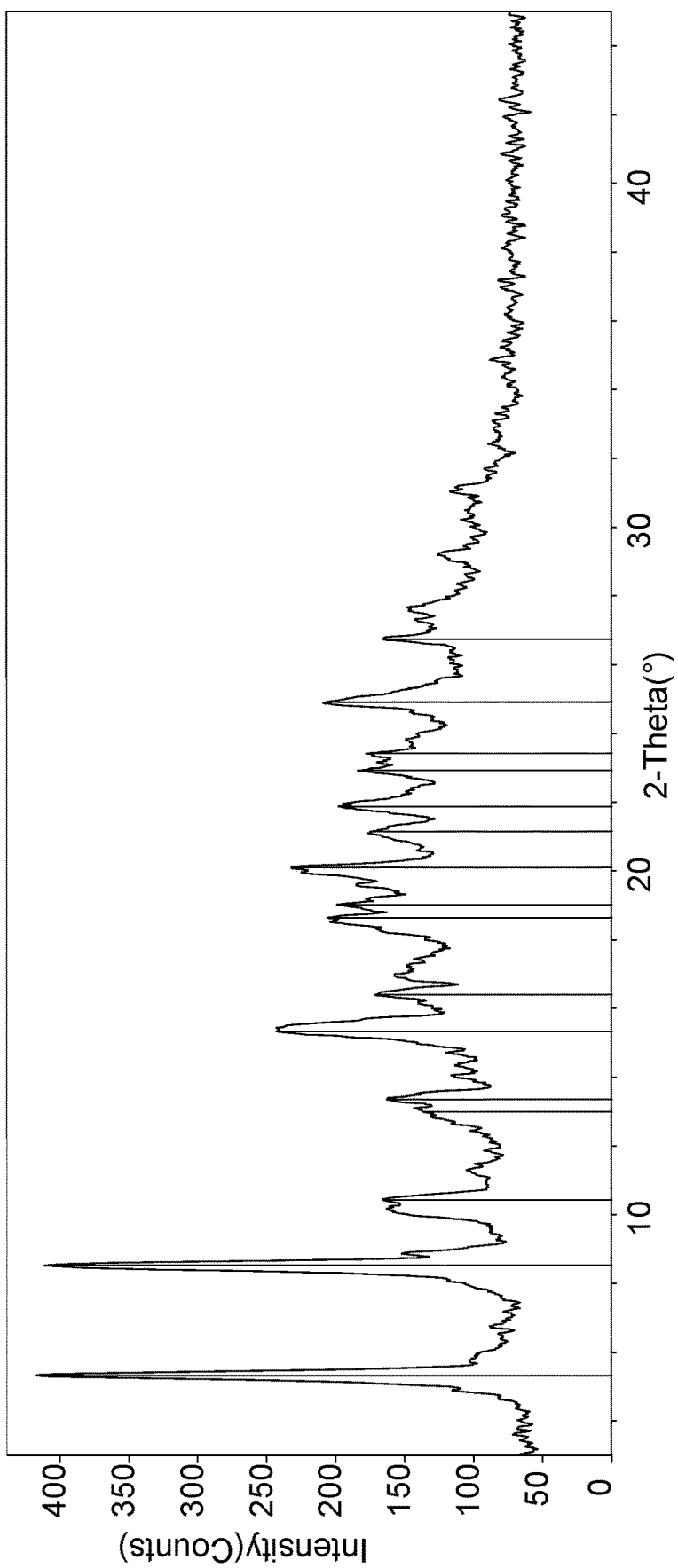
FIG. 10 shows an XRPD pattern representative of Compound II hemi-sulfuric acid salt.

In some embodiments, the hemi-sulfuric acid salt of the compound of Formula II has an XRPD profile substantially as shown in FIG. 10.

Figure 11:
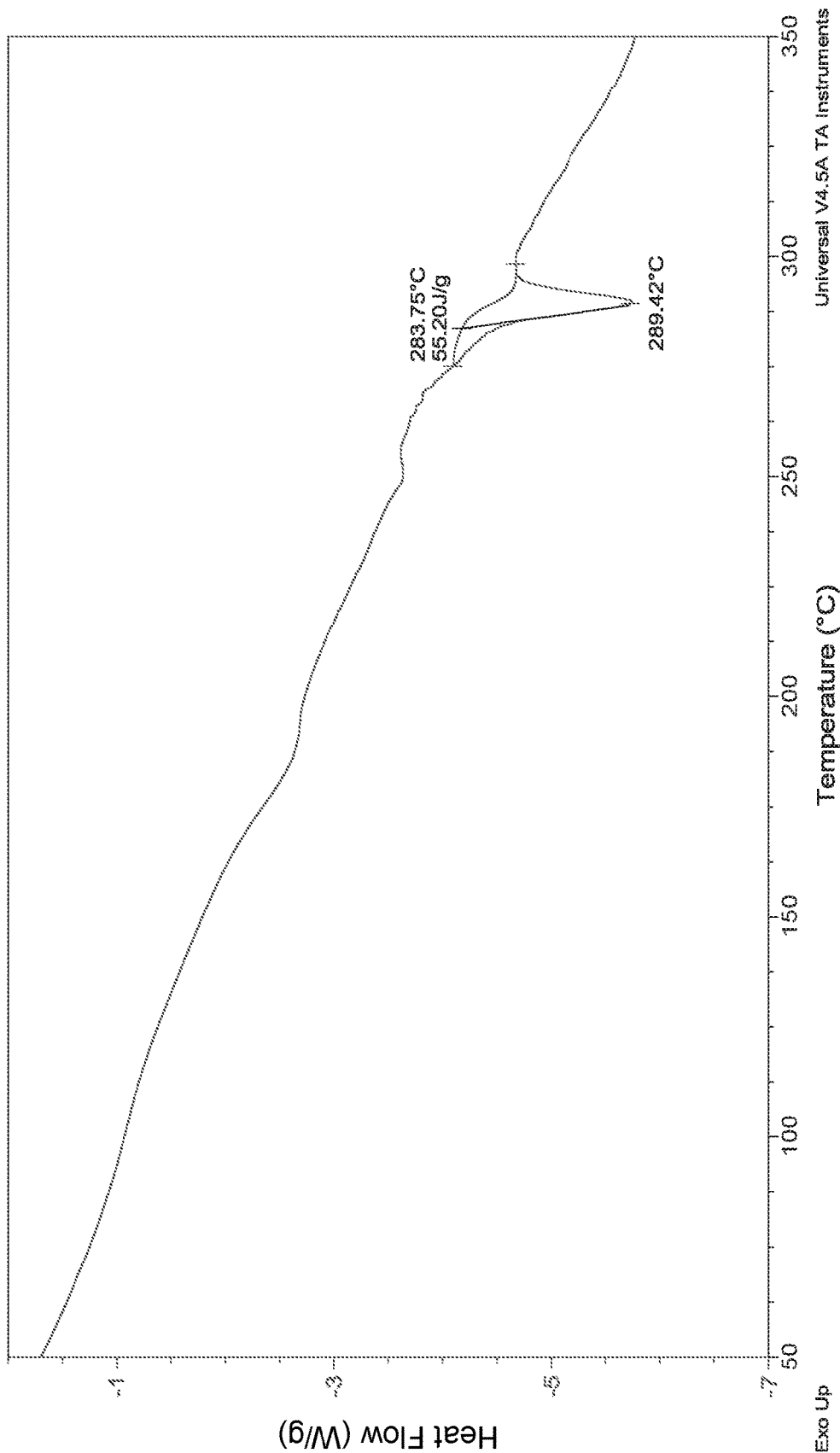
FIG. 11 shows a DSC thermogram representative of Compound II hemi-sulfuric acid salt.
Figure 12:
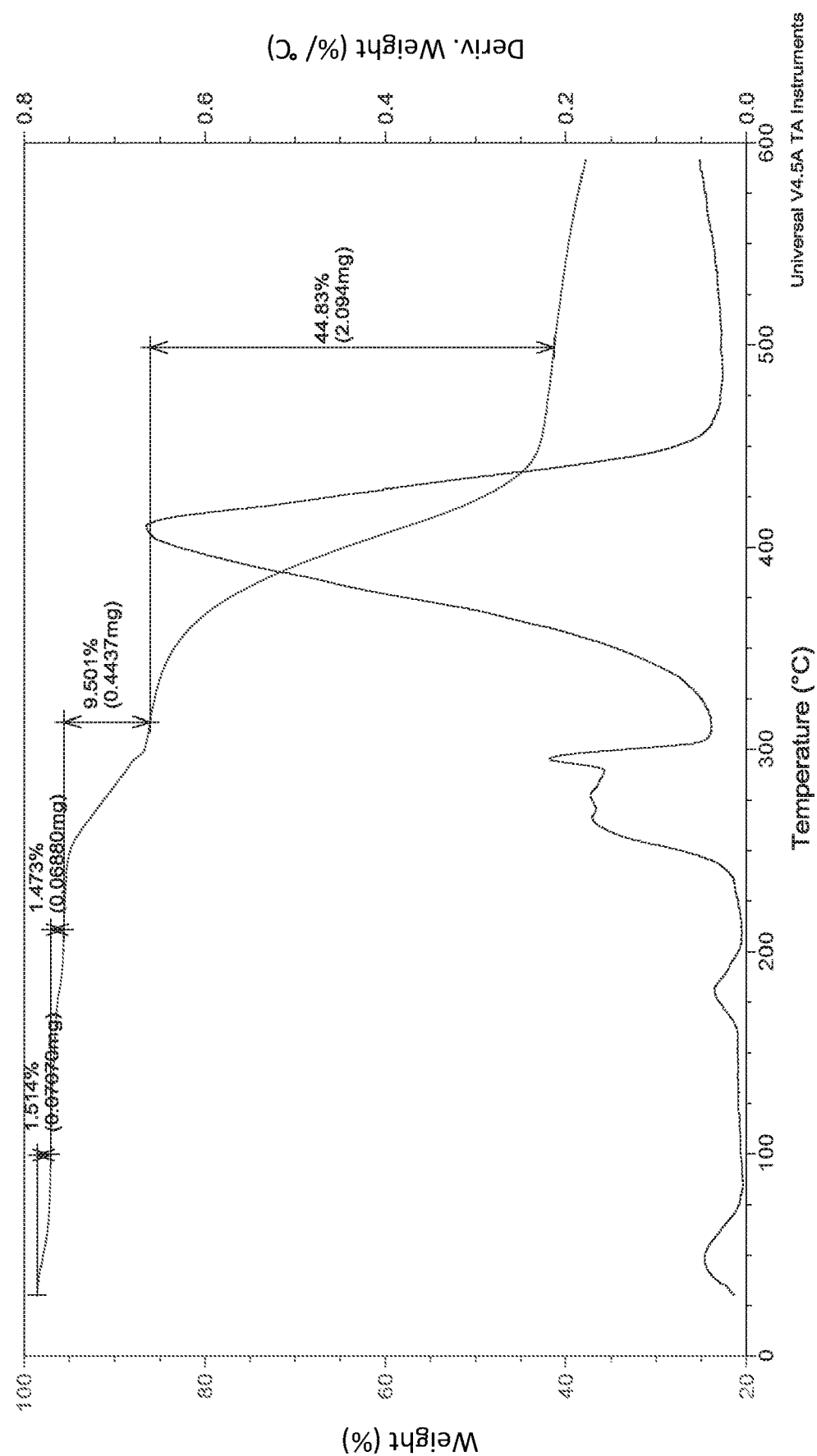
FIG. 12 shows TGA data representative of Compound II hemi-sulfuric acid salt.

In some embodiments, the hemi-sulfuric acid salt of the compound of Formula II has a DSC thermogram having an endothermic peak at about 289.4° C. In some embodiments, the hemi-sulfuric acid salt of the compound of Formula II has a DSC thermogram substantially as shown in FIG. 11. In some embodiments, the hemi-sulfuric acid salt of the compound of Formula II has a TGA thermogram substantially as shown in FIG. 12.

In some embodiments, the present application provides N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide hydrochloric acid salt (also referred to herein as hydrochloride salt of the compound of Formula II, hydrochloride salt of Compound II, Compound II hydrochloride salt, or any variation thereof).

In some embodiments, the salt is a 1:1 stoichiometric ratio of N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide to hydrochloric acid.

In some embodiments, the hydrochloric acid salt of the compound of Formula II is crystalline.

In some embodiments, the hydrochloric acid salt of the compound of Formula II is substantially isolated.

In some embodiments, the hydrochloric acid salt of the compound of Formula II has at least one XRPD peak, in terms of 2-theta, selected from about 6.5°, about 9.7°, about 14.9°, about 21.5°, and about 23.9°. In some embodiments, the hydrochloric acid salt of the compound of Formula II has at least two XRPD peaks, in terms of 2-theta, selected from about 6.5°, about 9.7°, about 14.9°, about 21.5°, and about 23.9°. In some embodiments, the hydrochloric acid salt of the compound of Formula II has at least three XRPD peaks, in terms of 2-theta, selected from about 6.5°, about 9.7°, about 14.9°, about 21.5°, and about 23.9°. In some embodiments, the hydrochloric acid salt of the compound of Formula II has at least four XRPD peaks, in terms of 2-theta, selected from about 6.5°, about 9.7°, about 14.9°, about 21.5°, and about 23.9°. In some embodiments, the hydrochloric acid salt of the compound of Formula II comprises the following XRPD peaks, in terms of 2-theta: about 6.5°, about 9.7°, about 14.9°, about 21.5°, and about 23.9°.

Figure 13:
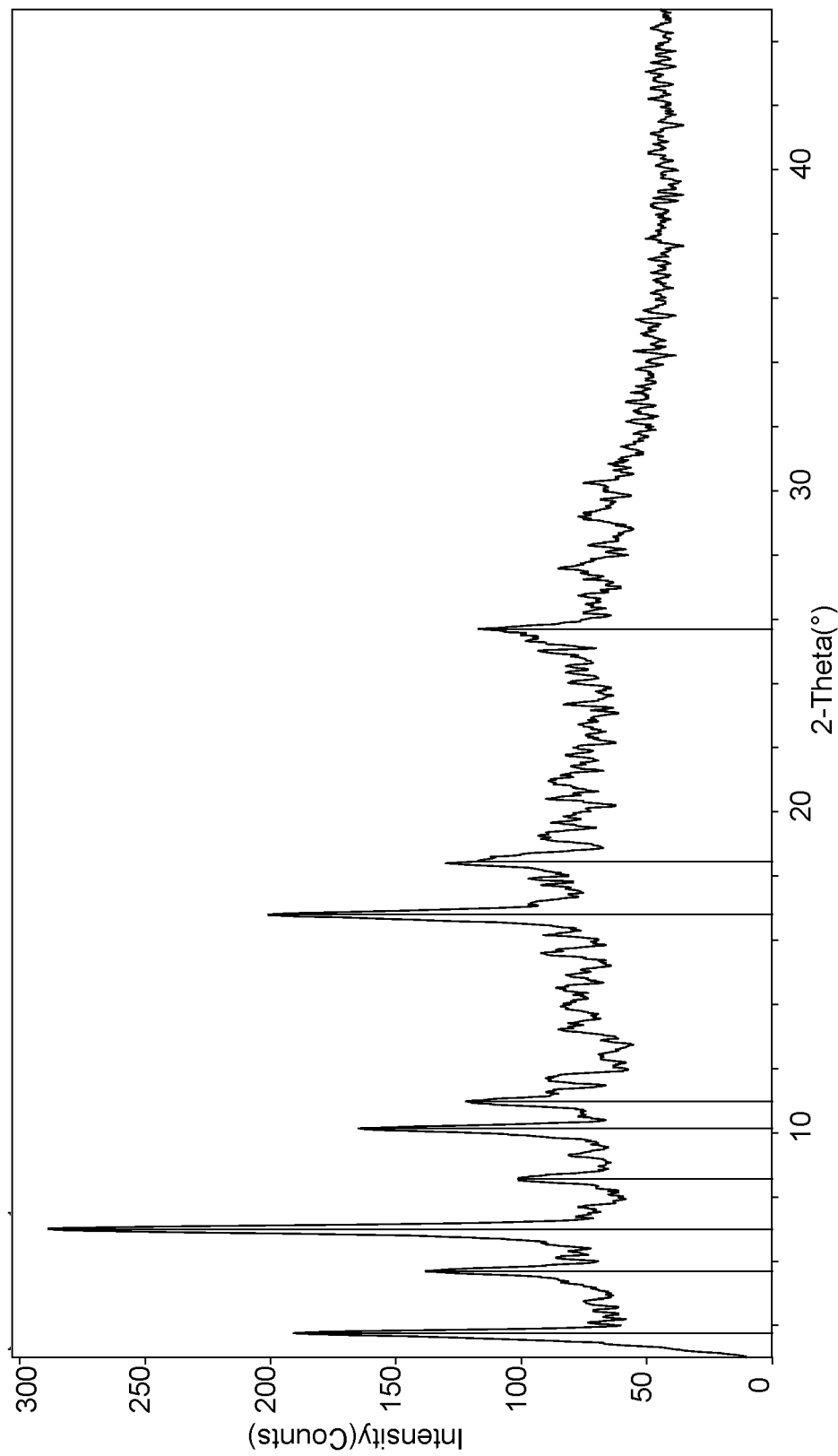
FIG. 13 shows an XRPD pattern representative of Compound II hydrochloric acid salt.

In some embodiments, the hydrochloric acid salt of the compound of Formula II has an XRPD profile substantially as shown in FIG. 13.

Figure 14:
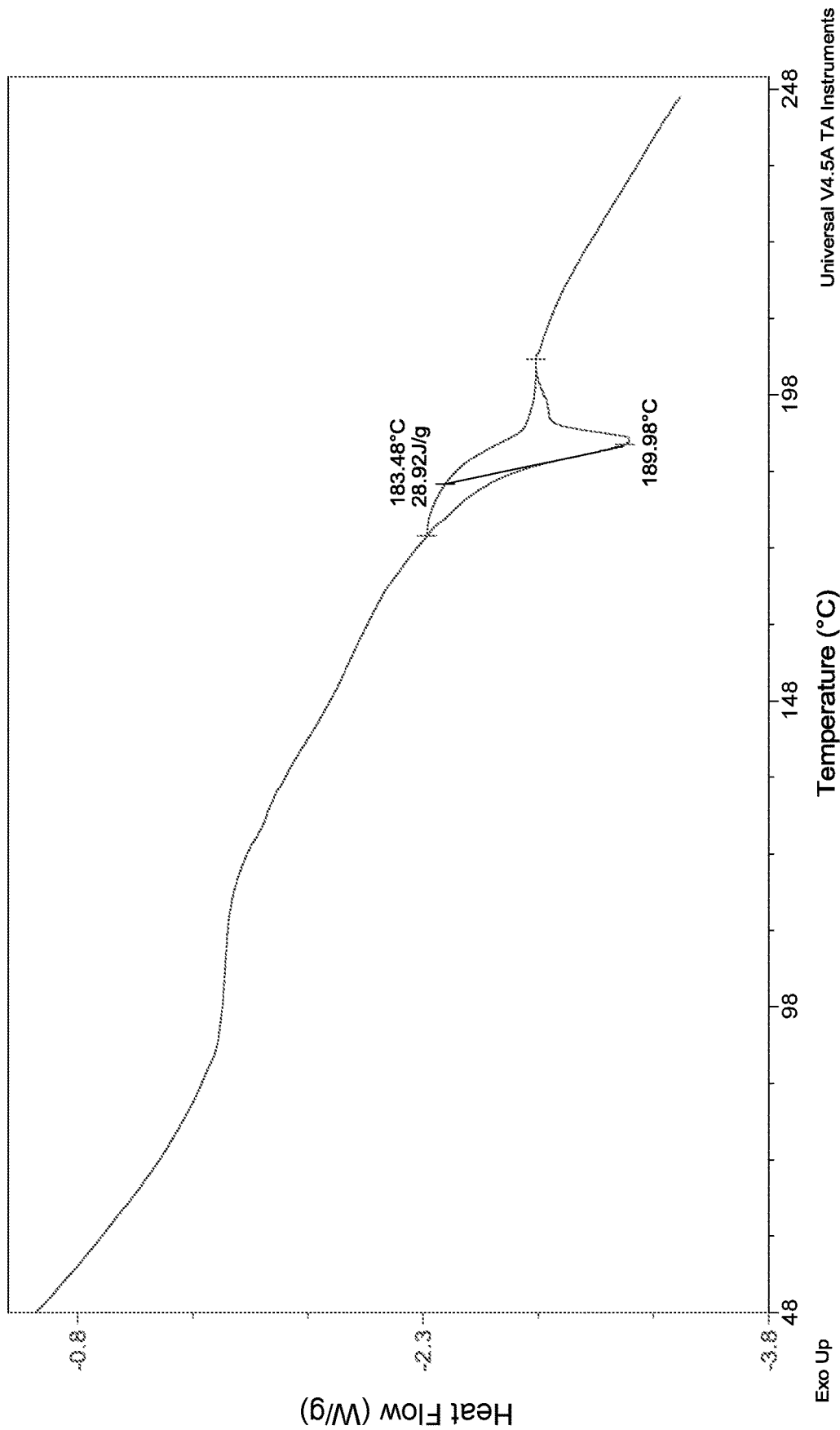
FIG. 14 shows a DSC thermogram representative of Compound II hydrochloric acid salt.
Figure 15:
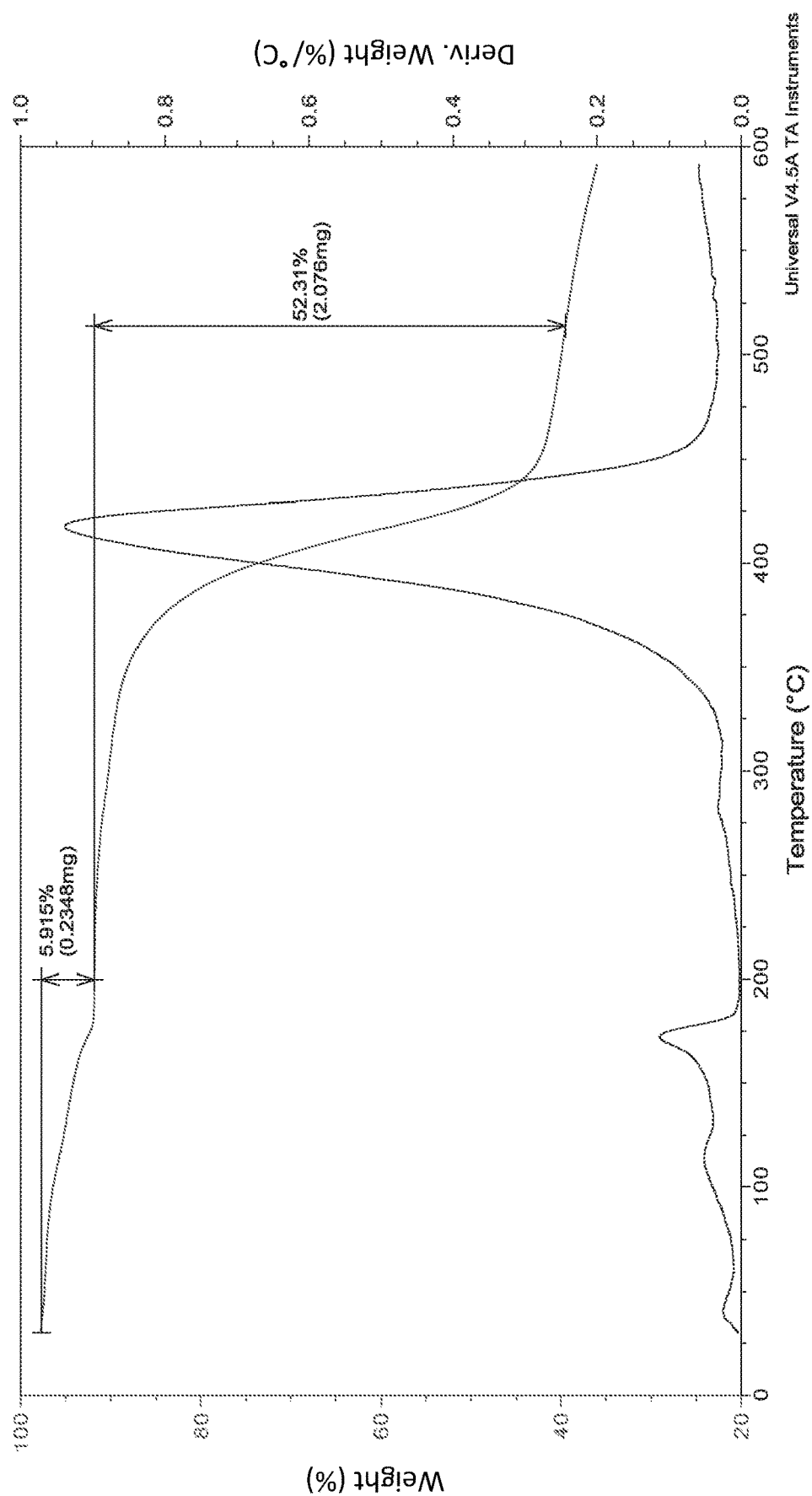
FIG. 15 shows TGA data representative of Compound II hydrochloric acid salt.

In some embodiments, the hydrochloric acid salt of the compound of Formula II has a DSC thermogram having an endothermic peak at about 190° C. In some embodiments, the hydrochloric acid salt of the compound of Formula II has a DSC thermogram substantially as shown in FIG. 14. In some embodiments, the hydrochloric acid salt of the compound of Formula II has a TGA thermogram substantially as shown in FIG. 15.

In some embodiments, the present application provides N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide salicylic acid salt (also referred to herein as salicylate salt of the compound of Formula II, salicylate salt of Compound II, Compound II salicylate salt, or any variation thereof).

In some embodiments, the salt is a 1:1 stoichiometric ratio of N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide to salicylic acid.

In some embodiments, the salicylic acid salt of the compound of Formula II is crystalline.

In some embodiments, the salicylic acid salt of the compound of Formula II is substantially isolated.

In some embodiments, the salicylic acid salt of the compound of Formula II has at least one XRPD peak, in terms of 2-theta, selected from about 7.3°, about 14.4°, about 15.7°, about 19.9°, and about 21.9°. In some embodiments, the salicylic acid salt of the compound of Formula II has at least two XRPD peaks, in terms of 2-theta, selected from about 7.3°, about 14.4°, about 15.7°, about 19.9°, and about 21.9°. In some embodiments, the salicylic acid salt of the compound of Formula II has at least three XRPD peaks, in terms of 2-theta, selected from about 7.3°, about 14.4°, about 15.7°, about 19.9°, and about 21.9°. In some embodiments, the salicylic acid salt of the compound of Formula II has at least four XRPD peaks, in terms of 2-theta, selected from about 7.3°, about 14.4°, about 15.7°, about 19.9°, and about 21.9°. In some embodiments, the salicylic acid salt of the compound of Formula II comprises the following XRPD peaks, in terms of 2-theta: about 7.3°, about 14.4°, about 15.7°, about 19.9°, and about 21.9°.

Figure 16:
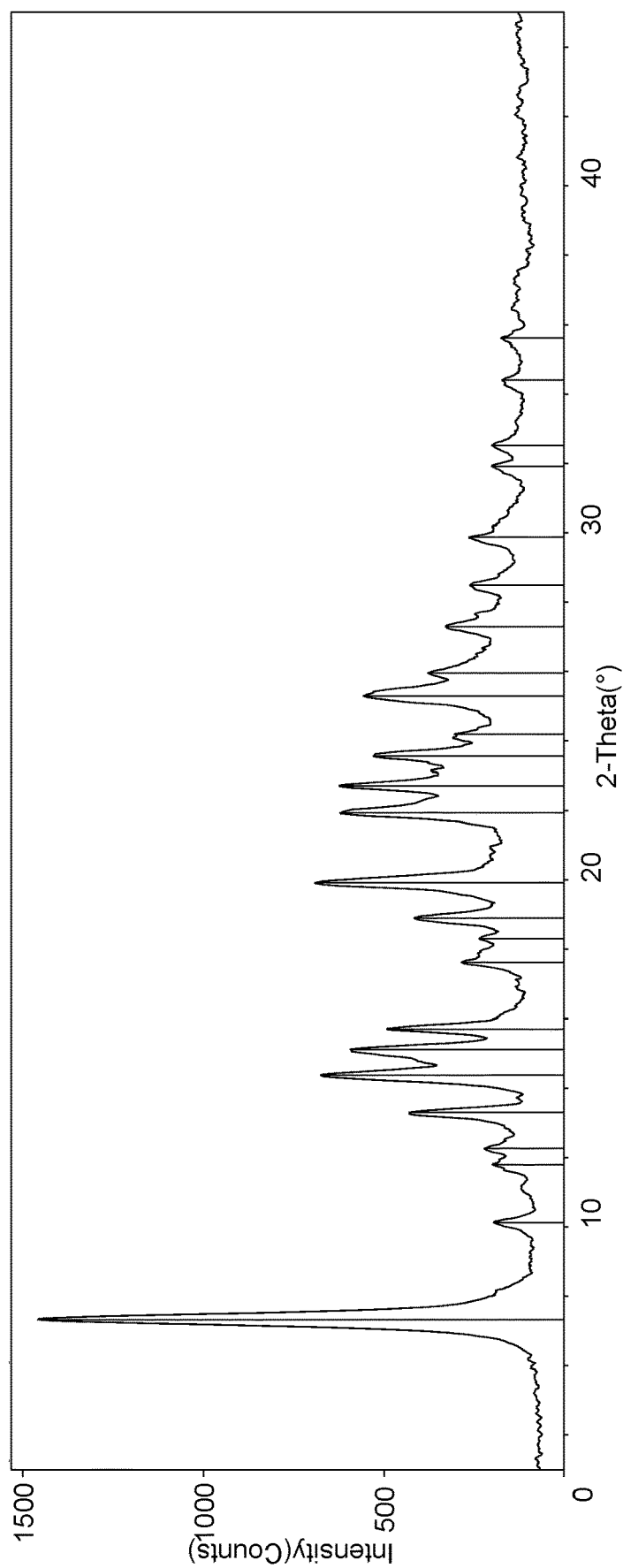
FIG. 16 shows an XRPD pattern representative of Compound II salicylic acid salt.

In some embodiments, the salicylic acid salt of the compound of Formula II has an XRPD profile substantially as shown in FIG. 16.

Figure 17:
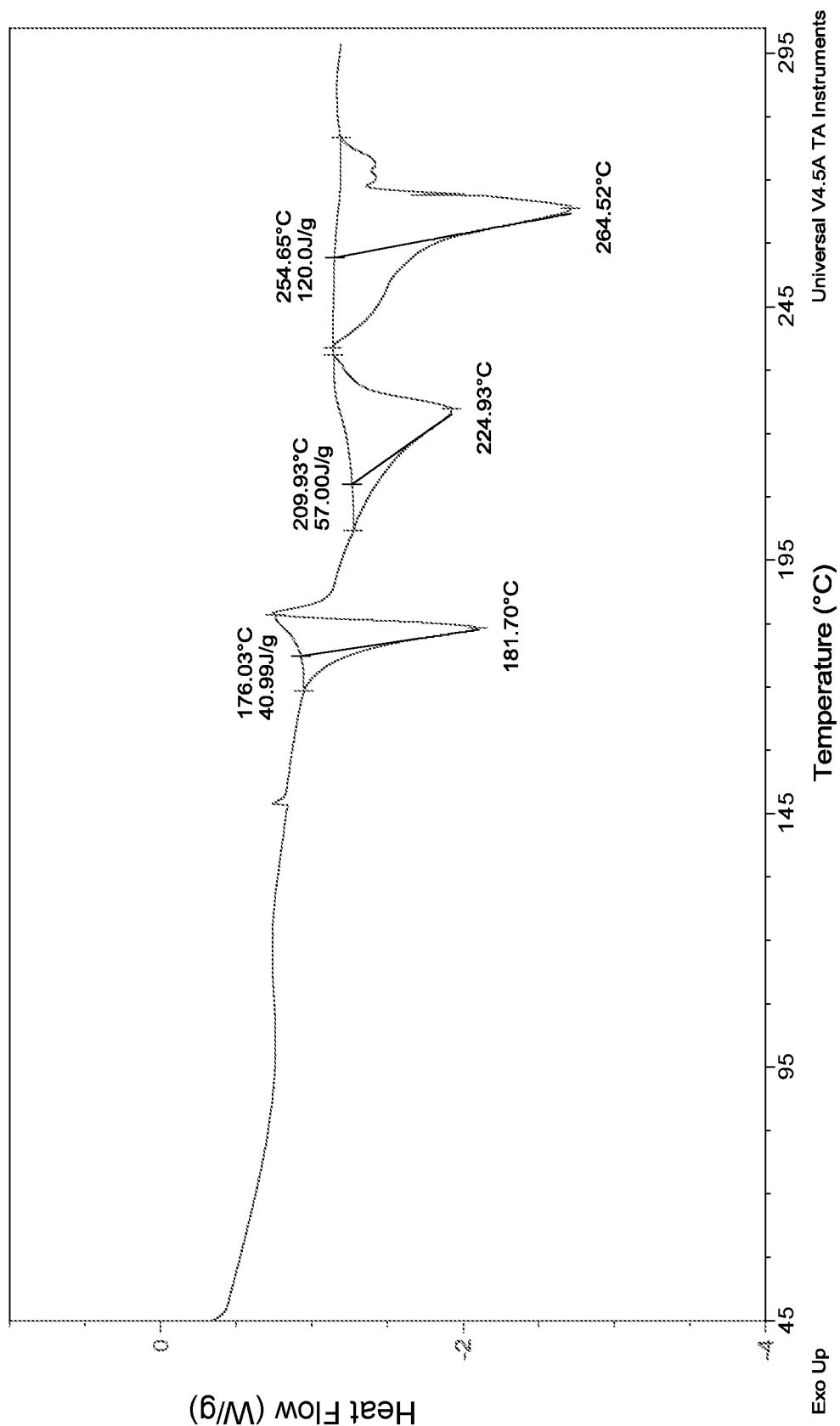
FIG. 17 shows a DSC thermogram representative of Compound II salicylic acid salt.
Figure 18:
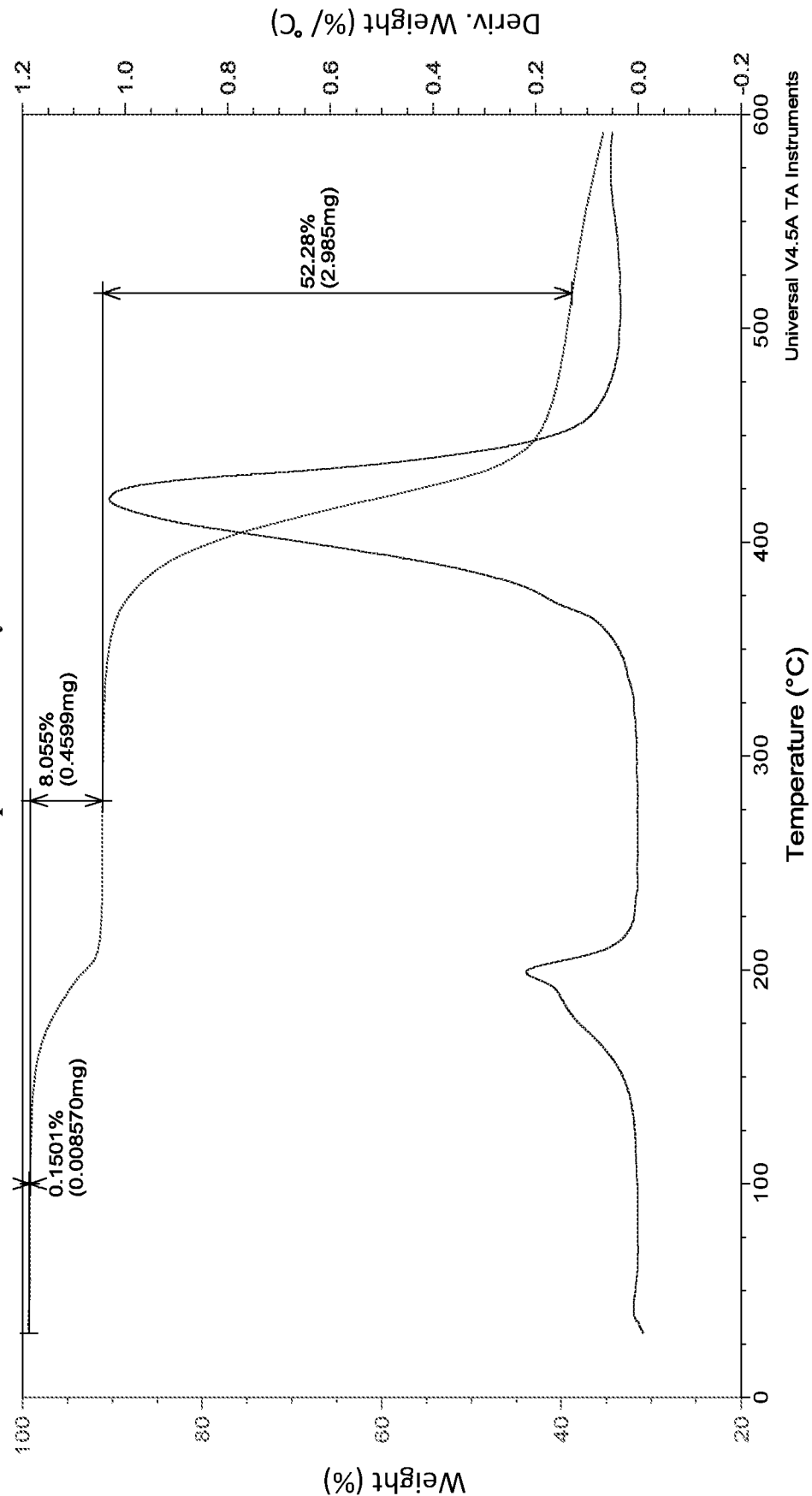
FIG. 18 shows TGA data representative of Compound II salicylic acid salt.

In some embodiments, the salicylic acid salt of the compound of Formula II has a DSC thermogram having an endothermic peak at about 181.7° C., about 224.9° C., and/or 264.5° C. In some embodiments, the salicylic acid salt of the compound of Formula II has a DSC thermogram substantially as shown in FIG. 17. In some embodiments, the salicylic acid salt of the compound of Formula II has a TGA thermogram substantially as shown in FIG. 18.

In some embodiments, the present application provides N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide methanesulfonic acid salt (also referred to herein as mesylate salt of the compound of Formula II, mesylate salt of Compound II, Compound II mesylate salt, or any variation thereof).

In some embodiments, the salt is a 1:1 stoichiometric ratio of N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide to methanesulfonic acid.

In some embodiments, the methanesulfonic acid salt of the compound of Formula II is crystalline.

In some embodiments, the methanesulfonic acid salt of the compound of Formula II is substantially isolated.

In some embodiments, the methanesulfonic acid salt of the compound of Formula II has at least one XRPD peak, in terms of 2-theta, selected from about 5.0°, about 8.2°, about 13.2°, and about 16.9°. In some embodiments, the methanesulfonic acid salt of the compound of Formula II has at least two XRPD peaks, in terms of 2-theta, selected from about 5.0°, about 8.2°, about 13.2°, and about 16.9°. In some embodiments, the methanesulfonic acid salt of the compound of Formula II has at least three XRPD peaks, in terms of 2-theta, selected from about 5.0°, about 8.2°, about 13.2°, and about 16.9°. In some embodiments, the methanesulfonic acid salt of the compound of Formula II comprises the following XRPD peaks, in terms of 2-theta: about 5.0°, about 8.2°, about 13.2°, and about 16.9°.

Figure 19:
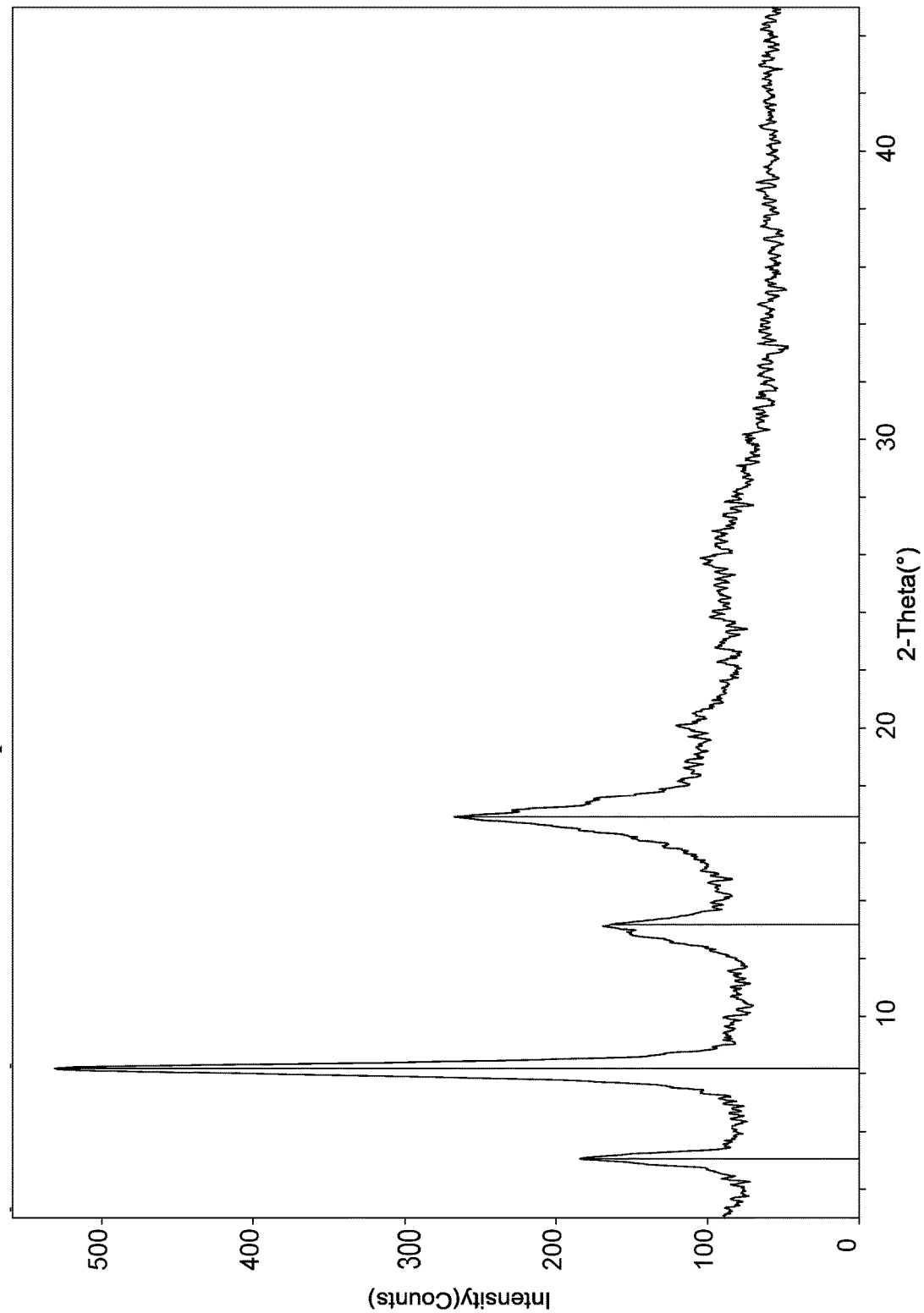
FIG. 19 shows an XRPD pattern representative of Compound II methanesulfonic acid salt.

In some embodiments, the methanesulfonic acid salt of the compound of Formula II has an XRPD profile substantially as shown in FIG. 19.

Figure 20:
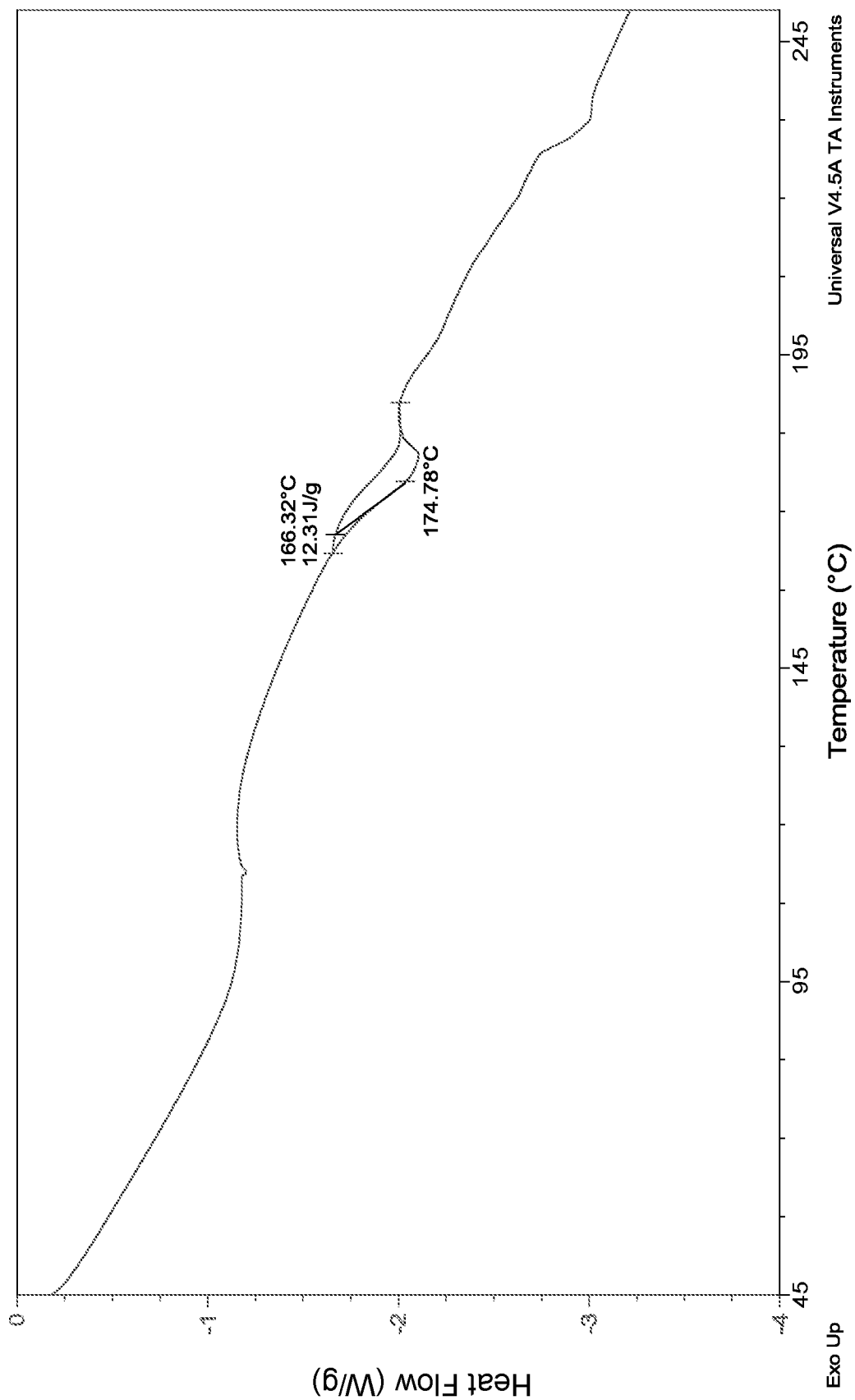
FIG. 20 shows a DSC thermogram representative of Compound II methanesulfonic acid salt.
Figure 21:
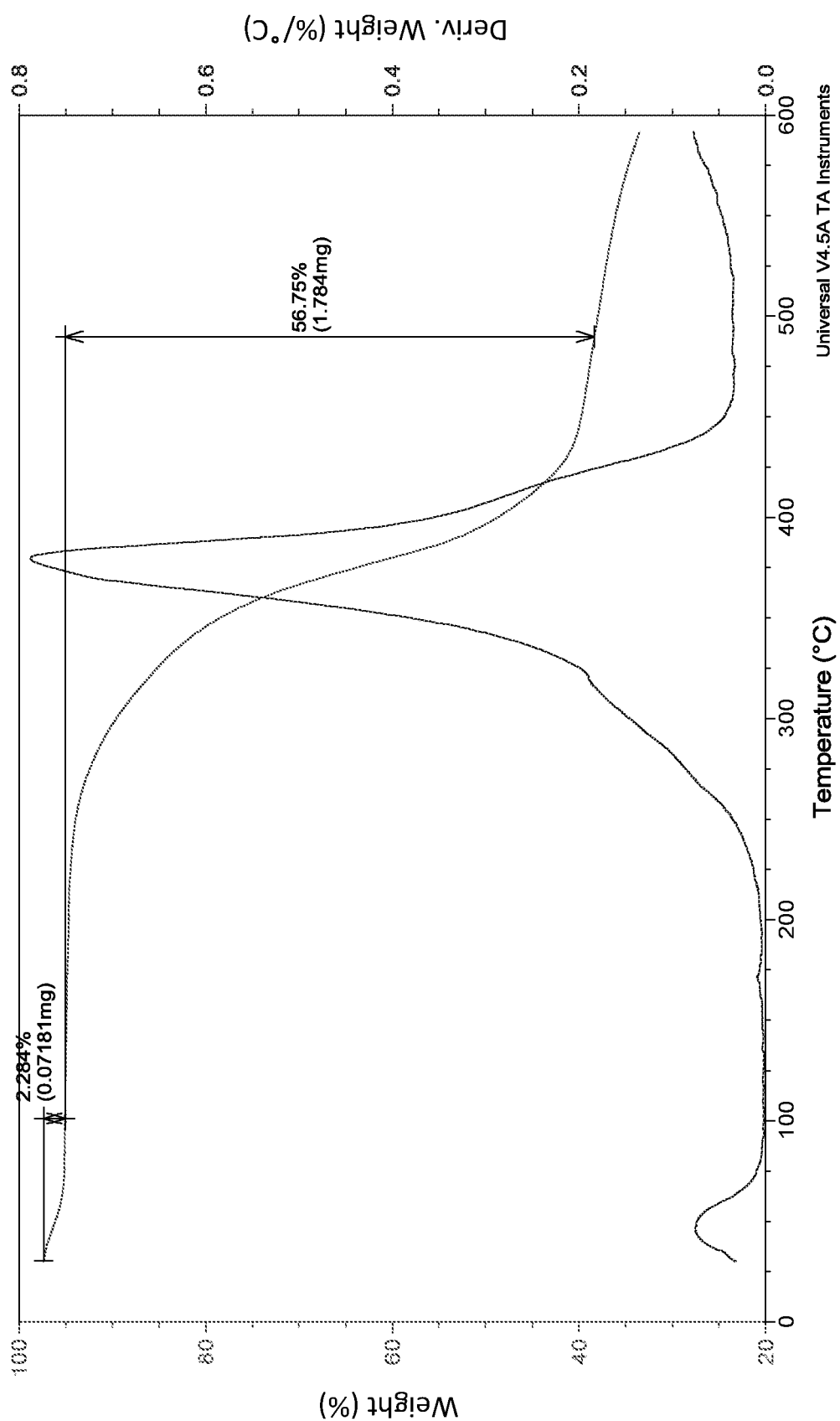
FIG. 21 shows TGA data representative of Compound II methanesulfonic acid salt.

In some embodiments, the methanesulfonic acid salt of the compound of Formula II has a DSC thermogram having an endothermic peak at about 174.8° C. In some embodiments, the methanesulfonic acid salt of the compound of Formula II has a DSC thermogram substantially as shown in FIG. 20. In some embodiments, the methanesulfonic acid salt of the compound of Formula II has a TGA thermogram substantially as shown in FIG. 21.

In some embodiments, the present application provides N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide ethanesulfonic acid salt (also referred to herein as esylate salt of the compound of Formula II, esylate salt of Compound II, Compound II esylate salt, or any variation thereof).

In some embodiments, the salt is a 1:1 stoichiometric ratio of N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide to ethanesulfonic acid.

In some embodiments, the ethanesulfonic acid salt of the compound of Formula II is crystalline.

In some embodiments, the ethanesulfonic acid salt of the compound of Formula II is substantially isolated.

In some embodiments, the ethanesulfonic acid salt of the compound of Formula II has at least one XRPD peak, in terms of 2-theta, selected from about 4.9°, about 7.6°, about 15.4°, about 16.8°, and about 17.5°. In some embodiments, the ethanesulfonic acid salt of the compound of Formula II has at least two XRPD peaks, in terms of 2-theta, selected from about 4.9°, about 7.6°, about 15.4°, about 16.8°, and about 17.5°. In some embodiments, the ethanesulfonic acid salt of the compound of Formula II has at least three XRPD peaks, in terms of 2-theta, selected from about 4.9°, about 7.6°, about 15.4°, about 16.8°, and about 17.5°. In some embodiments, the ethanesulfonic acid salt of the compound of Formula II has at least four XRPD peaks, in terms of 2-theta, selected from about 4.9°, about 7.6°, about 15.4°, about 16.8°, and about 17.5°. In some embodiments, the ethanesulfonic acid salt of the compound of Formula II comprises the following XRPD peaks, in terms of 2-theta: about 4.9°, about 7.6°, about 15.4°, about 16.8°, and about 17.5°. In some embodiments, the ethanesulfonic acid salt of the compound of Formula II comprises the following XRPD peaks, in terms of 2-theta: about 4.9°, about 7.6°, about 15.4°, and about 17.5°.

Figure 22:
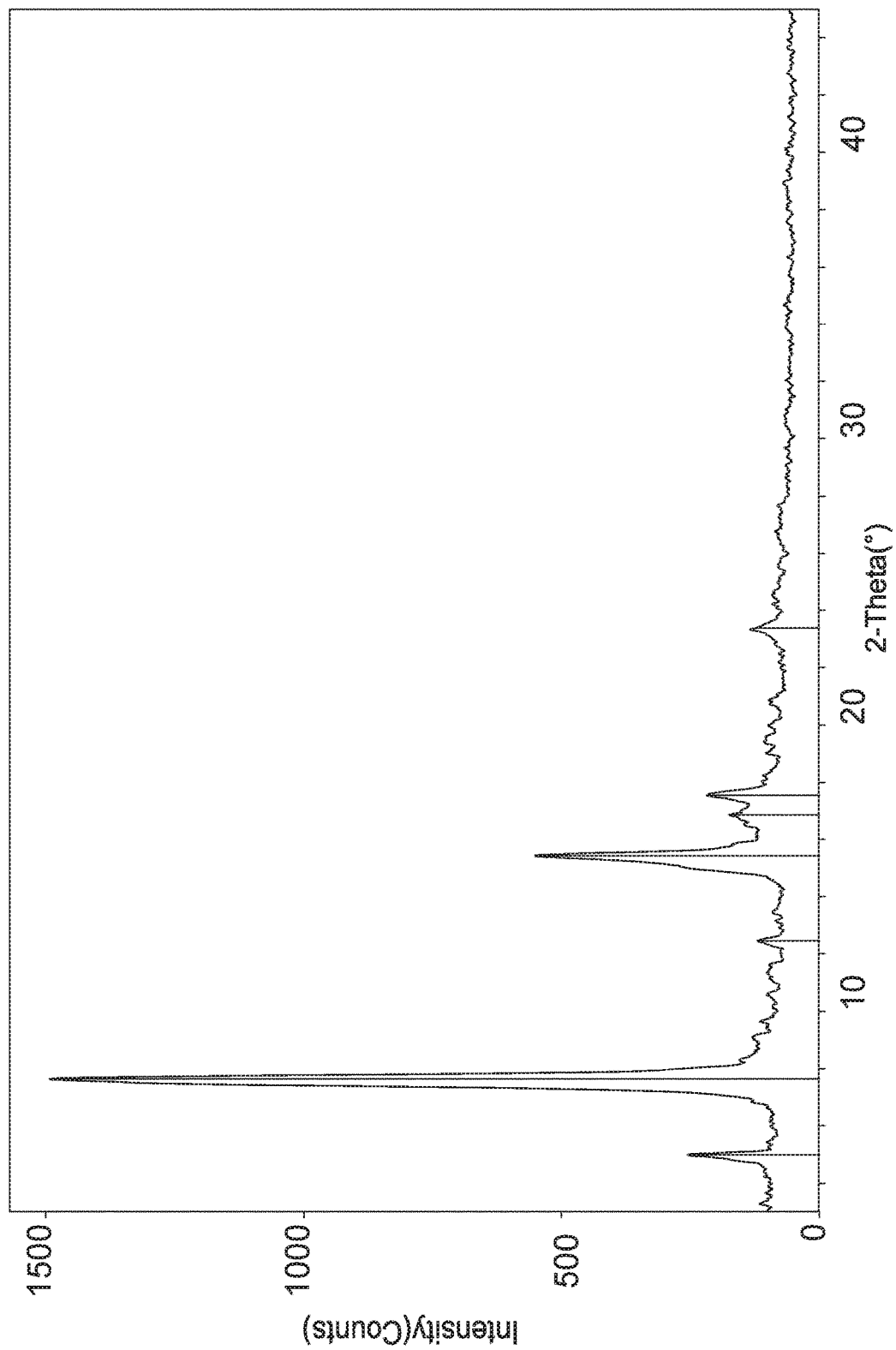
FIG. 22 shows an XRPD pattern representative of Compound II ethanesulfonic acid salt.

In some embodiments, the ethanesulfonic acid salt of the compound of Formula II has an XRPD profile substantially as shown in FIG. 22.

Figure 23:
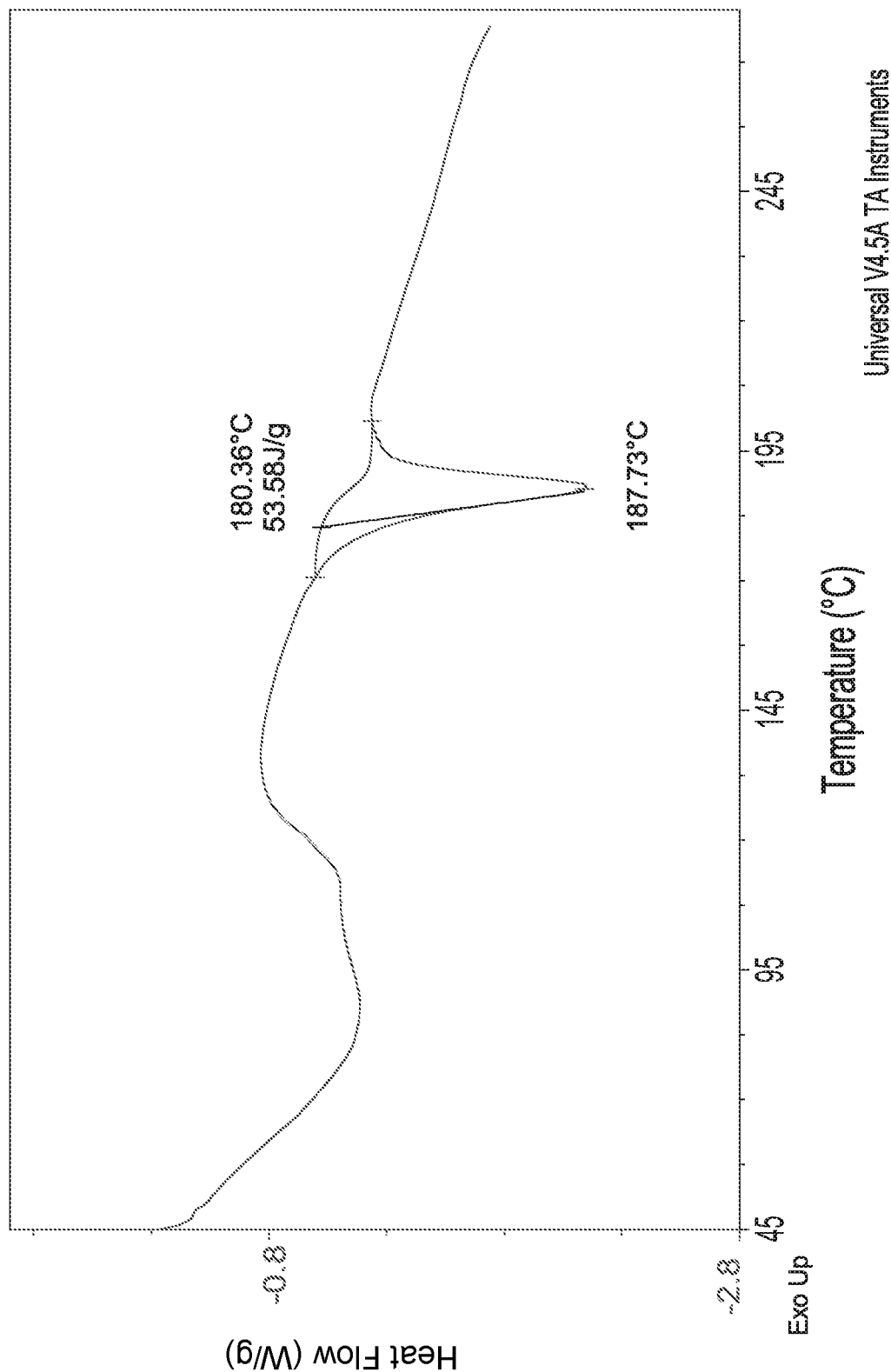
FIG. 23 shows a DSC thermogram representative of Compound II ethanesulfonic acid salt.
Figure 24:
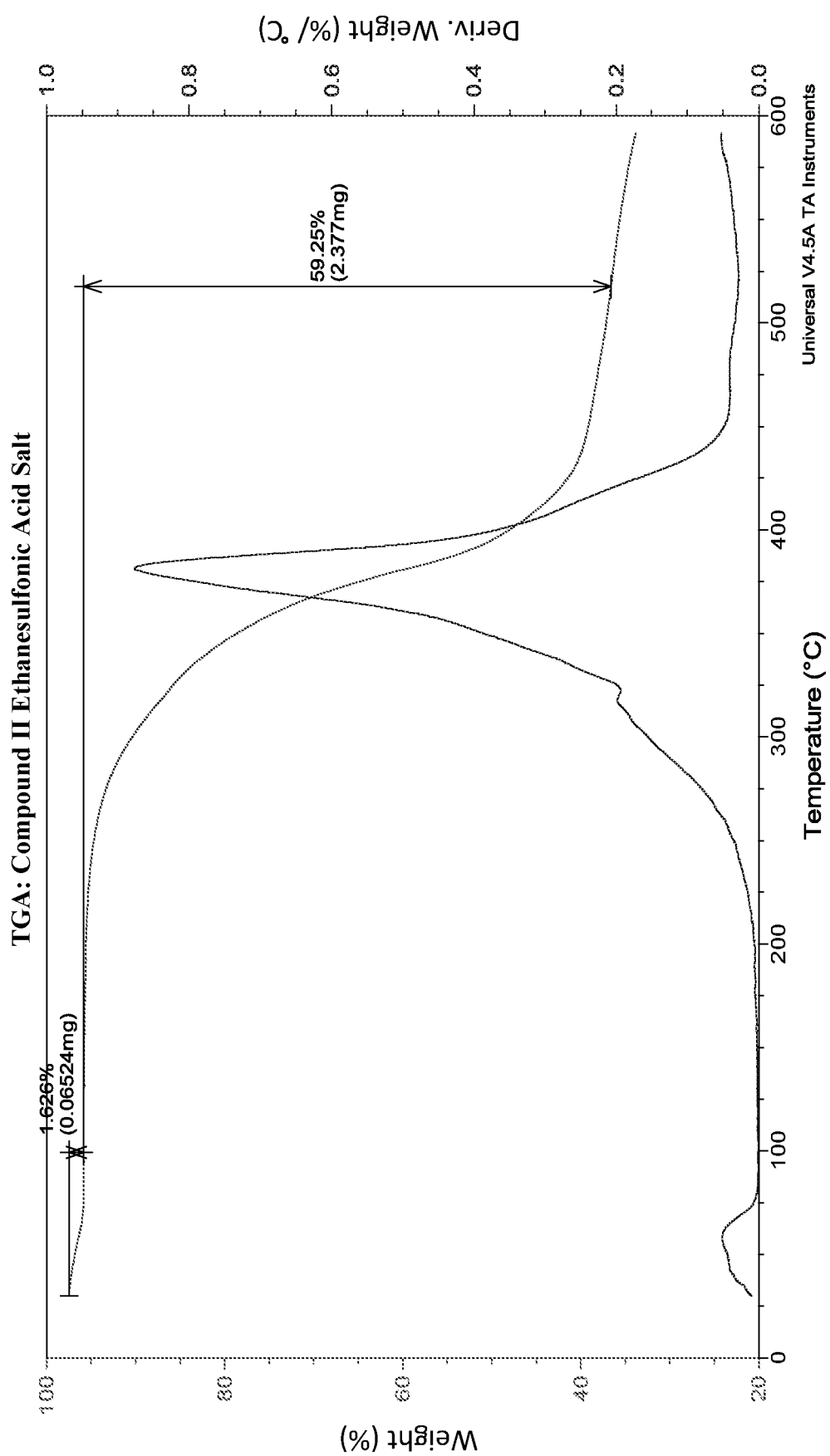
FIG. 24. shows TGA data representative of Compound II ethanesulfonic acid salt.

In some embodiments, the ethanesulfonic acid salt of the compound of Formula II has a DSC thermogram having an endothermic peak at about 187.7° C. In some embodiments, the esylate salt of the compound of Formula II has a DSC thermogram substantially as shown in FIG. 23. In some embodiments, the esylate salt of the compound of Formula II has a TGA thermogram substantially as shown in FIG. 24.

Processes

The present application further provides a process of preparing a salt of Formula I:

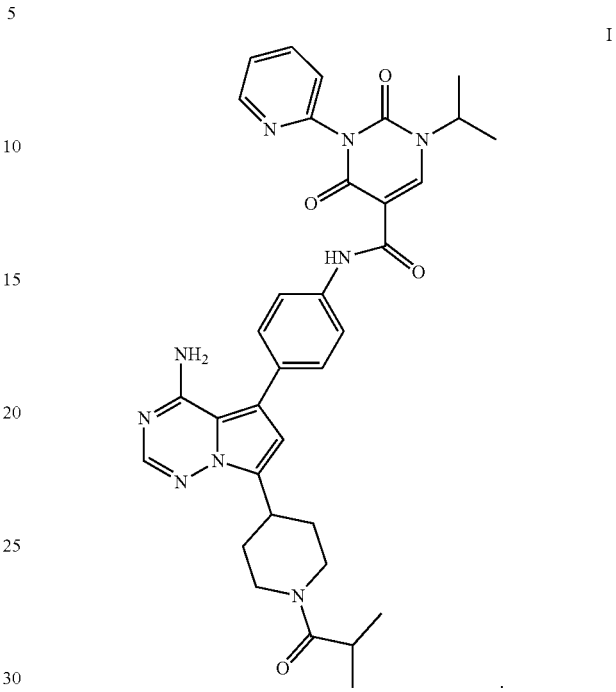

Accordingly, provided herein is a process of preparing a salt which is N-(4-(4-Amino-7-(1-isobutyrylpiperidin-4-yl)pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide maleic acid salt comprising reacting a compound of Formula I with maleic acid to form said salt. A process for preparing the maleic acid salt of a compound of Formula I is shown in Scheme 1, and described in Example 1.

In some embodiments, about 1 equivalent of maleic acid is used based on 1 equivalent of the compound of Formula I.

In some embodiments, said reacting of the compound of Formula I and maleic acid is conducted in the presence of a solvent component.

In some embodiments, said solvent component comprises methanol.

In some embodiments, said solvent component comprises dichloromethane.

In some embodiments, said solvent component comprises methanol and dichloromethane.

In some embodiments, the process further comprises removing a substantial portion of dichloromethane to precipitate said salt.

In some embodiments, the process further comprises removing a substantial portion of dichloromethane to precipitate said salt.

In some embodiments, said process further comprises, prior to said reacting, forming a solution of the compound of Formula I in a solvent component.

In a further embodiment, the solution is formed by heating a slurry of the compound of Formula I in the solvent component to a temperature of from about 45° C. to about 55° C.

In a further embodiment, said process further comprises stirring said solution; and filtering said solution to form a filtrate prior to said reacting of the compound of Formula I with maleic acid.

In a further embodiment, said process further comprises adding activated carbon and silica gel to the solution after said step of heating said slurry to a temperature of from about 45° C. to about 55° C. to form a solution and before said step of stirring said solution.

In some embodiments, the process of preparing N-(4-(4-Amino-7-(1-isobutyrylpiperidin-4-yl)pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide maleic acid salt comprises:

adding the compound of Formula I to a solvent component at room temperature to form a slurry;

heating said slurry to a temperature of from about 45° C. to about 55° C. to form a solution;

stirring said solution;

filtering said solution to produce a filtrate;

adding maleic acid to said filtrate; and removing solvent from said filtrate to precipitate said salt.

In some embodiments, said solvent component comprises methanol.

In some embodiments, said solvent component comprises dichloromethane.

In some embodiments, said solvent component comprises methanol and dichloromethane.

In some embodiments, said process further comprises adding activated carbon to the solution after said step of heating said slurry to a temperature of from about 45° C. to about 55° C. to form a solution and before said step of stirring said solution.

In some embodiments, said process further comprises adding silica gel to the solution after said step of heating said slurry to a temperature of from about 45° C. to about 55° C. to form a solution and before said step of stirring said solution.

In some embodiments, said process further comprises adding activated carbon and silica gel to the solution after said step of heating said slurry to a temperature of from about 45° C. to about 55° C. to form a solution and before said step of stirring said solution.

Provided herein is a process of preparing N-(4-(4-Amino-7-(1-isobutyrylpiperidin-4-yl)pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide maleic acid salt of Form II comprising evaporating a saturated solution of Compound I maleic acid salt in chloroform at 25±1° C. A process for preparing Form II of the maleic acid salt of a compound of Formula I is found in Example 16, Table 10.

Provided herein is a process of preparing N-(4-(4-Amino-7-(1-isobutyrylpiperidin-4-yl)pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide maleic acid salt of Form III comprising evaporating a saturated solution of Compound I maleic acid salt in 1,4-dioxane at 25±1° C. A process for preparing Form III of the maleic acid salt of a compound of Formula I is found in Example 16, Table 10.

Provided herein is a process of preparing N-(4-(4-Amino-7-(1-isobutyrylpiperidin-4-yl)pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide maleic acid salt of Form IV comprising evaporating a saturated solution of Compound I maleic acid salt in n-BuOH at 50±1° C. A process for preparing Form IV of the maleic acid salt of a compound of Formula I is found in Example 16, Table 10.

Provided herein is a process of preparing N-(4-(4-Amino-7-(1-isobutyrylpiperidin-4-yl)pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide maleic acid salt of Form V comprising adding a saturated solution of Compound I maleic acid salt in dichloromethane to heptane and stirring. A process for preparing Form V of the maleic acid salt of a compound of Formula I is found in Example 16, Table 10.

The present application further provides a process of preparing a salt of Formula II:

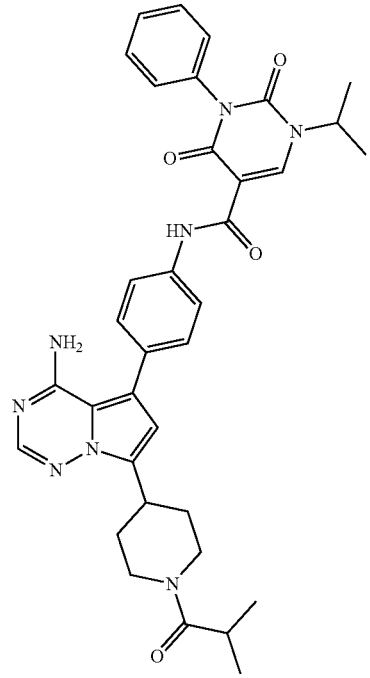

Accordingly, provided herein is a process of preparing a salt which is N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide hemi-sulfuric acid salt comprising reacting a compound of Formula II with sulfuric acid to form said salt. Processes for preparing the hemi-sulfuric acid salt of a compound of Formula II are found in Example 2 and Example 8, Table 2.

In some embodiments, about 0.6 equivalents of sulfuric acid is used based on 1 equivalent of the compound of Formula II.

In some embodiments, the process comprises:

adding the compound of Formula II to a solvent component form a solution;

adding sulfuric acid to said solution at room temperature;

concentrating the solution to form a slurry;

stirring the slurry at a temperature of from about 60° C. to about 70° C.; and cooling the slurry to a temperature of from about 15° C. to about 25° C. to precipitate said salt.

In some embodiments, the solvent component comprises methanol.

In some embodiments, the solvent component comprises dichloromethane.

In some embodiments, the solvent component comprises methanol and dichloromethane.

In some embodiments, the sulfuric acid is about 1M in water.

In some embodiments, the process further comprises preparing N-(4-(4-Amino-7-(1-isobutyrylpiperidin-4-yl)

pyrrolo[1,2-f][1,2,4]triazin-5-yl)phenyl)-1-isopropyl-2,4-dioxo-3-phenyl-1,2,3,4-tetrahydropyrimidine-5-carboxamide sulfuric acid salt. A process for preparing the sulfuric acid salt of a compound of Formula II is shown in Scheme 2, and described in Example 2.

In some embodiments, the process of preparing a salt which is N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide sulfuric acid salt comprising reacting a compound of Formula II with about 1 equivalent of sulfuric acid based on 1 equivalent of the compound of Formula II.

In some embodiments, the process for preparing N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide sulfuric acid salt comprises:
adding the compound of Formula II to a first solvent component at room temperature to form a solution;
heating the solution to a temperature of from about 50° C. to about 60° C.;
adding sulfuric acid to said solution; and
removing solvent to precipitate the sulfuric acid salt.

In some embodiments, the first solvent comprises methanol.

In some embodiments, the sulfuric acid is added as a solution in water.

In some embodiments, the above processes for preparing N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide hemi-sulfuric acid salt comprises the steps of:
adding the N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide sulfuric acid salt to a second solvent component to form a slurry;
heating the slurry to a temperature of from about 30° C. to about 40° C.;
agitating the slurry; and
collecting the resulting hemi-sulfuric acid salt.

In some embodiments, the second solvent component comprises water.

Provided herein is a process of preparing an amorphous form of N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide hemi-sulfuric acid salt. A process for preparing the amorphous form of a hemi-sulfuric acid salt of a compound of Formula II is shown in Scheme 1 and described in Example 2.

In some embodiments, preparing an amorphous form of N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide hemi-sulfuric acid salt comprises the steps of:
adding the N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide hemi-sulfuric acid salt to a third solvent component at room temperature to form a solution;
filtering the solution;
concentrating the filtrate; and
drying the resulting solid resulting in the amorphous hemi-sulfuric acid salt.

In some embodiments, the third solvent component comprises acetone and methanol.

Provided herein is a process of preparing a salt which is N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide phosphoric acid salt, comprising reacting a compound of Formula II with phosphoric acid to form said salt. A process for preparing a phosphoric acid salt of a compound of Formula II is found in Example 8, Table 2. In some embodiments, about 1.2 equivalents of phosphoric acid is used based on 1 equivalent of the compound of Formula II.

Provided herein is a process of preparing a salt which is N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide maleic acid salt comprising reacting a compound of Formula II with maleic acid to form said salt. A process for preparing a maleic acid salt of a compound of Formula II is found in Example 8, Table 2. In some embodiments, about 1.5 equivalents of maleic acid is used based on 1 equivalent of the compound of Formula II.

Provided herein is a process of preparing a salt which is N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide hydrochloric acid salt comprising reacting a compound of Formula II with hydrochloric acid to form said salt. A process for preparing a hydrochloric acid salt of a compound of Formula II is found in Example 8, Table 2. In some embodiments, about 1.2 equivalents of hydrochloric acid is used based on 1 equivalent of the compound of Formula II.

Provided herein is a process of preparing a salt which is N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide salicylic acid salt comprising reacting a compound of Formula II with salicylic acid to form said salt. A process for preparing a salicylic acid salt of a compound of Formula II is found in Example 8, Table 2. In some embodiments, about 1.2 equivalents of salicylic acid is used based on 1 equivalent of the compound of Formula II.

Provided herein is a process of preparing a salt which is N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide methanesulfonic acid salt comprising reacting a compound of Formula II with methanesulfonic acid to form said salt. A process for preparing a methanesulfonic acid salt of a compound of Formula II is found in Example 8, Table 2. In some embodiments, about 1 equivalent of methanesulfonic acid is used based on 1 equivalent of the compound of Formula II.

Provided herein is a process of preparing a salt which is N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide ethanesulfonic acid salt comprising reacting a compound of Formula II with ethanesulfonic acid to form said salt. A process for preparing an ethanesulfonic acid salt of a compound of Formula II is found in Example 8, Table 2. In some embodiments, about 1 equivalent of ethanesulfonic acid is used based on 1 equivalent of the compound of Formula II.

It is appreciated that certain features of the disclosure, which are, for clarity, described in the context of separate embodiments, can also be provided in combination in a single embodiment (while the embodiments are intended to be combined as if written in multiply dependent form). Conversely, various features of the disclosure which are, for brevity, described in the context of a single embodiment, can also be provided separately or in any suitable subcombination.

Salts and compounds of the disclosure can also include all isotopes of atoms occurring in the intermediates or final salts or compounds. Isotopes include those atoms having the same atomic number but different mass numbers. For example, isotopes of hydrogen include tritium and deuterium.

In some embodiments, the compounds or salts can be found together with other substances such as water and solvents (e.g. hydrates and solvates) or can be isolated.

In some embodiments, the compounds described herein, or salts thereof (e.g., the maleic acid salt of the compound of Formula I or the hemi-sulfuric acid salt of the compound of Formula II), are substantially isolated.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As will be appreciated, the compounds provided herein, including salts thereof, can be prepared using known organic synthesis techniques and can be synthesized according to any of numerous possible synthetic routes. The processes described herein can be monitored according to any suitable method known in the art. For example, product formation can be monitored by spectroscopic means, such as nuclear magnetic resonance spectroscopy (e.g., 1H or 13C), infrared spectroscopy, or spectrophotometry (e.g., UV-visible); or by chromatography such as high performance liquid chromatography (HPLC) or thin layer chromatography (TLC) or other related techniques.

As used herein, the term "reacting" is used as known in the art and generally refers to the bringing together of chemical reagents in such a manner so as to allow their interaction at the molecular level to achieve a chemical or physical transformation. In some embodiments, the reacting involves two reagents, wherein one or more equivalents of second reagent are used with respect to the first reagent. The reacting steps of the processes described herein can be conducted for a time and under conditions suitable for preparing the identified product.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents (or mixtures thereof) for a particular reaction step can be selected.

Suitable solvents can include halogenated solvents such as carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, 1,2-dichloroethane, 1,2-dibromoethane, hexafluorobenzene, 1,2,4-trichlorobenzene, 1,2-dichlorobenzene, chlorobenzene, fluorobenzene, mixtures thereof and the like.

Suitable ether solvents include: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, t-butyl methyl ether, mixtures thereof and the like.

Suitable protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol.

Suitable aprotic solvents can include, by way of example and without limitation, tetrahydrofuran (THF), N,N-dimethylformamide (DMF), N,N-dimethylacetamide (DMA), 1,3-dimethyl-3,4,5,6-tetrahydro-2(1H)-pyrimidinone (DMPU), 1,3-dimethyl-2-imidazolidinone (DMI), N methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable hydrocarbon solvents include benzene, cyclohexane, pentane, hexane, toluene, cycloheptane, methylcyclohexane, heptane, ethylbenzene, m-, o-, or p-xylene, octane, indane, nonane, or naphthalene.

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures).

The expressions, "ambient temperature" and "room temperature" or "rt" as used herein, are understood in the art, and refer generally to a temperature, e.g. a reaction temperature, that is about the temperature of the room in which the reaction is carried out, for example, a temperature from about 20° C. to about 30° C.

The reactions of the processes described herein can be carried out in air or under an inert atmosphere. Typically, reactions containing reagents or products that are substantially reactive with air can be carried out using air-sensitive synthetic techniques that are well known to the skilled artisan.

Methods of Use

Salts of the present disclosure (e.g., salts of the compounds of Formulae I and II) can modulate or inhibit the activity of TAM kinases. For example, the compounds of the disclosure can be used to inhibit activity of a TAM kinase in a cell or in an individual or patient in need of inhibition of the kinases by administering an inhibiting amount of a compound of the disclosure to the cell, individual, or patient.

In some embodiments, the salts of the disclosure are selective for the TAM kinases over one or more of other kinases. In some embodiments, the compounds of the disclosure are selective for the TAM kinases over other kinases. In some embodiments, the selectivity is 2-fold or more, 3-fold or more, 5-fold or more, 10-fold or more, 25-fold or more, 50-fold or more, or 100-fold or more.

The salts of the disclosure can inhibit one or more of AXL, MER and TYRO3. In some embodiments the salts are selective for one TAM kinase over another. "Selective" means that the compound binds to or inhibits a TAM kinase with greater affinity or potency, respectively, compared to a reference enzyme, such as another TAM kinase. For example, the salts can be selective for AXL over MER and TYRO3, selective for MER over AXL and TYRO3, or selective for AXL and MER over TYRO3. In some embodiments, the salts inhibit all of the TAM family members (e.g., AXL, MER and TYRO3). In some embodiments, the salts can be selective for AXL and MER over TYRO3 and other kinases. In some embodiments, provided herein is a method for inhibiting AXL and MER kinase, which comprises contacting the AXL and MER kinase with a salt provided herein, or a pharmaceutically acceptable salt thereof.

As TAM kinases inhibitors, the compounds of the disclosure are useful in the treatment of various diseases associated with abnormal expression or activity of the TAM kinases. Salts of compounds (of Formulae I and II) which inhibit TAM kinases will be useful in providing a means of preventing the growth or inducing apoptosis in tumors, particularly by inhibiting angiogenesis. It is therefore anticipated that the salts will prove useful in treating or preventing proliferative disorders such as cancers. In particular, tumours with activating mutants of receptor tyrosine kinases or upregulation of receptor tyrosine kinases may be particularly sensitive to the inhibitors.

In certain embodiments, the disclosure provides a method for treating a disease or disorder mediated by TAM kinases in a patient in need thereof, comprising the step of administering to said patient a salt provided herein (e.g., salts of the compounds of Formulae I and II), or a pharmaceutically acceptable composition thereof.

For example, the salts of the disclosure are useful in the treatment of cancer. Example cancers include bladder cancer, breast cancer, cervical cancer, colorectal cancer, cancer of the small intestine, colon cancer, rectal cancer, cancer of the anus, endometrial cancer, gastric cancer, head and neck cancer (e.g., cancers of the larynx, hypopharynx, nasopharynx, oropharynx, lips, and mouth), kidney cancer, liver cancer (e.g., hepatocellular carcinoma, cholangiocellular carcinoma), lung cancer (e.g., adenocarcinoma, small cell lung cancer and non-small cell lung carcinomas, parvicellular and non-parvicellular carcinoma, bronchial carcinoma, bronchial adenoma, pleuropulmonary blastoma), ovarian cancer, prostate cancer, testicular cancer, uterine cancer, esophageal cancer, gall bladder cancer, pancreatic cancer (e.g. exocrine pancreatic carcinoma), stomach cancer, thyroid cancer, parathyroid cancer, skin cancer (e.g., squamous cell carcinoma, Kaposi sarcoma, Merkel cell skin cancer), and brain cancer (e.g., astrocytoma, medulloblastoma, ependymoma, neuro-ectodermal tumors, pineal tumors).

Other cancers treatable with the compounds of the disclosure include bone cancer, intraocular cancers, gynecological cancers, cancer of the endocrine system, cancer of the adrenal gland, sarcoma of soft tissue, cancer of the urethra, cancer of the penis, pituitary cancer, triple-negative breast cancer (TNBC) and environmentally induced cancers including those induced by asbestos.

Further example cancers include hematopoietic malignancies such as leukemia or lymphoma, multiple myeloma, chronic lymphocytic lymphoma, adult T cell leukemia, B-cell lymphoma, cutaneous T-cell lymphoma, acute myelogenous leukemia, Hodgkin's or non-Hodgkin's lymphoma, myeloproliferative neoplasms (e.g., polycythemia vera, essential thrombocythemia, and primary myelofibrosis), Waldenstrom's Macroglubulinemia, hairy cell lymphoma, chronic myelogenic lymphoma, acute lymphoblastic lymphoma, AIDS-related lymphomas, and Burkitt's lymphoma.

Other cancers treatable with the compounds of the disclosure include tumors of the eye, glioblastoma, melanoma, rhabdosarcoma, lymphosarcoma, and osteosarcoma.

Salts of the disclosure can also be useful in the inhibition of tumor metastisis.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), small lymphocytic lymphoma (SLL), chronic myelogenous leukemia (CIVIL), diffuse large B-cell lymphoma (DLBCL), mantle cell lymphoma (MCL), marginal zone lymphoma (MZL), Non-Hodgkin lymphoma (including relapsed or refractory NHL), follicular lymphoma (FL), Hodgkin lymphoma, lymphoblastic lymphoma, myeloproliferative diseases (e.g., primary myelofibrosis (PMF), polycythemia vera (PV), essential thrombocytosis (ET)), myelodysplasia syndrome (MDS), T-cell acute lymphoblastic lymphoma (T-ALL), multiple myeloma, cutaneous T-cell lymphoma, peripheral T-cell lymphoma, Waldenstrom's Macroglubulinemia, hairy cell lymphoma, chronic myelogenic lymphoma and Burkitt's lymphoma.

Exemplary sarcomas include chondrosarcoma, Ewing's sarcoma, osteosarcoma, rhabdomyosarcoma, angio sarcoma, fibro sarcoma, lipo sarcoma, myxoma, rhabdomyoma, rhabdosarcoma, fibroma, lipoma, harmatoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), colorectal cancer and bile duct cancer.

Exemplary genitourinary tract cancers include cancers of the kidney (adenocarcinoma, Wilm's tumor [nephroblastoma], renal cell carcinoma), bladder and urethra (squamous cell carcinoma, transitional cell carcinoma, adenocarcinoma, urothelial carcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angio sarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma, Lhermitte-Duclos disease, neoplasm of the central nervous system (CNS), primary CNS lymphoma and spinal axis tumor.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, Merkel cell skin cancer, moles dysplastic nevi, lipoma, angioma, dermatofibroma, and keloids.

Exemplary head and neck cancers include glioblastoma, melanoma, rhabdosarcoma, lymphosarcoma, osteosarcoma, squamous cell carcinomas, adenocarcinomas, oral cancer, laryngeal cancer, nasopharyngeal cancer, nasal and paranasal cancers, thyroid and parathyroid cancers.

In some embodiments, the present disclosure provides a method for treating hepatocellular carcinoma in a patient in need thereof, comprising the step of administering to said patient a salt of compound of Formula I or a salt of a compound of Formula II, or a composition comprising a salt of a compound of Formula I or a salt of a compound of Formula II.

In some embodiments, the present disclosure provides a method for treating Rhabdomyo sarcoma, esophageal cancer, breast cancer, or cancer of a head or neck, in a patient in need thereof, comprising the step of administering to said patient a a salt of compound of Formula I or a salt of a compound of Formula II, or a composition comprising a salt of a compound of Formula I or a salt of a compound of Formula II.

In some embodiments, the present disclosure provides a method of treating cancer, wherein the cancer is selected from hepatocellular cancer, breast cancer, bladder cancer, colorectal cancer, melanoma, mesothelioma, lung cancer, prostate cancer, pancreatic cancer, testicular cancer, thyroid cancer, squamous cell carcinoma, glioblastoma, neuroblastoma, uterine cancer, and rhabdosarcoma.

Targeting TAM receptor tyrosine kinases can provide a therapeutic approach to treat viral diseases (T Shibata, et al. *The Journal of Immunology,* 2014, 192, 3569-3581). The present disclosure provides a method for treating infections such as viral infections. The method includes administering to a patient in need thereof, a therapeutically effective amount of a salt of compound of Formula I or a salt of a compound of Formula II, or a composition comprising a salt of a compound of Formula I or a salt of a compound of Formula II.

Examples of viruses causing infections treatable by methods of the present disclosure include, but are not limit to, human immunodeficiency virus, human papillomavirus, influenza, hepatitis A, B, C or D viruses, adenovirus, poxvirus, herpes simplex viruses, human cytomegalovirus, severe acute respiratory syndrome virus, ebola virus, Marburg virus and measles virus. In some embodiments, viruses causing infections treatable by methods of the present disclosure include, but are not limit to, hepatitis (A, B, or C), herpes virus (e.g., VZV, HSV-1, HAV-6, HSV-II, and CMV, Epstein Barr virus), adenovirus, influenza virus, flaviviruses (for example: West Nile, dengue, tick-borne encephalitis, yellow fever, Zika), echovirus, rhinovirus, coxsackie virus, cornovirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

In some embodiments, the present disclosure provides a method for treating thrombus formation (J.M.E.M. Cosemans et al. *J. of Thrombosis and Haemostasis* 2010, 8, 1797-1808 and A. Angelillo-Scherrer et al. *J. Clin. Invest.* 2008, 118, 583-596).

Combination Therapies

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with the compounds of Formula (I) or a compound as described herein for treatment of TAM-associated diseases, disorders or conditions. The agents can be combined with the present salts (e.g., e.g., salts of the compounds of Formulae I and II) in a single dosage form, or the agents can be administered simultaneously or sequentially as separate dosage forms.

Suitable antiviral agents contemplated for use in combination with the salts of the present disclosure can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddl); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2', 3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

Suitable agents for use in combination with the salts of the present application for the treatment of cancer include chemotherapeutic agents, targeted cancer therapies, immunotherapies or radiation therapy. Salts of this disclosure may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds of the present disclosure. These include anti-androgens including but not limited to flutamide, bicalutamide, and nilutamide, luteinizing hormone-releasing hormone (LHRH) analogs including leuprolide, oserelin, triptorelin, and histrelin, LHRH antagonists (e.g. degarelix), androgen receptor blockers (e.g. enzalutamide) and agents that inhibit androgen production (e.g. abiraterone).

Salts of the present disclosure may be combined with or in sequence with other agents against membrane receptor kinases especially for patients who have developed primary or acquired resistance to the targeted therapy. These therapeutic agents include inhibitors or antibodies against EGFR, Her2, VEGFR, c-Met, Ret, IGFR1, PDGFR, FGFR1, FGFR2, FGFR3, FGFR4, TrkA, TrkB, TrkC, ROS, c-Kit, or Flt-3 and against cancer-associated fusion protein kinases such as Bcr-Abl and EML4-Alk. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab. Inhibitors of c-Met may be used in combination with TAM inhibitors. These include onartumzumab, tivantnib, and INC-280. Agents against FGFRs include but not limited to AZD4547, BAY1187982, ARQ087, BGJ398, BIBF1120, TKI258, lucitanib, dovitinib, TAS-120, JNJ-42756493, and Debio1347. Agents against Trks include but not limited to LOXO-101 and RXDX-101. Agents against Abl (or Bcr-Abl) include imatinib, dasatinib, nilotinib, and ponatinib and those against Alk (or EML4-ALK) include crizotinib. Angiogenesis inhibitors may be efficacious in some tumors in combination with TAM inhibitors. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with compounds of the present disclosure include inhibitors of the PI3K-AKT-mTOR pathway, inhibitors of the Raf-MAPK pathway, inhibitors of JAK-STAT pathway, inhibitors of Pim kinases, and inhibitors of protein chaperones and cell cycle progression.

Agents against the PI3 kinase include but are not limited to pilaralisib, idelalisib, buparlisib, and IPI-549. In some embodiments, the PI3K inhibitor is selective for PI3K alpha, PI3K beta, PI3K gamma or PI3K delta. Inhibitors of mTOR such as rapamycin, sirolimus, temsirolimus, and everolimus may be combined with TAM kinases inhibitors. Other suitable examples include but are not limited to vemurafenib and dabrafenib (Raf inhibitors) and trametinib, selumetinib and GDC-0973 (MEK inhibitors). Inhibitors of one or more JAKs (e.g., ruxolitinib, baricitinib, tofacitinib), Hsp90 (e.g., tanespimycin), cyclin dependent kinases (e.g., palbociclib), PARP (e.g., olaparib), and proteasomes (e.g., bortezomib, carfilzomib) can also be combined with compounds of the present disclosure. In some embodiments, the JAK inhibitor is selective for JAK1 over JAK2 and JAK3. Agents against Pim kinases include but not limited to LGH447, INCB053914, and SGI-1776.

Other suitable agents for use in combination with the salts of the present disclosure include chemotherapy combinations such as platinum-based doublets used in lung cancer and other solid tumors (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles (Abraxane®).

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with the salts of the present disclosure include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds provided herein may also be combined with immunotherapy drugs, including cytokines such as interferon alpha, interleukin 2, and tumor necrosis factor (TNF) inhibitors.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (TAXOL™), mithramycin, deoxycoformycin, mitomycin-C, L-asparaginase, interferons (especially IFN-α), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB and PD-1, or antibodies to cytokines (IL-10, TGF-β, etc.).

Other anti-cancer agents include CSF1R inhibitors (PLX3397, LY3022855, etc.) and CSF1R antibodies (IMC-CS4, RG7155, etc.).

Other anti-cancer agents include BET inhibitors (INCB054329, OTX015, CPI-0610, etc.), LSD1 inhibitors (GSK2979552, INCB059872, etc), HDAC inhibitors (panobinostat, vorinostat, etc), DNA methyl transferase inhibitors (azacitidine and decitabine), and other epigenetic modulators.

Other anti-cancer agents include Bcl2 inhibitor ABT-199, and other Bcl-2 family protein inhibitors.

Other anti-cancer agents include TGF beta receptor kinase inhibitor such as LY2157299.

Other anti-cancer agents include BTK inhibitor such as ibrutinib.

Other anti-cancer agents include beta catenin pathway inhibitors, notch pathway inhibitors and hedgehog pathway inhibitors.

Other anti-cancer agents include inhibitors of kinases associated cell proliferative disorder. These kinases include but not limited to Aurora-A, CDK1, CDK2, CDK3, CDK5, CDK7, CDK8, CDK9, ephrin receptor kinases, CHK1, CHK2, SRC, Yes, Fyn, Lck, Fer, Fes, Syk, Itk, Bmx, GSK3, JNK, PAK1, PAK2, PAK3, PAK4, PDK1, PKA, PKC, Rsk and SGK.

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

One or more additional immune checkpoint inhibitors can be used in combination with a salt as described herein for treatment of TAM-associated diseases, disorders or conditions. Exemplary immune checkpoint inhibitors include inhibitors against immune checkpoint molecules such as CD20, CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3, TIM3, VISTA, CD96, TIGIT, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, CD96, TIGIT, and VISTA. In some embodiments, the salts provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, or AMP-224. In some embodiments, the anti-PD-1 monoclonal antibody is nivolumab, pembrolizumab, or PDR001. In some embodiments, the anti-PD1 antibody is pembrolizumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C.

In some embodiments, the anti-PD-L1 monoclonal antibody is MPDL3280A (atezolizumab) or MEDI4736 (durvalumab).

In some embodiments, the inhibitor of an immune checkpoint molecule is an inhibitor of CTLA-4, e.g., an anti-CTLA-4 antibody. In some embodiments, the anti-CTLA-4 antibody is ipilimumab or tremelimumab.

In some embodiments, the inhibitor of an immune checkpoint molecule is an inhibitor of LAG3, e.g., an anti-LAG3 antibody. In some embodiments, the anti-LAG3 antibody is BMS-986016 or LAG525.

In some embodiments, the inhibitor of an immune checkpoint molecule is an inhibitor of GITR, e.g., an anti-GITR antibody. In some embodiments, the anti-GITR antibody is TRX518, MK-4166, INCAGN01876 or MK-1248.

In some embodiments, the inhibitor of an immune checkpoint molecule is an inhibitor of OX40, e.g., an anti-OX40 antibody or OX40L fusion protein. In some embodiments, the anti-OX40 antibody is MEDI0562, INCAGN01949, GSK2831781, GSK-3174998, MOXR-0916, PF-04518600 or LAG525. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The salts of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

Salts of the present disclosure can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

The salts of the present disclosure can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF.

The salts of the present disclosure can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the salts of the present disclosure can be used in combination with tumor specific antigen such as heat shock proteins isolated from tumor tissue itself. In some embodiments, the salts of the present disclosure can be combined with dendritic cells immunization to activate potent anti-tumor responses.

The salts of the present disclosure can be used in combination with bispecific macrocyclic peptides that target Fc alpha or Fc gamma receptor-expressing effectors cells to tumor cells. The salts of the present disclosure can also be combined with macrocyclic peptides that activate host immune responsiveness.

The salts of the present disclosure can be used in combination with arginase inhibitors, for example CB-1158.

The salts of the present disclosure can be used in combination with one or more metabolic enzyme inhibitors. In some embodiments the metabolic enzyme inhibitor is an inhibitor or IDO1, TDO or arginase. Examples of IDO1 inhibitors include epacadostat and NGL919.

The salts of the present disclosure can be used in combination with bone marrow transplant for the treatment of a variety of tumors of hematopoietic origin.

The salts of the present disclosure can be used as anticoagulant as single agent or in combination with other anticoagulants including but not limited to apixaban, dabigatran, edoxaban, fondaparinex, heparin, rivaroxaban, and warfarin.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, the salts provided herein can be administered in the form of pharmaceutical compositions which refers to a combination of a compound provided herein, or its pharmaceutically acceptable salt, and at least one pharmaceutically acceptable carrier. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal, or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This application also includes pharmaceutical compositions which contain, as the active ingredient, one or more of the salts provided herein (e.g., salts of the compounds of Formulae I and II) in combination with one or more pharmaceutically acceptable carriers. In making the compositions of the present disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound (or the salt forms of the disclosure) can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the present disclosure can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid pre-formulation composition containing a homogeneous mixture of a compound of the present disclosure. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the salts and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

The compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of salts (e.g., salts of the compounds of Formulae I and II) or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound or salt of the present disclosure can vary according to, for example, the particular use for which the treatment is made, the manner of administration of the compound, the health and condition of the patient, and the judgment of the prescribing physician. The proportion or concentration of a compound or salt provided herein in a pharmaceutical composition can vary depending upon a number of factors including dosage, chemical characteristics (e.g., hydrophobicity), and the route of administration. For example, the compounds or salts provided herein can be provided in an aqueous physiological buffer solution containing about 0.1 to about 10% w/v of the compound or salt for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds or salts provided herein can also be formulated in combination with one or more additional active ingredients which can include any pharmaceutical agent such as anti-viral agents, vaccines, antibodies, immune enhancers, immune suppressants, anti-inflammatory agents and the like.

Kits

The present disclosure also includes pharmaceutical kits useful, for example, in the treatment or prevention of TAM-associated diseases or disorders, obesity, diabetes and other diseases referred to herein which include one or more containers containing a pharmaceutical composition comprising a therapeutically effective amount of a salt (e.g., salts of the compounds of Formulae I and II) provided herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of TAM kinases as described below.

General Methods

Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification," K. Blom, R. Sparks, J. Doughty, G. Everlof, T. Hague, A. Combs, *J. Combi. Chem.*, 5, 670 (2003); and "Preparative LC-MS Purification: Improved Compound Specific Method Optimization," K. Blom, B. Glass, R. Sparks, A. Combs, *J. Combi. Chem.*, 6, 874-883 (2004). The compounds separated were typically subjected to analytical liquid chromatography mass spectrometry (LCMS) for purity check under the following conditions: Instrument; Agilent 1100 series, LC/MSD, Column: Waters Sunfire™ $C_{18}$ 5 µm particle size, 2.1×5.0 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm particle size, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [see "Preparative LCMS Purification: Improved Compound Specific Method Optimization," K. Blom, B. Glass, R. Sparks, A. Combs, *J. Comb. Chem.*, 6, 874-883 (2004)]. Typically, the flow rate used with the 30×100 mm column was 60 mL/minute.

pH=10 purifications: Waters)(Bridge $C_{18}$ 5 μm particle size, 19×100 mm column, eluting with mobile phase A: 0.15% $NH_4OH$ in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization," K. Blom, B. Glass, R. Sparks, A. Combs, *J. Comb. Chem.*, 6, 874-883 (2004)]. Typically, the flow rate used with 30×100 mm column was 60 mL/minute.

Example 1. Synthesis of N-(4-(4-Amino-7-(1-isobutyrylpiperidin-4-yl)pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide maleate (Compound I Maleate Salt, Form I)

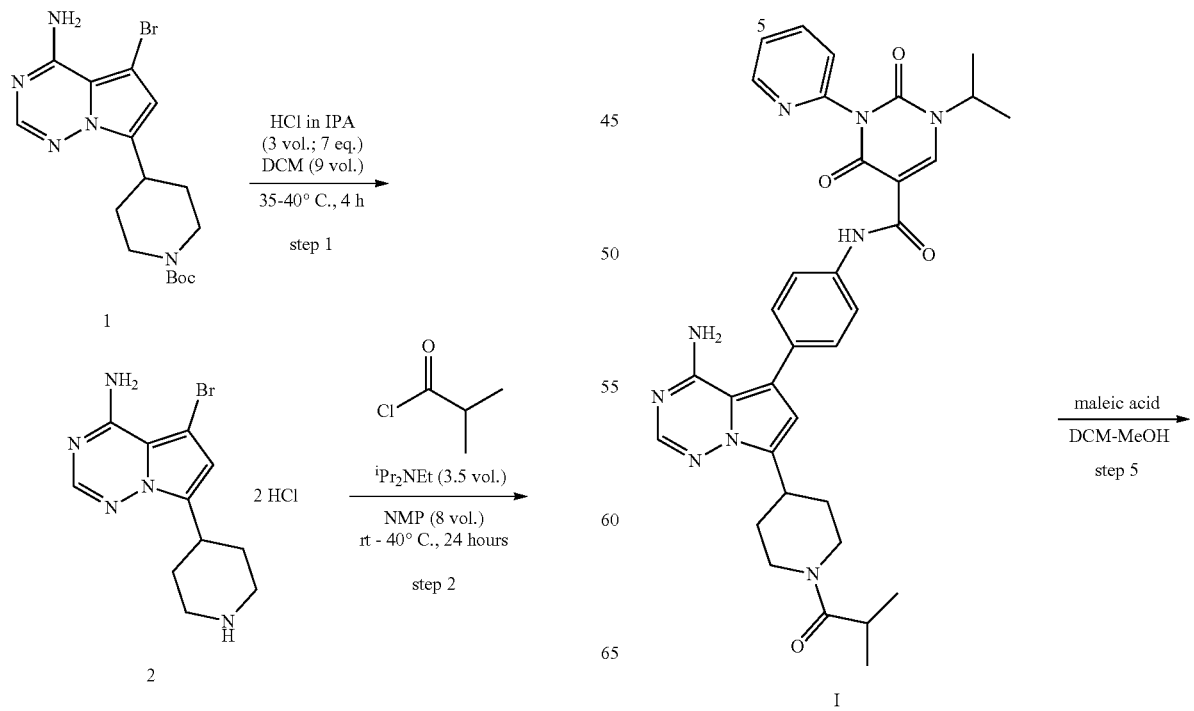

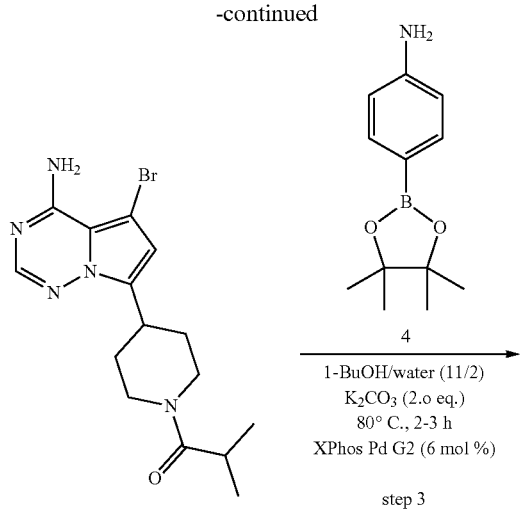

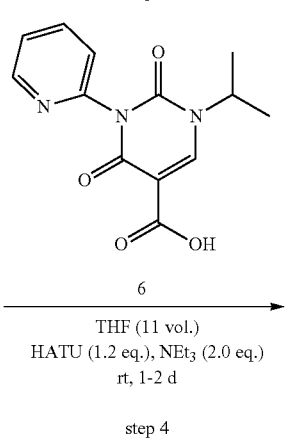

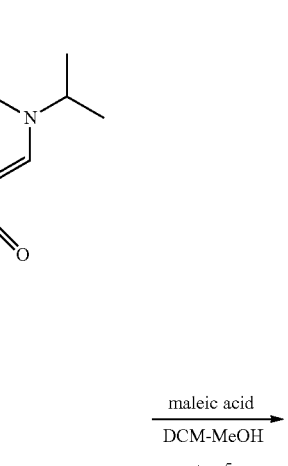

-continued

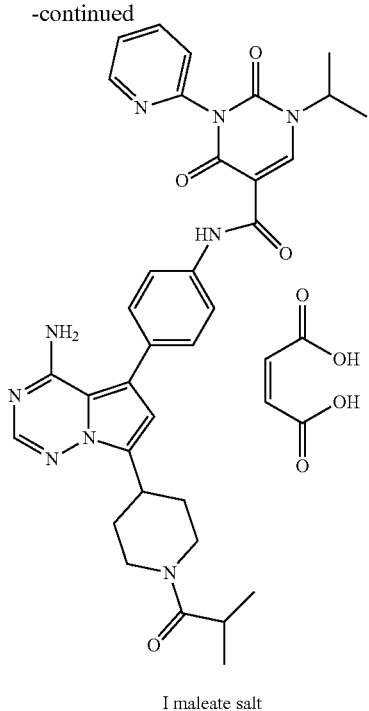

I maleate salt

Step 1. 5-Bromo-7-(piperidin-4-yl)pyrrolo[1,2-f][1,2,4]triazin-4-amine dihydrochloride (Compound 2)

In a 5-necked 22-L round bottom flask equipped with a mechanical stirrer, a heating mantle, a thermal couple, a reflux conderser, a nitrogen inlet and a nitrogen outlet was placed tert-butyl 4-(4-amino-5-bromopyrrolo[2,1-f][1,2,4]triazin-7-yl)piperidine-1-carboxylate (Compound 1, 880 g, 2.221 mol) in dichloromethane (DCM, 8.0 L) at room temperature. To the suspension was added hydrochloric acid in 2-propanol (5.8 N, 2.7 L, 15.66 mol, 7.05 eq.). The mixture was heated to 35° C. After 4 hours, the reaction mixture was diluted with tert-butyl methyl ether (TBME, 4.5 L). The resulting mixture was cooled to room temperature, filtered and washed with TBME (2.0 L). The cake was dried on the filter under house vacuum for 24 hours to provide 5-bromo-7-(piperidin-4-yl)pyrrolo[1,2-f][1,2,4]triazin-4-amine dihydrochloride (Compound 2, 848 g, 103%) as a light brown solid. $^1$H NMR (400 MHz, DMSO-$d_6$) δ 9.53-9.29 (m, 3H), 8.23 (s, 1H), 6.91 (s, 1H), 3.38 (tt, J=11.8, 3.6 Hz, 1H), 3.30 (d, J=12.4 Hz, 2H), 3.00 (dtd, J=12.8, 10.1, 2.6 Hz, 2H), 2.07 (dd, J=14.1, 3.8 Hz, 2H), 1.97-1.87 (m, 2H) ppm; $^{13}$C NMR (101 MHz, DMSO-$d_6$) δ 150.34, 139.32, 138.92, 113.24, 109.67, 95.70, 43.06, 30.57, 26.89 ppm; $C_{11}H_{14}BrN_5$ (MW 295.0), LCMS (EI) m/e 296.0 (M$^+$+H).

Step 2. 1-(4-(4-Amino-5-bromopyrrolo[1,2-f][1,2,4]triazin-7-yl)piperidin-1-yl)-2-methylpropan-1-one (Compound 3)

In a 5-necked 22-L round bottom flask equipped with a mechanical stirrer, a thermal couple, a reflux conderser, a nitrogen inlet and a nitrogen outlet was placed 5-bromo-7-(piperidin-4-yl)pyrrolo[1,2-f][1,2,4]triazin-4-amine dihydrochloride (Compound 2, 1300 g, 3.522 mol) in N-methyl piperidinone (NMP, 10 L) at room temperature. To the suspension was added N,N-diisopropylethylamine (1593 g, 12.3 mol). The mixture was cooled to 10° C. before charging isobutyryl chloride (388 g, 3.645 mol). The reaction was agitated at room temperature, and monitored by HPLC. Extra isobutyryl chloride (22.5 g, 0.211 mol) was added to consume all the starting material. Once the reaction was completed, the reaction mixture was filtered through a Celite pad. The resulting filtrate was cooled to 10° C., water (26 L) was added gradually to precipitate out the product. The solids were collected by filtration, and washed by water (12 L). The cake was dried on the filter under house vacuum for 48 hours to provide 1-(4-(4-amino-5-bromopyrrolo[1,2-f][1,2,4]triazin-7-yl)piperidin-1-yl)-2-methylpropan-1-one (Compound 3, 1095 g, 85%) as a light brown solid. $^1$H NMR (400 MHz, DMSO-$d_6$) δ 7.86 (s, 1H), 6.64 (s, 1H), 4.51 (d, J=12.6 Hz, 1H), 4.01 (d, J=13.2 Hz, 1H), 3.35-3.30 (m, 1H), 3.12 (t, J=12.3 Hz, 1H), 2.91-2.84 (m, 1H), 2.64 (t, J=12.1 Hz, 1H), 2.02-1.93 (m, 2H), 1.55-1.42 (m, 2H), 1.02 (d, J=6.5 Hz, 3H), 1.00 (d, J=6.5 Hz, 3H) ppm; $^{13}$C NMR (101 MHz, DMSO-$d_6$) δ 174.50, 155.68, 148.37, 135.22, 111.36, 110.65, 87.27, 45.34, 41.67, 32.91, 31.30, 30.33, 29.49, 20.03, 19.87 ppm; $C_{15}H_{20}BrN_5O$ (MW 365.09), LCMS (EI) m/e 366.1 (M$^+$+H).

Step 3. 1-(4-(4-Amino-5-(4-aminophenyl)pyrrolo[1,2-f][1,2,4]triazin-7-yl)piperidin-1-yl)-2-methylpropan-1-one (Compound 5)

A 5-necked 22-L round bottom flask equipped with a mechanical stirrer, a heating mantle, a thermal couple, a reflux condenser, a nitrogen inlet and a nitrogen outlet was charged with 1-(4-(4-amino-5-bromopyrrolo[1,2-f][1,2,4]triazin-7-yl)piperidin-1-yl)-2-methylpropan-1-one (Compound 3, 700 g, 1.911 mol), 4-(4,4,5,5-tetramethyl-1,3,2-dioxaborolan-2-yl)aniline (Compound 4, 502 g, 2.293 mol), and potassium carbonate (528 g, 3.822 mol) in 1-butanol (7.7 L) and water (1.4 L) at room temperature. To the mixture was added chloro(2-dicyclohexylphosphino-2',4',6'-triisopropyl-1,1'-biphenyl)[2-(2'-amino-1,1'-biphenyl)]palladium(II) (XPhos Pd G2, 90 g, 115 mmol) at room temperature. The reaction mixture was degased and refilled with nitrogen before heating up to 80° C. After two hours at 80° C., n-heptane (8 L) was added to the reaction mixture. The resulting slurry was cooled to room temperature. The solids were collected by filtration, and washed with water (6 L). The cake was dried on the filter under house vacuum for 72 hours to provide 1-(4-(4-amino-5-(4-aminophenyl)pyrrolo[1,2-f][1,2,4]triazin-7-yl)piperidin-1-yl)-2-methylpropan-1-one (Compound 5, 648 g, 90%) as a brown solid. $^1$H NMR (500 MHz, DMSO-$d_6$) δ 7.85 (s, 1H), 7.09 (d, J=8.4 Hz, 2H), 6.65 (d, J=8.4 Hz, 2H), 6.43 (s, 1H), 5.24 (s, 2H), 4.53 (d, J=12.6 Hz, 1H), 4.04 (d, J=13.1 Hz, 1H), 3.38 (ddd, J=11.8, 8.2, 3.8 Hz, 1H), 3.16 (t, J=12.7 Hz, 1H), 2.87 (p, J=6.7 Hz, 1H), 2.71-2.66 (m, 1H), 2.08-2.00 (m, 2H), 1.61-1.58 (m, 2H), 1.02 (d, J=6.5 Hz, 3H), 1.00 (d, J=6.5 Hz, 3H) ppm; $^{13}$C NMR (126 MHz, DMSO-$d_6$) δ 174.51, 156.31, 148.51, 147.65, 133.98, 130.35, 122.57, 119.37, 114.57, 109.67, 108.85, 45.48, 41.81, 32.97, 31.50, 30.56, 29.50, 20.06, 19.89 ppm; $C_{21}H_{26}N_6O$ (MW 378.48), LCMS (EI) m/e 379.2 (M$^+$+H).

Step 4. N-(4-(4-Amino-7-(1-isobutyrylpiperidin-4-yl)pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide (Compound I)

In a 5-necked 22-L round bottom flask equipped with a mechanical stirrer, a thermal couple, a nitrogen inlet and a nitrogen outlet were placed 1-(4-(4-amino-5-(4-aminophenyl)pyrrolo[1,2-f][1,2,4]triazin-7-yl)piperidin-1-yl)-2-methylpropan-1-one (Compound 5, 944 g, 2.494 mol), and 1-isopropyl-2,4-dioxo-3-(pyridin-2-yl)-1,2,3,4-tetrahydropyrimidine-5-carboxylic acid hydrochloride (Compound 6, 801 g, 2.569 mol) in tetrahydrofuran (THF, 10 L) at room temperature. The reaction mixture was added triethylamine (NEt$_3$, 0.695 L, 4.988 mol). Upon the completion of the reaction, the reaction mixture was divided evenly into two 22-L round bottom flasks. To each flask was charged water (8 L) at room temperature. The solids were collected by filtration. The resulting wet cake was put back into a 22-L round bottom flask. To the flask was charged THF (3.2 L) and water (10.5 L). The slurry was heated to 55° C., and agitated at 55° C. for two hours. The solids were collected by filtration at 30° C., and washed with water (8 L). The cake was dried on the filter under house vacuum for 72 hours to provide N-(4-(4-amino-7-(1-isobutyrylpiperidin-4-yl)pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide (Compound I, 1425 g, 90%) as light brown solid. $^1$H NMR (500 MHz, DMSO-d$_6$) δ 10.82 (s, 1H), 8.71 (s, 1H), 8.64 (ddd, J=4.8, 1.8, 0.8 Hz, 1H), 8.06 (td, J=7.7, 1.9 Hz, 1H), 7.91 (s, 1H), 7.77 (d, J=8.6 Hz, 2H), 7.60-7.53 (m, 2H), 7.43 (d, J=8.6 Hz, 2H), 6.58 (s, 1H), 4.78 (hept, J=6.8 Hz, 1H), 4.54 (d, J=12.3 Hz, 1H), 4.06 (d, J=12.5 Hz, 1H), 3.40 (tt, J=11.7, 3.5 Hz, 1H), 3.20 (t, J=12.3 Hz, 1H), 2.91 (hept, J=6.7 Hz, 1H), 2.69 (t, J=12.3 Hz, 1H), 2.06 (dd, J=27.7, 12.3 Hz, 2H), 1.61 (q, J=11.8 Hz, 1H), 1.55-1.47 (m, 1H), 1.44 (d, J=6.8 Hz, 6H), 1.02 (d, J=6.8 Hz, 3H), 1.00 (d, J=6.8 Hz, 3H) ppm; $^{13}$C NMR (126 MHz, DMSO-d$_6$) δ 174.51, 163.02, 160.31, 156.20, 150.18, 149.98, 149.18, 148.08, 147.79, 139.55, 137.51, 134.45, 131.24, 130.23, 125.09, 124.57, 120.46, 117.98, 109.90, 109.35, 105.27, 51.17, 45.46, 41.79, 32.97, 31.48, 30.54, 29.49, 21.09 (2 —CH$_3$), 20.07, 19.89 ppm; C$_{34}$H$_{37}$N$_9$O$_4$ (MW 635.73), LCMS (EI) m/e 636.3 (M$^+$+H).

Step 5. N-(4-(4-Amino-7-(1-isobutyrylpiperidin-4-yl)pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide maleate (Compound I Maleate Salt, Form I)

In a 50-L reactor equipped with a mechanical stirrer, a heating jacket, a thermal couple, a reflux condenser, a nitrogen inlet and a nitrogen outlet was placed N-(4-(4-amino-7-(1-isobutyrylpiperidin-4-yl)pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide (Compound I, 1401 g, 2.204 mol) in methanol (MeOH, 10 L) and dichloromethane (DCM, 20 L) at room temperature. The slurry was heated to 50° C. to provide a solution. To the solution was added activated carbon (70 g) and silica gel (70 g). After stirring for 2 hours at 50° C., the mixture was filtered through a Celite pad. To the filtrate was added maleic acid (269 g, 2.314 mol). Most of the DCM was distilled out under atmospheric pressure. Solids gradually precipitated out. The solids were collected by filtration at 18° C., and washed with MeOH (3 L). The cake was dried on the filter under house vacuum for 72 hours to provide N-(4-(4-amino-7-(1-isobutyrylpiperidin-4-yl)pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide maleate (Compound I maleate salt, 1425 g, 86%) as an off-white solid. $^1$H NMR (400 MHz, DMSO-d$_6$) δ 10.83 (s, 1H), 8.71 (s, 1H), 8.65-8.63 (m, 1H), 8.06 (td, J=7.8, 1.9 Hz, 1H), 7.95 (s, 1H), 7.77 (d, J=8.6 Hz, 2H), 7.58-7.55 (m, 2H), 7.44 (d, J=8.5 Hz, 2H), 6.62 (s, 1H), 6.25 (s, 2H), 4.78 (hept, J=6.7 Hz, 1H), 4.54 (d, J=12.3 Hz, 1H), 4.06 (d, J=12.5 Hz, 1H), 3.40 (tt, J=11.6, 3.2 Hz, 1H), 3.20 (t, J=12.3 Hz, 1H), 2.90 (hept, J=6.6 Hz, 1H), 2.69 (t, J=12.1 Hz, 1H), 2.09-2.01 (m, 2H), 1.65-1.57 (m, 1H), 1.56-1.49 (m, 1H), 1.44 (d, J=6.8 Hz, 6H), 1.02 (d, J=5.5 Hz, 3H), 1.00 (d, J=5.5 Hz, 3H) ppm; $^{13}$C NMR (101 MHz, DMSO) δ 174.52, 167.21, 163.03, 160.33, 155.20, 150.18, 149.99, 149.18, 148.07, 146.26, 139.55, 137.67, 135.32, 131.34, 130.87, 130.22, 125.09, 124.57, 120.49, 119.30, 109.80, 109.47, 105.26, 51.17, 45.43, 41.76, 32.97, 31.45, 30.53, 29.50, 21.09 (2 —CH$_3$), 20.06, 19.89 ppm; C$_{34}$H$_{37}$N$_9$O$_4$ (free base, MW 635.73), LCMS (EI) m/e 636.3 (M$^+$+H).

Example 2. Synthesis of N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide hemisulfate (amorphous) (Compound II Hemisulfate Salt)

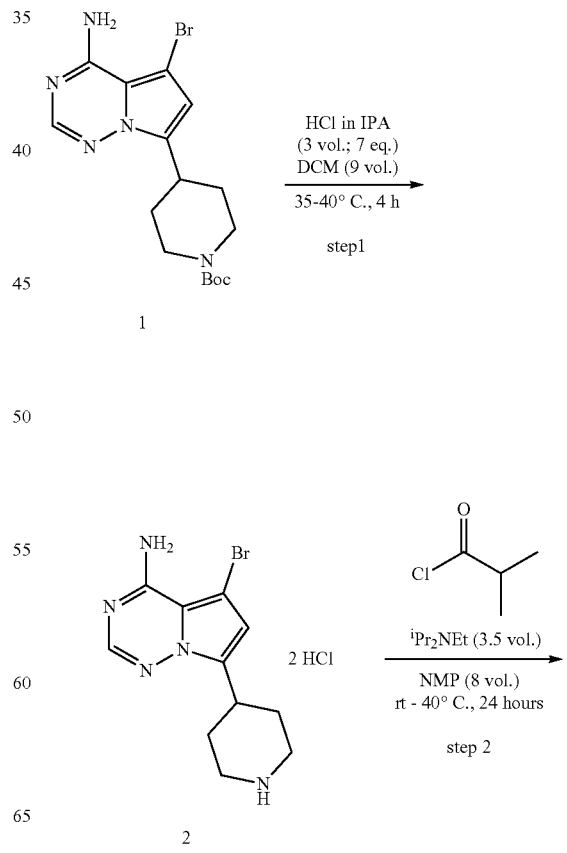

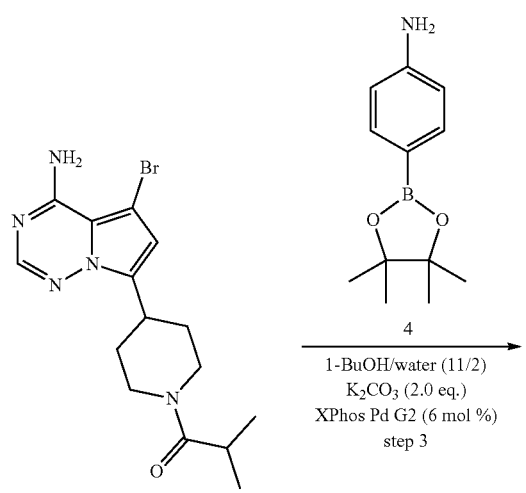
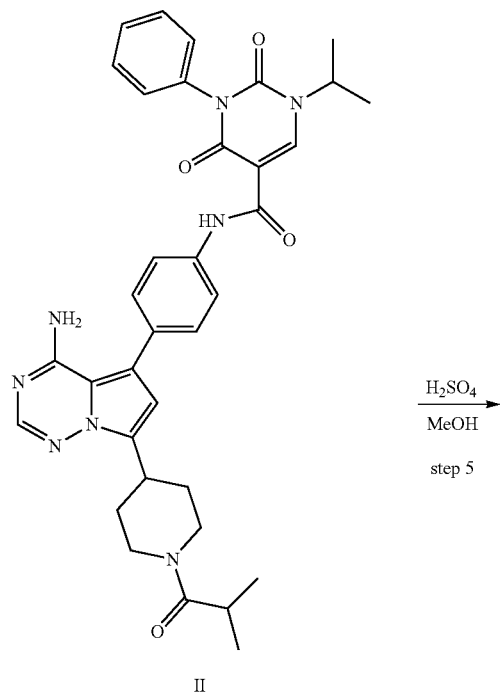
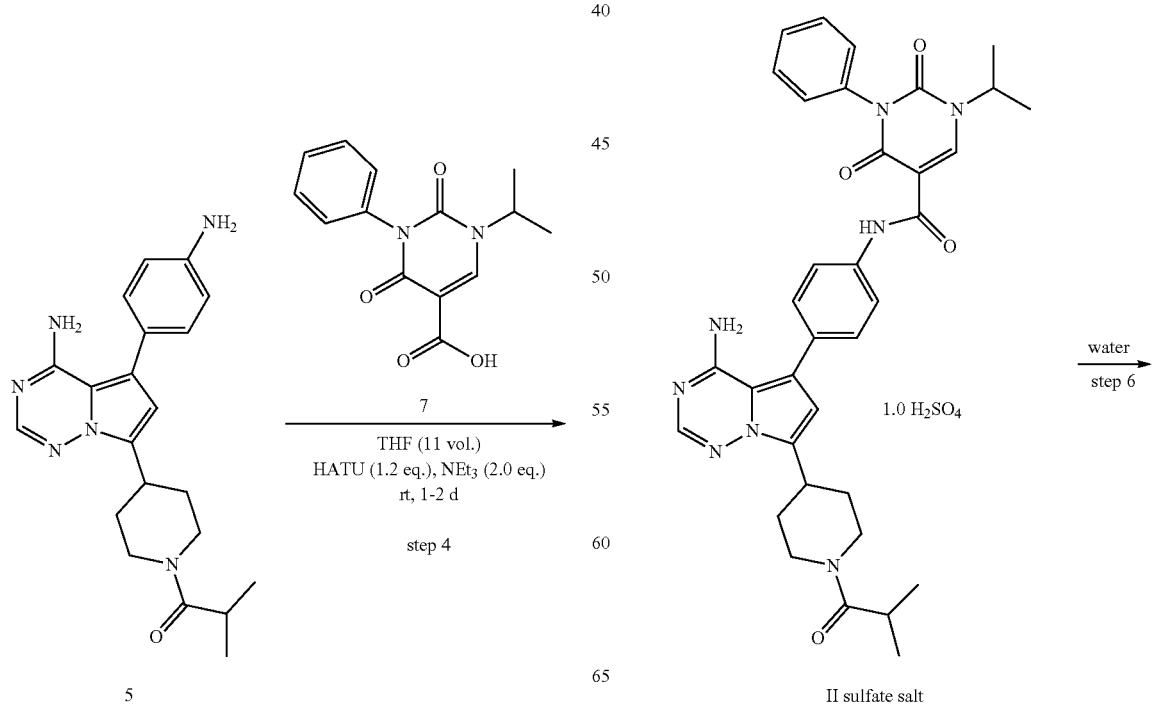

-continued

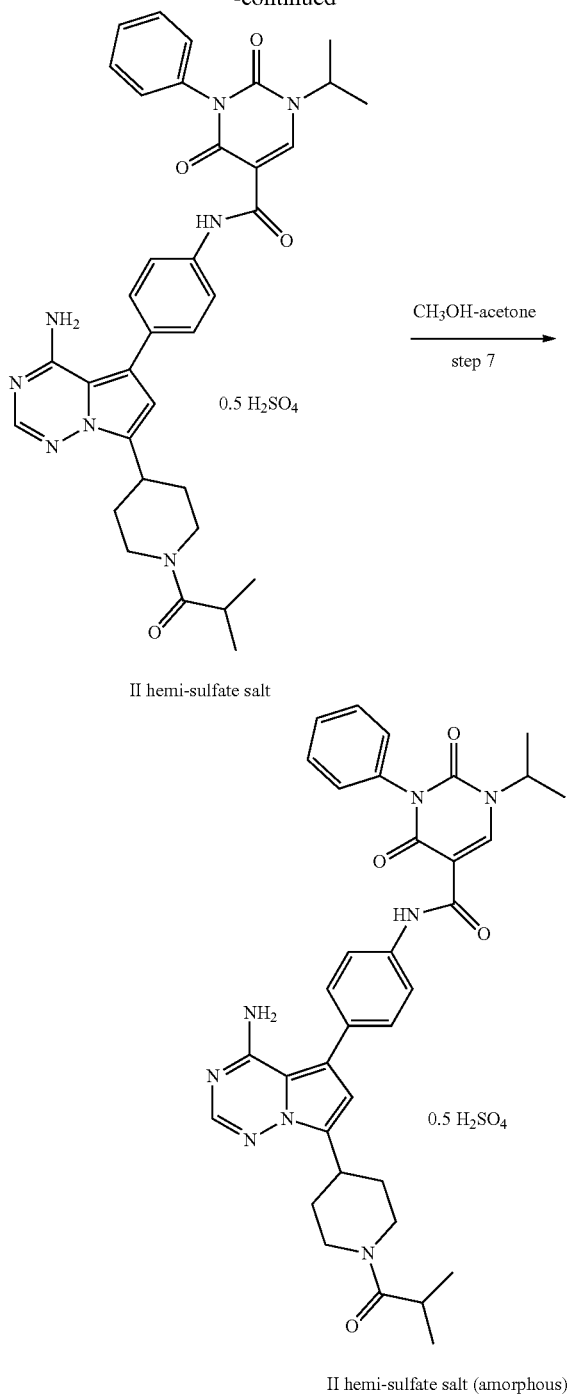

II hemi-sulfate salt

CH₃OH-acetone
step 7
0.5 H₂SO₄

II hemi-sulfate salt (amorphous)

Step 1. 5-Bromo-7-(piperidin-4-yl)pyrrolo[1,2-f][1,2,4]triazin-4-amine dihydrochloride (Compound 2)

A 5-necked 22-L round bottom flask equipped with a mechanical stirrer, a heating mantle, a thermal couple, a reflux condenser, a nitrogen inlet and a nitrogen outlet was charged with tert-butyl 4-(4-amino-5-bromopyrrolo[2,1-f][1,2,4]triazin-7-yl)piperidine-1-carboxylate (Compound 1, 880 g, 2.221 mol) in dichloromethane (DCM, 8.0 L) at room temperature. To the suspension was added hydrochloric acid in 2-propanol (5.8 N, 2.7 L, 15.66 mol, 7.05 eq.). The mixture was heated to 35° C. for 4 hours. The reaction mixture was diluted with tert-butyl methyl ether (TBME, 4.5 L) and cooled to room temperature. The slurry was filtered and washed with TBME (2.0 L). The cake was dried on the filter under vacuum for 24 hours to provide 5-bromo-7-(piperidin-4-yl)pyrrolo[1,2-f][1,2,4]triazin-4-amine dihydrochloride (Compound 2, 848 g, 103%) as a light brown solid. $^1$H NMR (400 MHz, DMSO-$d_6$) δ 9.53-9.29 (m, 3H), 8.23 (s, 1H), 6.91 (s, 1H), 3.38 (tt, J=11.8, 3.6 Hz, 1H), 3.30 (d, J=12.4 Hz, 2H), 3.00 (dtd, J=12.8, 10.1, 2.6 Hz, 2H), 2.07 (dd, J=14.1, 3.8 Hz, 2H), 1.97-1.87 (m, 2H) ppm; $^{13}$C NMR (101 MHz, DMSO-$d_6$) δ 150.34, 139.32, 138.92, 113.24, 109.67, 95.70, 43.06, 30.57, 26.89 ppm; $C_{11}H_{14}BrN_5$ (MW 295.0), LCMS (EI) m/e 296.0 (M$^+$+H).

Step 2. 1-(4-(4-Amino-5-bromopyrrolo[1,2-f][1,2,4]triazin-7-yl)piperidin-1-yl)-2-methylpropan-1-one (Compound 3)

A 5-necked 22-L round bottom flask equipped with a mechanical stirrer, a thermal couple, a reflux condenser, a nitrogen inlet and a nitrogen outlet was charged with 5-bromo-7-(piperidin-4-yl)pyrrolo[1,2-f][1,2,4]triazin-4-amine dihydrochloride (Compound 2, 1300 g, 3.522 mol) in N-methyl piperidinone (NMP, 10 L) at room temperature. To the suspension was added N,N-diisopropylethylamine (1593 g, 12.3 mol). The mixture was cooled to 10° C. and treated with isobutyryl chloride (388 g, 3.645 mol). The reaction mixture was agitated while warming to room temperature, and monitored by HPLC. Extra isobutyryl chloride (22.5 g, 0.211 mol) was added to consume all the starting material. Once the reaction was completed, the reaction mixture was filtered through a Celite pad. The resulting filtrate was cooled to 10° C. and water (26 L) was added gradually to precipitate out the product. The solids were collected by filtration, and washed by water (12 L). The cake was dried on the filter under vacuum for 48 hours to provide 1-(4-(4-amino-5-bromopyrrolo[1,2-f][1,2,4]triazin-7-yl)piperidin-1-yl)-2-methylpropan-1-one (Compound 3, 1095 g, 85%) as a light brown solid. $^1$H NMR (400 MHz, DMSO-$d_6$) δ 7.86 (s, 1H), 6.64 (s, 1H), 4.51 (d, J=12.6 Hz, 1H), 4.01 (d, J=13.2 Hz, 1H), 3.35-3.30 (m, 1H), 3.12 (t, J=12.3 Hz, 1H), 2.91-2.84 (m, 1H), 2.64 (t, J=12.1 Hz, 1H), 2.02-1.93 (m, 2H), 1.55-1.42 (m, 2H), 1.02 (d, J=6.5 Hz, 3H), 1.00 (d, J=6.5 Hz, 3H) ppm; $^{13}$C NMR (101 MHz, DMSO-$d_6$) δ 174.50, 155.68, 148.37, 135.22, 111.36, 110.65, 87.27, 45.34, 41.67, 32.91, 31.30, 30.33, 29.49, 20.03, 19.87 ppm; $C_{15}H_{20}BrN_5O$ (MW 365.09), LCMS (EI) m/e 366.1 (M$^+$+H).

Step 3. 1-(4-(4-Amino-5-(4-aminophenyl)pyrrolo[1,2-f][1,2,4]triazin-7-yl)piperidin-1-yl)-2-methylpropan-1-one (Compound 5)

A 5-necked 22-L round bottom flask equipped with a mechanical stirrer, a heating mantle, a thermal couple, a reflux condenser, a nitrogen inlet and a nitrogen outlet was charged with 1-(4-(4-amino-5-bromopyrrolo[1,2-f][1,2,4]triazin-7-yl)piperidin-1-yl)-2-methylpropan-1-one (Compound 3, 700 g, 1.911 mol), 4-(4,4,5,5-tetramethyl-1,3,2-dioxaborolan-2-yl)aniline (Compound 4, 502 g, 2.293 mol), and potassium carbonate (528 g, 3.822 mol) in 1-butanol (7.7 L) and water (1.4 L) at room temperature. The mixture was treated with chloro(2-dicyclohexylphosphino-2',4',6'-triisopropyl-1,1'-biphenyl)[2-(2'-amino-1,1'-biphenyl)]palladium(II) (XPhos Pd G2, 90 g, 115 mmol) at room temperature. The reaction mixture was degassed and refilled with nitrogen before heating up to 80° C. After two hours at 80° C., the reaction mixture was diluted with n-heptane (8 L). The resulting slurry was cooled to room temperature. The solids were collected by filtration, and washed with water (6 L). The cake was dried on the filter under vacuum for 72 hours to provide 1-(4-(4-amino-5-(4-aminophenyl) pyrrolo[1,2-f][1,2,4]triazin-7-yl)piperidin-1-yl)-2-methylpropan-1-one (Compound 5, 648 g, 90%) as a brown solid. $^1$H NMR (500 MHz, DMSO-$d_6$) δ 7.85 (s, 1H), 7.09 (d, J=8.4 Hz, 2H), 6.65 (d, J=8.4 Hz, 2H), 6.43 (s, 1H), 5.24 (s, 2H), 4.53 (d, J=12.6 Hz, 1H), 4.04 (d, J=13.1 Hz, 1H), 3.38 (ddd, J=11.8, 8.2, 3.8 Hz, 1H), 3.16 (t, J=12.7 Hz, 1H), 2.87 (p, J=6.7 Hz, 1H), 2.71-2.66 (m, 1H), 2.08-2.00 (m, 2H), 1.61-1.58 (m, 2H), 1.02 (d, J=6.5 Hz, 3H), 1.00 (d, J=6.5 Hz, 3H) ppm; $^{13}$C NMR (126 MHz, DMSO-$d_6$) δ 174.51, 156.31, 148.51, 147.65, 133.98, 130.35, 122.57, 119.37, 114.57, 109.67, 108.85, 45.48, 41.81, 32.97, 31.50, 30.56, 29.50, 20.06, 19.89 ppm; $C_{21}H_{26}N_6O$ (MW 378.48), LCMS (EI) m/e 379.2 (M$^+$+H).

Step 4. N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide (Compound II)

A 5-necked 22-L round bottom flask equipped with a mechanical stirrer, a thermal couple, a nitrogen inlet and a nitrogen outlet was charged with 1-(4-(4-amino-5-(4-aminophenyl)pyrrolo[1,2-f][1,2,4]triazin-7-yl)piperidin-1-yl)-2-methylpropan-1-one (Compound 5, 450 g, 1.189 mol), and 1-isopropyl-2,4-dioxo-3-phenyl-1,2,3,4-tetrahydropyrimidine-5-carboxylic acid (Compound 7, 342 g, 1.248 mol) in tetrahydrofuran (THF, 5 L) at room temperature. The reaction mixture was treated with triethylamine (NEt$_3$, 241 g, 2.378 mol) and then 2-(3H-[1,2,3]triazolo[4,5-b]pyridin-3-yl)-1,1,3,3-tetramethylisouronium hexafluorophosphate (V) (HATU, 565 g, 1.486 mol) in sequence. Upon the completion of the reaction, water (8 L) was added to the reaction mixture at room temperature. The solids were collected by filtration. The resulting wet cake was put back to the 22-L round bottom flask and slurried with THF (2.7 L) and water (5.4 L). The slurry was heated to 55° C., and agitated at 55° C. for two hours. The solids were collected by filtration after cooling to 30° C., and washed with water (8 L). The cake was dried on the filter under vacuum for 2 days to provide N-(4-(4-amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide (Compound II, 717 g, 95%) as a light brown solid. $^1$H NMR (500 MHz, DMSO-$d_6$) δ 11.03 (s, 1H), 8.68 (s, 1H), 8.19 (s, 1H), 7.82 (d, J=8.6 Hz, 2H), 7.55-7.46 (m, 5H), 7.38-7.36 (m, 2H), 6.85 (s, 1H), 4.79 (hept, J=6.8 Hz, 1H), 4.55 (d, J=12.3 Hz, 1H), 4.08 (d, J=12.9 Hz, 1H), 3.43 (tt, J=11.8, 3.5 Hz, 1H), 3.21 (t, J=12.4 Hz, 1H), 2.90 (hept, J=6.7 Hz, 1H), 2.70 (t, J=12.2 Hz, 1H), 2.02 (dd, J=23.0, 13.5 Hz, 2H), 1.66 (q, J=11.8, 11.3 Hz, 1H), 1.53 (q, J=12.2, 11.7 Hz, 1H), 1.44 (d, J=6.8 Hz, 6H), 1.03 (d, J=7.0 Hz, 3H), 1.01 (d, J=7.0 Hz, 3H) ppm; $^{13}$C NMR (126 MHz, DMSO-$d_6$) δ 174.55, 163.26, 160.65, 152.60, 150.48, 147.46, 142.27, 138.14, 137.56, 135.87, 130.21, 129.89, 129.50, 129.12, 129.05, 122.72, 120.55, 111.00, 108.35, 105.10, 50.94, 45.35, 41.67, 32.98, 31.40, 30.50, 29.49, 21.19 (2 —CH$_3$), 20.06, 19.89 ppm; $C_{35}H_{38}N_8O_4$ (MW 634.74), LCMS (EI) m/e 635.3 (M$^+$+H).

Step 5. N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide sulfate (Compound II Sulfate Salt)

A 5-necked 22-L round bottom flask equipped with a mechanical stirrer, a thermal couple, a nitrogen inlet and a nitrogen outlet was charged with N-(4-(4-amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide (Compound II, 713 g, 1.123 mol) in methanol (MeOH, 5.6 L) at room temperature. The mixture was heated to 55° C. and treated with a solution of sulfuric acid (H$_2$SO$_4$, 116 g, 1.179 mol) in water (1 L). After agitatation at 55° C. for 30 minutes, 2.8 L of the solvents was distilled out under reduced pressure. The reaction mixture was cooled to room temperature. The resulting solids were collected by filtration, and washed with MeOH (0.7 L). The cake was dried on the filter under vacuum for 2 days to provide N-(4-(4-amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide sulfate (Compound II sulfate salt, 744 g, 90%) as a yellow solid.

Step 6. N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide hemisulfate (Compound II Hemi-Sulfate)

A 5-necked 22-L round bottom flask equipped with a mechanical stirrer, a thermal couple, a nitrogen inlet and a nitrogen outlet was charged with N-(4-(4-amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide sulfate (sulfate salt of Compound II, 729 g, 0.995 mol) in water (16 L) at room temperature. The slurry was heated to 35° C., and agitated for 3 days. The solids were collected by filtration, and washed with water (10 L). The wet cake was dried on the filter under vacuum to provide N-(4-(4-amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide hemisulfate (Compound II hemi-sulfate salt, 644 g, 95%) as an off white solid.

Step 7. N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide hemisulfate, amorphous A 2-L round bottom flask was charged with N-(4-(4-amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide hemi-sulfate (Compound II hemi-sulfate salt, 40 g, 58.5 mmol) in acetone (500 mL) and methanol (500 mL) at room temperature. The solution was filtered through a filter paper to a 3-L single necked round bottom flask. The filtrate was concentrated to remove most of the solvents under reduced pressure. The resulting foam-like solid was dried in a vacuum oven at 50° C. under house vacuum with nitrogen sweeping to provide N-(4-(4-amino-7-(1-isobutyrylpiperidin-4-yl)pyrrolo[1,2-f][1,2,4]triazin-5-yl)phenyl)-1-isopropyl-2,4-dioxo-3-phenyl- 1,2,3,4-tetrahydropyrimidine-5-carboxamide hemisulfate (amorphous hemi-sulfate salt of Compound II, 38 g, 95%) as a light yellow solid. $^1$H NMR (400 MHz, DMSO-d$_6$) δ 11.01 (s, 1H), 8.68 (s, 1H), 8.07 (s, 1H), 7.80 (d, J=8.6 Hz, 2H), 7.55-7.45 (m, 5H), 7.38-7.36 (m, 2H), 6.74 (s, 1H), 4.79 (hept, J=6.8 Hz, 1H), 4.55 (d, J=12.3 Hz, 1H), 4.07 (d, J=13.0 Hz, 1H), 3.42 (tt, J=11.8, 3.3 Hz, 1H), 3.24-3.18 (m, 1H), 2.91 (hept, J=6.7 Hz, 1H), 2.70 (t, J=12.0 Hz, 1H), 2.07-1.99 (m, 2H), 1.68-1.51 (m, 2H), 1.44 (d, J=6.8 Hz, 6H), 1.03 (d, J=7.0 Hz, 3H), 1.01 (d, J=7.0 Hz, 3H) ppm; $^{13}$C NMR (101 MHz, DMSO-d$_6$) δ 174.55, 163.26, 160.65, 152.60, 150.48, 147.46, 142.28, 138.14, 137.56, 135.87, 130.21, 129.89, 129.50, 129.12, 129.05, 122.72, 120.55, 111.00, 108.35, 105.10, 50.94, 45.35, 41.67, 32.98, 31.40, 30.50, 29.49, 21.19 (2 —CH$_3$), 20.06, 19.89 ppm; C$_{35}$H$_{38}$N$_8$O$_4$ (MW 634.74), LCMS (EI) m/e 635.3 (M$^+$+H); Acid titration, sulfate: free base=0.50; Elemental analysis for sulfur, calculated 2.34%, observed 2.29%.

Example 3. Alternative Synthesis of N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide (Compound II)

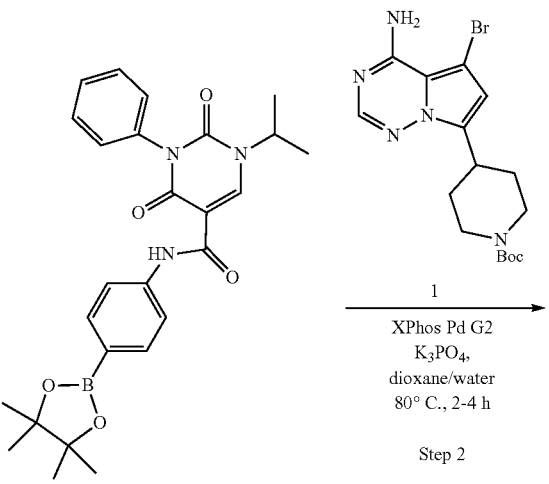

Scheme 3

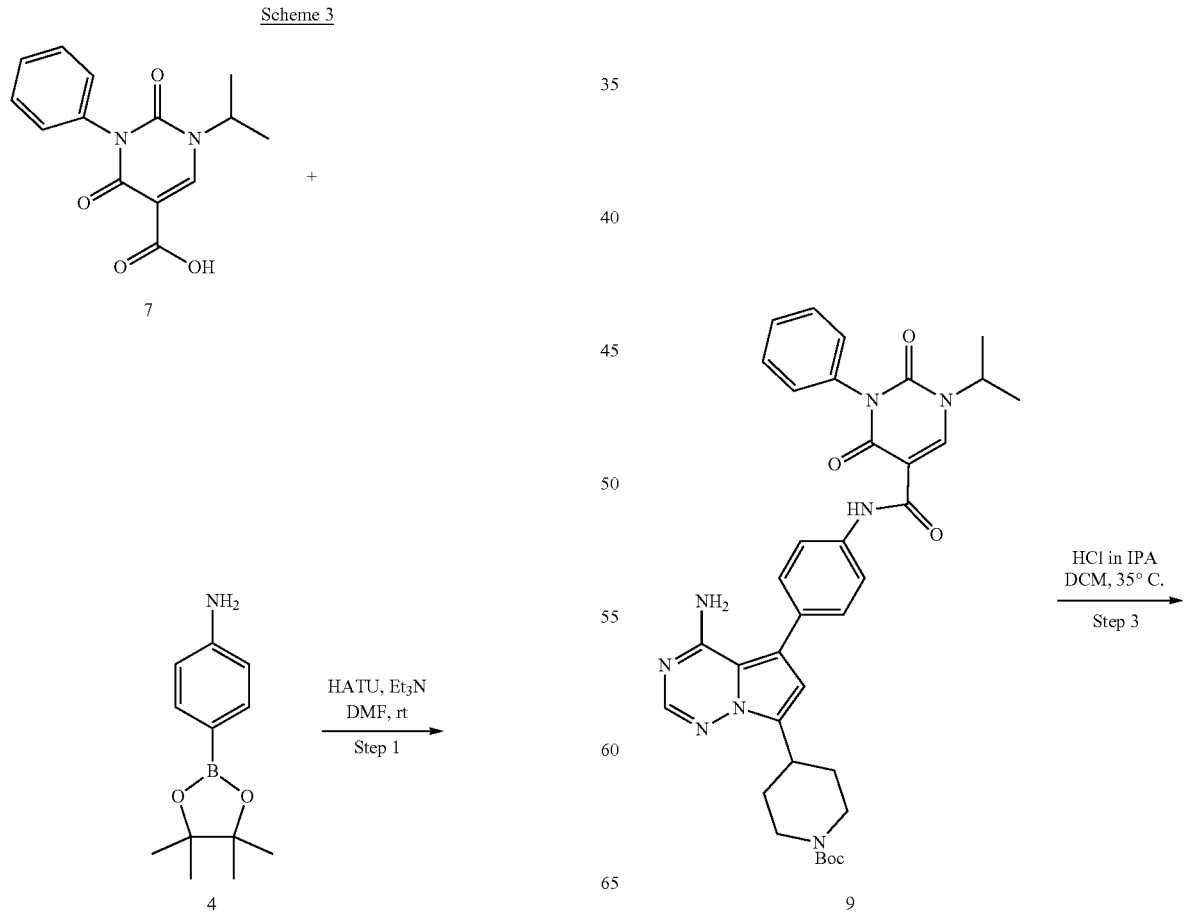

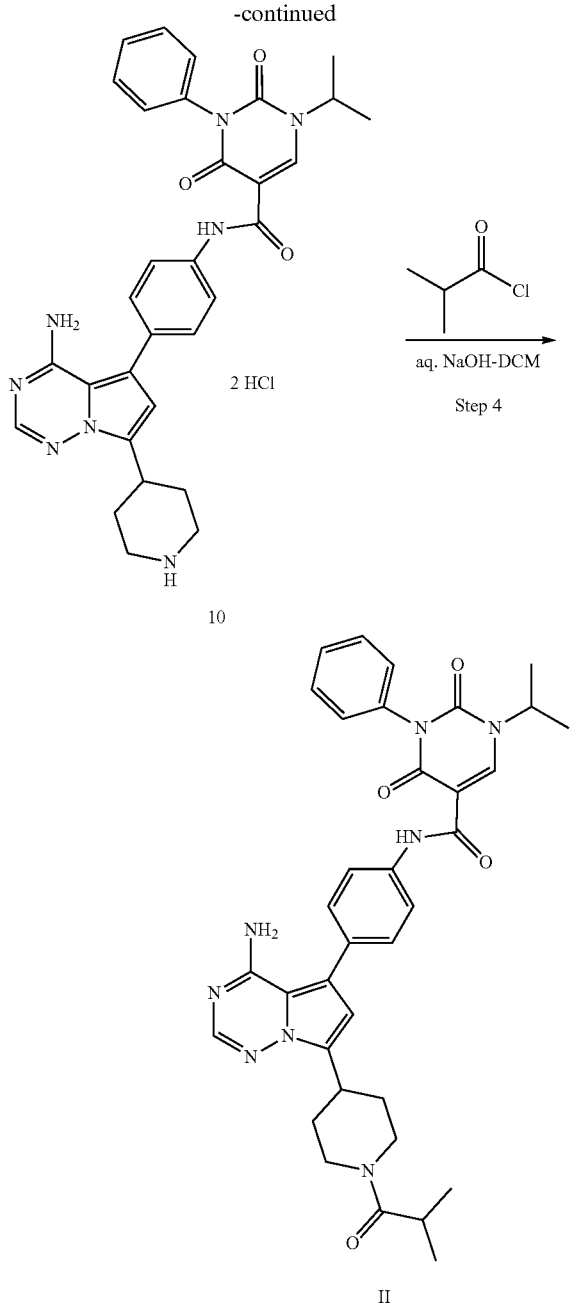

Step 1. 1-Isopropyl-2,4-dioxo-3-phenyl-N-(4-(4,4,5,5-tetramethyl-1,3,2-dioxaborolan-2-yl)phenyl)-1,2,3,4-tetrahydropyrimidine-5-carboxamide (Compound 8)

A 5-L 4-necked round bottom flask equipped with a mechanical stirrer, a thermal couple, a nitrogen inlet and nitrogen outlet was charged with 1-isopropyl-2,4-dioxo-3-phenyl-1,2,3,4-tetrahydropyrimidine-5-carboxylic acid (Compound 7, 202 g, 0.736 mol) and 4-(4,4,5,5-tetramethyl-1,3,2-dioxaborolan-2-yl)aniline (169 g, 0.773 mol) in N,N-dimethylformamide (DMF, 1.2 L) at room temperature. To the mixture was added 2-(3H-[1,2,3]triazolo[4,5-b]pyridin-3-yl)-1,1,3,3-tetramethylisouronium hexafluorophosphate (V) (HATU, 336 g, 0.884 mmol) at room temperature. Triethylamine (NEt$_3$, 97 g, 0.957 mol) was added to the mixture after cooling to an internal temperature below 15° C. The reaction mixture was then agitated at 15-25° C. for 4 hours. Water (1.2 L) was slowly added to precipitate out the product. The solids were collected by filtration, and washed with water (3×0.6 L). The cake was dried in a vacuum oven at 50° C. with a gentle nitrogen sweeping to provide 1-isopropyl-2,4-dioxo-3-phenyl-N-(4-(4,4,5,5-tetramethyl-1,3,2-dioxaborolan-2-yl)phenyl)-1,2,3,4-tetrahydropyrimidine-5-carboxamide (Compound 8, 363 g, 104%) as a white solid. $^1$H NMR (600 MHz, DMSO-d$_6$) δ 10.99 (s, 1H), 8.65 (s, 1H), 7.68-7.63 (m, 4H), 7.53-7.51 (m, 2H), 7.48-7.45 (m, 1H), 7.36 (dd, J=8.2, 1.2 Hz, 2H), 4.78 (hept, J=6.8 Hz, 1H), 1.43 (d, J=6.8 Hz, 6H), 1.29 (s, 12H) ppm; $^{13}$C NMR (150 MHz, DMSO-d$_6$) δ 163.24, 160.69, 150.46, 147.50, 141.32, 135.96, 135.83, 129.47, 129.09, 129.03, 124.09, 119.19, 105.10, 83.98, 50.89, 25.14, 21.18 ppm; $C_{26}H_{30}BN_3O_5$ (MW 475.35), LCMS (EI) m/e 476.3 (M$^+$+H).

Step 2. tert-Butyl 4-(4-amino-5-(4-(1-isopropyl-2,4-dioxo-3-phenyl-1,2,3,4-tetrahydropyrimidine-5-carboxamido)phenyl)pyrrolo[1,2-f][1,2,4]triazin-7-yl)piperidine-1-carboxylate (Compound 9)

A 22-L 5-necked round bottom flask equipped with a mechanical stirrer, a reflux condenser, a thermal couple, a heating mantle, a nitrogen inlet and a nitrogen outlet was charged with tert-butyl 4-(4-amino-5-bromopyrrolo[2,1-f][1,2,4]triazin-7-yl)piperidine-1-carboxylate (Compound 1, 557 g, 1.406 mol), 1-isopropyl-2,4-dioxo-3-phenyl-N-(4-(4,4,5,5-tetramethyl-1,3,2-dioxaborolan-2-yl)phenyl)-1,2,3,4-tetrahydropyrimidine-5-carboxamide (Compound 8, 735 g, 1.546 mol), and potassium phosphate tribasic (K$_3$PO$_4$, 597 g, 2.811 mol) in 1,4-dioxane (6.0 L) and water (1.1 L) at room temperature. The mixture was degassed and refilled with a nitrogen atmosphere. Chloro(2-dicyclohexylphosphino-2',4',6'-triisopropyl-1,1'-biphenyl)[2-(2'-amino-1,1'-biphenyl)]palladium(II) (XPhos Pd G2, 77 g, 98 mmol) was added to the reaction mixture. The reaction mixture was degassed, refilled with a nitrogen atmosphere and heated to 80° C. After 3 hours agitation at 80° C., water (6.0 L) was added to the reaction over one hour. The resulting solids were collected by filtration at 20° C., and washed with water (2×3.0 L) and n-heptane (2×2.0 L). The cake was transferred back to the 22-L round bottom flask and slurried in ethyl acetate (EtOAc, 6.0 L) and methyl tert-butylether (MTBE, 2.2 L) at room temperature. The suspension was heated to 55° C., and agitated for 2 hours. After the mixture was cooled to 20° C., the solids were collected by filtration, and washed with MTBE (2×1.0 L). The cake was dried on the filter funnel under vacuum for 2 days to provide tert-butyl 4-(4-amino-5-(4-(1-isopropyl-2,4-dioxo-3-phenyl-1,2,3,4-tetrahydropyrimidine-5-carboxamido)phenyl)pyrrolo[1,2-f][1,2,4]triazin-7-yl)piperidine-1-carboxylate (Compound 9, 827 g, 85%) as a light brown solid. $^1$H NMR (500 MHz, DMSO-d$_6$) δ 10.97 (s, 1H), 8.67 (s, 1H), 7.90 (s, 1H), 7.78 (d, J=8.6 Hz, 2H), 7.54 (t, J=7.5 Hz, 2H), 7.48-7.46 (m, 1H), 7.43 (d, J=8.6 Hz, 2H), 7.38-7.36 (m, 2H), 6.58 (s, 1H), 4.79 (hept, J=6.7 Hz, 1H), 4.08-4.03 (m, 2H), 3.34-3.28 (m, 1H), 2.89 (s, 2H), 1.99 (d, J=11.4 Hz, 2H), 1.56 (qd, J=12.7, 4.1 Hz, 2H), 1.44 (d, J=6.8 Hz, 6H), 1.42 (s, 9H) ppm; $^{13}$C NMR (126 MHz, DMSO-d$_6$) δ 163.25, 160.57, 156.20, 154.33, 150.49, 147.78, 147.40, 135.56, 135.89, 134.56, 131.20, 130.24, 129.49, 129.12, 129.03, 120.42, 117.99, 109.88, 109.35, 105.16, 79.08, 50.91, 43.90, 32.71, 30.54, 28.59, 21.11 ppm; $C_{36}H_{40}N_8O_5$ (MW 664.76), LCMS (EI) m/e 665.3 (M$^+$+H).

Step 3. N-(4-(4-Amino-7-(piperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide dihydrochloride (Compound 10)

A 22-L 5-necked round bottom flask equipped with a mechanical stirrer, a reflux condenser, a thermal couple, a heating mantle, a nitrogen inlet and a nitrogen outlet was charged with tert-butyl 4-(4-amino-5-(4-(1-isopropyl-2,4-dioxo-3-phenyl-1,2,3,4-tetrahydropyrimidine-5-carboxamido)phenyl)pyrrolo[1,2-f][1,2,4]triazin-7-yl)piperidine-1-carboxylate (Compound 9, 737 g, 1.053 mol) in dichloromethane (DCM, 4.5 L) at room temperature. To the suspension was added hydrochloric acid in 2-propanol (5.8 N in IPA, 1.474 L, 8.549 mol, 8.12 eq.). The mixture was heated to 35-40° C. After 3 hours at 35-40° C., the reaction mixture was cooled to 15° C. Water (0.4 L) was added, and the mixture was agitated at 15° C. for 1 hour. The mixture was diluted with DCM (9.0 L). The solids were collected by filtration, and washed with DCM (2×0.2 L). The cake was dried on the filter funnel under vacuum for 2 days to provide N-(4-(4-amino-7-(piperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide dihydrochloride (630 g, 94%) as a needle-like solid. $^1$H NMR (500 MHz, DMSO-d$_6$) δ 11.03 (s, 1H), 9.31-9.21 (m, 3H), 8.68 (s, 1H), 8.29 (s, 1H), 7.83 (d, J=8.7 Hz, 2H), 7.55-7.46 (m, 5H), 7.38-7.37 (m, 2H), 6.80 (s, 1H), 4.83 (hept, J=6.8 Hz, 1H), 3.50 (tt, J=11.7, 3.4 Hz, 1H), 3.35 (d, J=12.4 Hz, 2H), 3.08 (q, J=12.5 Hz, 2H), 2.18-2.15 (m, 2H), 1.99-1.96 (m, 2H), 1.44 (d, J=6.8 Hz, 6H) ppm; $^{13}$C NMR (126 MHz, DMSO-d$_6$) δ 163.26, 160.70, 150.47, 150.38, 147.52, 138.68, 138.59, 138.06, 135.86, 130.21, 129.50, 129.12, 129.05, 128.76, 126.12, 120.66, 111.81, 107.49, 105.09, 50.96, 43.19, 30.65, 27.07, 21.19 ppm; $C_{31}H_{32}N_8O_3$ (MW 564.64), LCMS (EI) m/e 565.3 (M$^+$+H).

Step 4. N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide (Compound II)

A 22-L 5-necked round bottom flask equipped with a mechanical stirrer, a thermal couple, a nitrogen inlet and a nitrogen outlet was charged with N-(4-(4-amino-7-(piperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide dihydrochloride (608 g, 0.954 mol) in dichloromethane (DCM, 17.6 L) at room temperature. To the suspension was added sodium hydroxide aqueous solution (NaOH, 1 N, 3.815 L, 3.815 mol). After agitatation at room temperature for 1 hour, the mixture was cooled to 0-5° C. and treated with isobutyryl chloride (107 g, 1.001 mol). The reaction mixture was agitated at room temperature for 24 hours. Upon the completion of the reaction, the mixture was filtered through a Celite pad. The organic phase was separated, washed with water (2×2.5 L), and concentrated under reduced pressure. To the residue was added DCM (2.4 L) and methyl tert-butylether (MTBE, 9.7 L). The mixture was heated to 50° C., and agitated for 1 hour. After cooling to room temperature, the resulting solids were collected by filtration. The cake was dried on the filter under vacuum for 24 hours to provide N-(4-(4-amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide (Compound II, 548 g, 91%) as a light yellow solid. $^1$H NMR (500 MHz, DMSO-d$_6$) δ 11.03 (s, 1H), 8.68 (s, 1H), 8.19 (s, 1H), 7.82 (d, J=8.6 Hz, 2H), 7.55-7.46 (m, 5H), 7.38-7.36 (m, 2H), 6.85 (s, 1H), 4.79 (hept, J=6.8 Hz, 1H), 4.55 (d, J=12.3 Hz, 1H), 4.08 (d, J=12.9 Hz, 1H), 3.43 (tt, J=11.8, 3.5 Hz, 1H), 3.21 (t, J=12.4 Hz, 1H), 2.90 (hept, J=6.7 Hz, 1H), 2.70 (t, J=12.2 Hz, 1H), 2.02 (dd, J=23.0, 13.5 Hz, 2H), 1.66 (q, J=11.8, 11.3 Hz, 1H), 1.53 (q, J=12.2, 11.7 Hz, 1H), 1.44 (d, J=6.8 Hz, 6H), 1.03 (d, J=7.0 Hz, 3H), 1.01 (d, J=7.0 Hz, 3H) ppm; $^{13}$C NMR (126 MHz, DMSO-d$_6$) δ 174.55, 163.26, 160.65, 152.60, 150.48, 147.46, 142.27, 138.14, 137.56, 135.87, 130.21, 129.89, 129.50, 129.12, 129.05, 122.72, 120.55, 111.00, 108.35, 105.10, 50.94, 45.35, 41.67, 32.98, 31.40, 30.50, 29.49, 21.19 (2 —CH$_3$), 20.06, 19.89 ppm; $C_{35}H_{38}N_8O_4$ (MW 634.74), LCMS (EI) m/e 635.3 (M$^+$+H).

Example 4. Synthesis of tert-Butyl 4-(4-amino-5-bromopyrrolo[1,2-f][1,2,4]triazin-7-yl)piperidine-1-carboxylate (Compound 1 of Schemes 1 and 2)

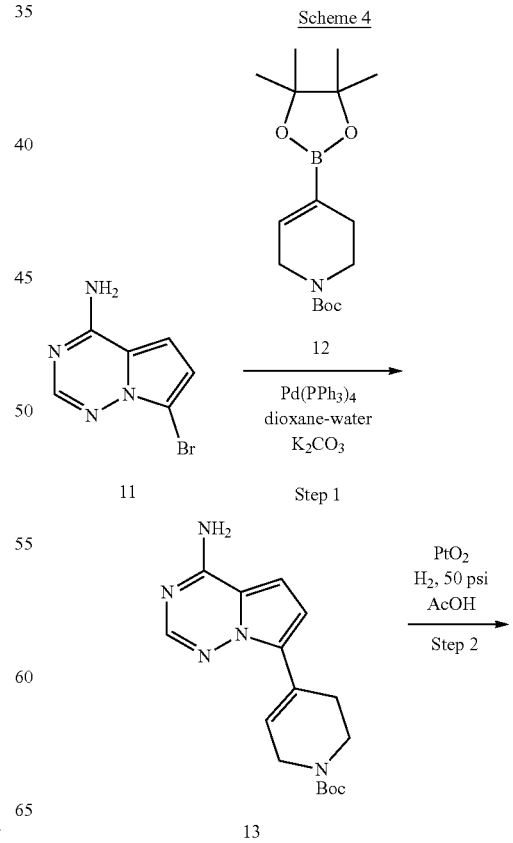

Scheme 4

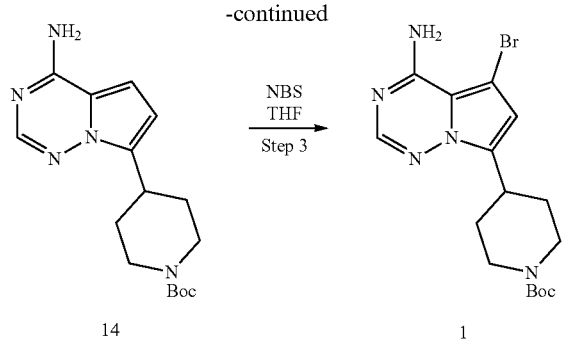

Step 1. tert-Butyl 4-(4-aminopyrrolo[1,2-f][1,2,4]triazin-7-yl)-5,6-dihydropyridine-1(2H)-carboxylate (Compound 13)

A 3-L round bottom flask equipped with a mechanical stirrer, a heating mantle, a thermal couple, a reflux condenser, a nitrogen inlet and a nitrogen outlet was charged with 7-bromopyrrolo[1,2-f][1,2,4]triazin-4-amine (Compound 11, 100 g, 469 mmol) and tert-butyl 4-(4,4,5,5-tetramethyl-1,3,2-dioxaborolan-2-yl)-5,6-dihydropyridine-1(2H)-carboxylate (Compound 12, 174 g, 563 mmol) in 1,4-dioxane (876 mL) at room temperature. To the reaction flask was added potassium carbonate (130 g, 939 mmol) and water (218 g) in sequence. The mixture was degassed by exposure to vacuum and refilled with nitrogen atmosphere for three times. After the addition of tetrakis(triphenylphosphine)palladium (0) (Pd(PPh$_3$)$_4$, 13.56 g, 11.7 mmol), the reaction mixture was degassed and refilled with nitrogen for three times at room temperature. Then the reaction mixture was heated to 85-90° C., and agitated at that temperature for 16 hours. Upon the completion of the reaction, water (900 mL) was added in 30 minutes while the internal temperature was above 50° C. The mixture was cooled to room temperature. Solids gradually precipitated out. The solids were collected by filtration at 18° C., and washed with water (2×250 mL) and methyl tert-butyl ether (MTBE, 3×200 mL). The wet cake was put back into the reaction flask, and agitated in MTBE (750 mL) at 50° C. for 1 hour. The solids were collected at room temperature by filtration. The cake was dried in a vacuum oven at 50° C. under vacuum with nitrogen sweeping for 72 hours to provide tert-butyl 4-(4-aminopyrrolo[1,2-f][1,2,4]triazin-7-yl)-5,6-dihydropyridine-1(2H)-carboxylate (Compound 13, 123.7 g, 84%) as a brown solid. $^1$H NMR (500 MHz, DMSO-d$_6$) δ 7.89 (s, 1H), 7.69 (s, 2H), 7.00 (s, 1H), 6.91 (d, J=4.6 Hz, 1H), 6.69 (d, J=4.5 Hz, 1H), 4.06 (s, 2H), 3.55 (t, J=5.5 Hz, 2H), 2.59-2.52 (m, 2H), 1.43 (s, 9H) ppm; C$_{16}$H$_{21}$N$_5$O$_2$ (MW 315.37), LCMS (EI) m/e 316.1 (M$^+$+H).

Step 2. tert-Butyl 4-(4-aminopyrrolo[1,2-f][1,2,4]triazin-7-yl)piperidine-1-carboxylate (Compound 14)

A 2-L flask was charged with tert-butyl 4-(4-aminopyrrolo[1,2-f][1,2,4]triazin-7-yl)-5,6-dihydropyridine-1(2H)-carboxylate (Compound 13, 50.0 g, 159 mmol) and platinum (IV) oxide (10.0 g, 44 mmol) in acetic acid (1000 mL) at room temperature. The flask was put on a Parr Shaker with hydrogen gas at 50 psi. After 16 hours, the reaction mixture was filtered through a Celite pad (50 g), and washed with methanol (500 mL). The filtrate was concentrated under reduced pressure. To the residue was added methyl tert-butyl ether (MTBE, 600 mL) at room temperature. A solution of potassium carbonate (about 50 g) in water (1200 mL) was added to the MTBE solution to adjust the pH value to 6-7. The solids were collected by filtration, and washed with water (2×300 mL) and n-heptane (2×300 mL). The cake was dried in a vacuum oven at 50° C. under vacuum with nitrogen sweeping for 16 hours to provide tert-butyl 4-(4-aminopyrrolo[1,2-f][1,2,4]triazin-7-yl)piperidine-1-carboxylate (Compound 14, 49.3 g, 98%) as a light brown solid. $^1$H NMR (500 MHz, DMSO-d$_6$) δ 7.82 (s, 1H), 7.59 (s, 2H), 6.81 (d, J=4.4 Hz, 1H), 6.44 (d, J=4.3 Hz, 1H), 4.05 (d, J=11.3 Hz, 2H), 3.25 (tt, J=11.8, 3.3 Hz, 1H), 2.88 (s, 2H), 1.95 (d, J=11.9 Hz, 2H), 1.51 (qd, J=12.6, 4.0 Hz, 2H), 1.42 (s, 9H) ppm; C$_{16}$H$_{23}$N$_5$O$_2$ (MW 317.39), LCMS (EI) m/e 318.1 (M$^+$+H).

Step 3. tert-Butyl 4-(4-amino-5-bromopyrrolo[1,2-f][1,2,4]triazin-7-yl)piperidine-1-carboxylate (Compound 1)

A 5-necked 22-L round bottom flask equipped with a mechanical stirrer, a thermal couple, a reflux condenser, a nitrogen inlet and a nitrogen outlet was charged with tert-butyl 4-(4-aminopyrrolo[1,2-f][1,2,4]triazin-7-yl)piperidine-1-carboxylate (Compound 14, 730 g, 2.30 mol) in tetrahydrofuran (THF, 14.0 L) at room temperature. The mixture was cooled to 0-5° C. To the reaction mixture was added N-bromosuccinimide (NBS, 409 g, 2.30 mol) in 5 minutes while the internal temperature was maintained below 15° C. After 1 hour of agitation at below 10° C., some solvents (9.0 L) were removed under reduced pressure. To the residual solution was addeded a solution of sodium bicarbonate (140 g, 1.67 mol) in water (14.0 L) over 5 minutes. Solids precipitated out. The solids were collected by filtration, and washed with water (7.0 L) and n-heptane (4 L). The wet cake was dried on the filter under house vacuum for 48 hours to provide tert-butyl 4-(4-amino-5-bromopyrrolo[1,2-f][1,2,4]triazin-7-yl)piperidine-1-carboxylate (Compound 1, 886 g, 97%) as a brown solid. $^1$H NMR (400 MHz, DMSO-d$_6$) δ 7.86 (s, 1H), 6.66 (s, 1H), 4.04 (d, J=11.0 Hz, 2H), 3.30-3.23 (m, 1H), 2.86 (br.s, 2H), 1.92 (d, J=12.4 Hz, 2H), 1.50 (qd, J=12.8, 4.1 Hz, 2H), 1.41 (s, 9H) ppm; $^{13}$C NMR (101 MHz, DMSO-d$_6$) δ 155.68, 154.29, 148.35, 135.37, 111.31, 110.68, 87.29, 79.10, 43.97, 32.63, 30.37, 28.58 ppm; C$_{16}$H$_{22}$BrN$_5$O$_2$ (MW 395.10), LCMS (EI) m/e 396.1 (M$^+$+H).

Example 5. Synthesis of 1-Isopropyl-2,4-dioxo-3-phenyl-1,2,3,4-tetrahydropyrimidine-5-carboxylic acid (Compound 7 of Schemes 2 and 3)

Step 1: Diethyl 2-((3-phenylureido)methylene)malonate

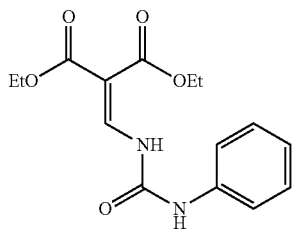 [SMILES: CCOC(=O)C(=CNC(=O)Nc1ccccc1)C(=O)OCC]

To a mixture of diethyl (aminomethylene)malonate (6.0 g, 32 mmol) and phenyl isocyanate (3.8 mL, 35 mmol) in 1,2-dichloroethane (20 mL) at rt was added N,N-diisopropylethylamine (7.2 mL, 42 mmol). The reaction mixture was then stirred at 70° C. overnight, cooled to rt, added Et₂O (50 mL), and stirred for another 30 min. The resulting solid was collected by filtration, washed with ether, and dried to give the product as a white solid (4.88 g, 50%). LCMS calcd for C₁₅H₁₉N₂O₅ (M+H)⁺: m/z=307.1. Found: 307.2.

Step 2: Ethyl 2,4-dioxo-3-phenyl-1,2,3,4-tetrahydropyrimidine-5-carboxylate

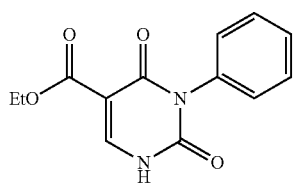 [SMILES: CCOC(=O)c1c[nH]c(=O)n(-c2ccccc2)c1=O]

A mixture of diethyl 2-((3-phenylureido)methylene)malonate from previous step (4.88 g, 15.9 mmol) and 2.5 M NaOEt in EtOH (13 mL, 32 mmol) in EtOH (20 mL) was stirred at rt for 1 h. The resulting mixture was diluted with EtOAc, washed/acidified with 1 N citric acid, washed with water, brine, dried over Na₂SO₄, and concentrated to provide the crude product as a white solid, which was used directly in the next step (4.1 g, 99%). LCMS calcd for C₁₃H₁₃N₂O₄ (M+H)⁺: m/z=261.1. Found: 261.1.

Step 3: ethyl 1-isopropyl-2,4-dioxo-3-phenyl-1,2,3,4-tetrahydropyrimidine-5-carboxylate

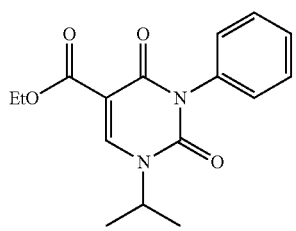 [SMILES: CCOC(=O)c1cn(C(C)C)c(=O)n(-c2ccccc2)c1=O]

A mixture of ethyl 2,4-dioxo-3-phenyl-1,2,3,4-tetrahydropyrimidine-5-carboxylate from previous step (1.50 g, 5.76 mmol), isopropyl iodide (1.2 mL, 12 mmol), and Cs₂CO₃ (5.6 g, 17 mmol) in DMF (20 mL) was stirred at 50° C. for 5 h. The reaction mixture was then cooled to rt, diluted with EtOAc, washed with water, brine, dried over Na₂SO₄, and concentrated to provide the crude product, which was used directly in the next step. LCMS calcd for C₁₆H₁₉N₂O₄ (M+H)⁺: m/z=303.1. Found: 303.1.

Step 4: 1-Isopropyl-2,4-dioxo-3-phenyl-1,2,3,4-tetrahydropyrimidine-5-carboxylic acid

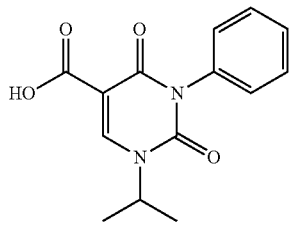 [SMILES: CC(C)n1cc(C(=O)O)c(=O)n(-c2ccccc2)c1=O]

A mixture of ethyl 1-isopropyl-2,4-dioxo-3-phenyl-1,2,3,4-tetrahydropyrimidine-5-carboxylate from previous step (1.70 g, 5.62 mmol) in 4.0 M HCl in 1,4-dioxane (9.8 mL, 39 mmol) and water (2.1 mL) was stirred at 60° C. for 4 h, cooled to rt, and added water. The resulting solid was then collected by filtration (washed with water) to give the product as a white solid (1.1 g, 71%). LCMS calcd for C₁₄H₁₅N₂O₄ (M+H)⁺: m/z=275.1. Found: 275.1.

Example 6. Synthesis of 1-Isopropyl-2,4-dioxo-3-(pyridin-2-yl)-1,2,3,4-tetrahydropyrimidine-5-carboxylic acid (Compound 6 of Scheme 1)

Step 1: Diethyl 2-((3-pyridin-2-ylureido)methylene)malonate

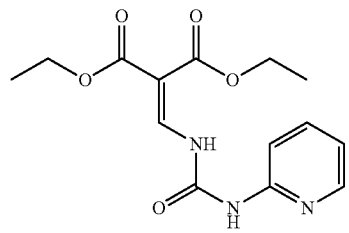 [SMILES: CCOC(=O)C(=CNC(=O)Nc1ccccn1)C(=O)OCC]

To a mixture of diethyl 2-(aminomethylene)malonate (3.0 g, 16.0 mmol) and 2-isocyanatopyridine (2.02 g, 16.8 mmol) in 1,2-dichloroethane (9.0 mL) at rt was added N,N-diisopropylethylamine (3.6 mL, 20.8 mmol). The reaction mixture was then stirred at 70° C. overnight, cooled to rt, and directly purified via column chromatography (0% to 15% MeOH in CH₂Cl₂) to give the product (3.18 g, 65%). LCMS calcd for C₁₄H₁₈N₃O₅ (M+H)⁺: m/z=308.1. Found: 308.1.

Step 2: 1-Isopropyl-2,4-dioxo-3-(pyridin-2-yl)-1,2,3,4-tetrahydropyrimidine-5-carboxylic acid

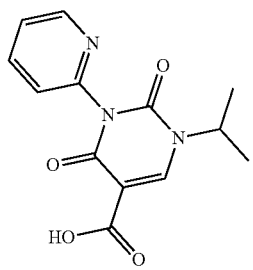 [SMILES: CC(C)n1cc(C(=O)O)c(=O)n(-c2ccccn2)c1=O]

A mixture of diethyl 2-((3-(pyridin-2-yl)ureido)methylene)malonate (3.18 g, 10.4 mmol) and 2.5 M NaOEt in EtOH (6.2 mL, 15.5 mmol) in EtOH (25 mL) was stirred at rt for 3 h. The resulting mixture was diluted with EtOAc, and washed/acidified with 1 N citric acid solution (30 mL). The organic layer was separated, and the aqueous layer was further extracted with 3:1 $CHCl_3$/isopropyl alcohol (30 mL×3). The combined organic layers were dried over $Na_2SO_4$, and concentrated to provide the crude product, ethyl 2,4-dioxo-3-(pyridin-2-yl)-1,2,3,4-tetrahydropyrimidine-5-carboxylate, which was used directly in the next step. LCMS calcd for $C_{12}H_{12}N_3O_4$ $(M+H)^+$: m/z=262.1. Found: 262.2.

A mixture of crude ethyl 2,4-dioxo-3-(pyridin-2-yl)-1,2,3,4-tetrahydropyrimidine-5-carboxylate from previous step, 2-iodopropane (2.06 mL, 20.7 mmol), and $Cs_2CO_3$ (10.1 g, 31.0 mmol) in DMF (35 mL) was stirred at 70° C. for 3 h. The reaction mixture was then cooled to rt, diluted with 3:1 $CHCl_3$/isopropyl alcohol (75 mL), washed with water, brine, dried over $Na_2SO_4$, and concentrated to afford the crude product, ethyl 1-isopropyl-2,4-dioxo-3-(pyridin-2-yl)-1,2,3,4-tetrahydropyrimidine-5-carboxylate, which was used directly in the next step. LCMS calcd for $C_{15}H_{18}N_3O_4$ $(M+H)^+$: m/z=304.1. Found: 304.1.

A mixture of crude ethyl 1-isopropyl-2,4-dioxo-3-(pyridin-2-yl)-1,2,3,4-tetrahydropyrimidine-5-carboxylate from previous step in 4 M HCl in 1,4-dioxane (20 mL, 82 mmol) and water (5.0 mL) was stirred at 80° C. for 5 h, cooled to rt, and concentrated. The resulting material was then purified via column chromatography (0% to 15% MeOH in $CH_2Cl_2$) to give the product as a slightly yellow solid (1.50 g, 47% three steps). LCMS calcd for $C_{13}H_{14}N_3O_4$ $(M+H)^+$: m/z=276.1. Found: 276.1.

Example 7. Solid State Characterization of N-(4-(4-Amino-7-(1-isobutyrylpiperidin-4-yl)pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide maleate (Compound I Maleate Salt, Form I)

X-Ray Powder Diffraction (XRPD) of Compound I Maleate Salt

The X-Ray Powder Diffraction (XRPD) was obtained from Rigaku MiniFlex X-ray Powder Diffractometer (XRPD). The general experimental procedures for XRPD were: (1) X-ray radiation from copper at 1.054056 Å with $K_\beta$ filter; (2) X-ray power at 30 KV, 15 mA; and (3) the sample powder was dispersed on a zero-background sample holder. The general measurement conditions for XRPD were: Start Angle 3 degrees; Stop Angle 45 degrees; Sampling 0.02 degrees; and Scan speed 2 degree/min. The XRPD pattern is shown in FIG. 1 and the XRPD data are provided in Table 1.

TABLE 1

XRPD Data: Maleate Salt of the Compound of Formula I (Form I)

| 2-Theta (°) | Height | H % |
|---|---|---|
| 4.3 | 5452 | 89.8 |
| 5.8 | 63 | 1.0 |
| 8.4 | 6068 | 100 |
| 12.6 | 177 | 2.9 |
| 13.2 | 331 | 5.5 |
| 15.8 | 120 | 2.0 |
| 17.1 | 132 | 2.2 |
| 18.5 | 230 | 3.8 |
| 20.3 | 136 | 2.2 |
| 20.9 | 89 | 1.5 |
| 23.1 | 114 | 1.9 |
| 24.0 | 118 | 1.9 |
| 25.2 | 137 | 2.3 |
| 28.4 | 45 | 0.7 |
| 29.7 | 44 | 0.7 |
| 31.5 | 59 | 1.0 |
| 35.7 | 102 | 1.7 |
| 42.6 | 40 | 0.7 |

Differential Scanning Calorimetry (DSC) of Compound I Maleate Salt (Form I)

The DSC was obtained from TA Instruments Differential Scanning calorimetry, Model Q200 with autosampler. The DSC instrument conditions were as follows: 30-300° C. at 10° C./min; Tzero aluminum sample pan and lid; and nitrogen gas flow at 50 mL/min. The DSC thermogram is shown in FIG. 2. The DSC thermogram revealed a major endothermal event at an onset temperature of 202.9° C. with a peak temperature of 211.0° C. which is believed to be the melting and decomposition temperature of the compound.

Thermogravimetric Analysis (TGA) of Compound I Maleate Salt (Form I)

The TGA was obtained from TA Instrument Thermogravimetric Analyzer, Model Q500. The general experimental conditions for TGA were: ramp from 20° C. to 600° C. at 20° C./min; nitrogen purge, gas flow at 40 mL/min followed by balance of the purge flow; sample purge flow at 60 mL/min; platinum sample pan. The TGA thermogram is shown in FIG. 3. A weight loss of about 0.7% up to 150° C. was observed and believed to be associated with the loss of moisture and residual solvents. The compound starts to decompose significantly at above 200° C.

Solubility of Compound I Maleate Salt (Form I)

The solubility of the Compound I maleate salt was measured at 25±1° C. and at 50±1° C. The general procedure for testing the solubility at 25±1° C. is as follows: 1) 3 mL of each of the solvents listed in Table 1A were added to individual vials; 2) Compound I maleate salt was added to form a cloudy solution at 25° C.; 3) another 15-20 mg of Compound I maleate salt was added; 4) the mixture was agitated at 25±1° C. for 48 hours; 5) the supernatant was filtered using a syringe filter; and 6) the saturated solution was diluted with MeOH and analyzed by HPLC. The general procedure for testing the solubility at 50±1° C. is as follows: 1) 3 mL of each of the solvents listed in Table 1A were added to individual vials; 2) Compound I maleate salt was added to form a cloudy solution at 50° C.; 3) another 20-25 mg of Compound I maleate salt was added; 4) the mixture was agitated at 50±1° C. for 24 hours; 5) the supernatant was filtered using a warmed syringe filter at 50±1° C.; and 6) the saturated solution was diluted with MeOH and analyzed by HPLC. The results are summarized in Table 1A.

TABLE 1A

| Entry | Solvent | Solubility at 25° C. (mg/mL) | Solubility at 50° C. (mg/mL) |
|---|---|---|---|
| 1 | MeCN | 0.28 | 0.68 |
| 2 | Chloroform | 6.12 | 13.74 |
| 3 | Dichloromethane | 24.35 | 33.70 |

TABLE 1A-continued

| Entry | Solvent | Solubility at 25° C. (mg/mL) | Solubility at 50° C. (mg/mL) |
|---|---|---|---|
| 4 | DMF | >50 | >50 |
| 5 | 1,4-Dioxane | 2.31 | 4.62 |
| 6 | Methanol | 1.64 | 3.09 |
| 7 | 2-Methoxyethanol | 5.96 | 14.75 |
| 8 | MIBK | 0.43 | 0.74 |
| 9 | Toluene | 0.18 | 0.20 |
| 10 | Hexane | 0.00 | 0.00 |
| 11 | THF | 0.92 | 1.63 |
| 12 | Acetone | 1.68 | 3.05 |
| 13 | n-BuOH | 0.21 | 1.10 |
| 14 | MTBE | 0.08 | 0.1 |
| 15 | DMSO | >50 | >50 |
| 16 | EtOH | 0.65 | 1.93 |
| 17 | EtOAc | 0.18 | 0.40 |
| 18 | Ethyl formate | 0.68 | 0.99 |
| 19 | Heptane | 0.00 | 0.00 |
| 20 | IPAc | 0.27 | 0.33 |
| 21 | 1-Propanol | 0.44 | 1.31 |
| 22 | IPA | 0.16 | 0.68 |
| 23 | Water | 0.02 | 0.04 |
| 24 | MEK | 0.28 | 2.19 |
| 25 | 2% DCM/ 98% MeOH (V/V) | 1.46 | N/A |
| 26 | 10% DCM/ 90% MeOH (V/V) | 1.88 | N/A |
| 27 | DCM/MeOH(2/1) | >50 | N/A |

Other Crystalline Salts

Other crystalline salts of the compound of Formula I such as HCl salt, mono-sulfate salt, hemi-sulfate salt, mesylate salt, and besylate salt have been discovered and prepared.

Example 8: Preparation of Salts of N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide (Salts of Compound II)

Salts of Compound II were prepared according to the procedures in Table 2 below. These salts were analyzed by XRPD, DSC and TGA (see Examples 9-15).

TABLE 2

| Salt | Procedures |
|---|---|
| Phosphate | 60.94 mg of Compound II free base was combined with 2.4 mL of the mixture of methanol/DCM (1:2) and stirred to give a clear solution. Phosphoric acid in IPA (0.115 mL, 0.115 mmol, 1.20 eq.) was added and the solution was stirred at room temperature for 5 h. The solvent was concentrated to a total volume of about 1.0 mL to give a slurry which was stirred at 65° C. for 120 min. The slurry was cooled to room temperature (20-21° C.) and stirred for 2 h. The slurry was filtered and washed with MTBE. The solid was dried at 43-45° C. under vacuum overnight. Weight: 58.2 mg (82.7%). The stoichiometric ratio for the salt between Compound II free base and phosphoric acid was determined by elemental analysis and wt % by HPLC as 1:1. XRPD (see Example 9, FIG. 4), DSC (Example 9, FIG. 5), and TGA (Example 9, FIG. 6) |
| Maleate | 51.74 mg of Compound II free base was combined with 1.5 mL of DCM and 0.5 mL of MeOH and stirred to give a clear solution. Maleic acid (14.19 mg, 0.12 mmol, 1.50 eq.) was added and the solution was stirred at room temperature for 2 h. Solvent was concentrated at 43-44° C. to a total volume of about 0.5 mL. The mixture was cooled to room temperature and stirred for 2 h. 1.5 mL IPA was added and the slurry stirred for stirred 2-3 min. The slurry was filtered and washed with MTBE. The solid was dried at 43-45° C. under vacuum overnight. Weight: 56 mg (91.5%). The stoichiometric ratio for the salt between Compound II free base and maleic acid was determined by $^1$H NMR as 1:1. XRPD (see Example 10, FIG. 7), DSC (see Example 10, FIG. 8), and TGA (see Example 10, FIG. 9) |
| Hemi-Sulfate | 87.70 mg of Compound II free base was combined with 2.4 mL of MeOH and 1.2 mL of DCM and stirred for 20 min to give an almost clear solution. Sulfuric acid in water (0.083 mL, 0.083 mmol, 1M in water, 0.6 eq.) was added and the solution was stirred at room temperature for 2 min to give a clear solution. The solution was further stirred for 30 min and the solvent was then concentrated to a volume of about 1.1 mL to give a slurry. The mixture was further stirred 70° C. for 1.0 h and 65° C. for 1.0 h. The slurry was cooled to room temperature (19-20° C.) and stirred for 1 h. The slurry was filtered and washed with MTBE. The solid was dried at 43-45° C. under vacuum overnight. Weight: 75.74 mg (80.2%). The stoichiometric ratio for the salt between Compound II free base and sulfuric acid was determined by elemental analysis as 2:1. XRPD (see Example 11, FIG. 10), DSC (see Example 11, FIG. 11), and TGA (see Example 11, FIG. 12) |
| Hydrochloride | 76.25 mg of Compound II free base was combined with 2.0 mL of a mixture of methanol/DCM (1:2) and stirred to give a clear solution. Hydrochloric acid in IPA (0.14 mL, 0.14 mmol, 1.17 eq.) was added and the solution was stirred at room temperature for 3 h. 1.5 mL of IPA was added and the solvent was then concentrated to a volume of about 1.4 mL at 67-68° C. to give a slurry. 0.8 mL of ethyl alcohol was added and the slurry stirred at 76-78° C. for 2 h. The slurry was cooled to room temperature (19-20° C.) and stirred for 1 h. The slurry was filtered and washed with MTBE. The solid was dried at 43-45° C. under vacuum overnight. Weight: 72 mg (89.30%). The stoichiometric ratio of the salt between Compound II free base and |

TABLE 2-continued

| Salt | Procedures |
|---|---|
| | hydrochloric acid was determined as 1:1 by wt % by HPLC and elemental analysis. XRPD (see Example 12, FIG. 13), DSC (see Example 12, FIG. 14) and TGA (see Example 12, FIG. 15) |
| Salicylate | 60.94 mg of Compound II free base was combined with 2.4 mL of a mixture of methanol/DCM (1:2) and stirred to give a clear solution. Salicylic acid (16.3 mg, 0.115 mmol, 1.20 eq.) was added and the solution was stirred at room temperature for 2 h. The solvent was concentrated to a volume of about 1.0 mL. 0.8 mL of IPA was added and the slurry was stirred at 65° C. for 120 min. The slurry was cooled to room temperature (19-20° C.) and stirred for 2 h. The slurry was filtered and washed with MTBE. The solid was dried at 43-45° C. under vacuum overnight. Weight: 55.7 mg (79.4%). The stoichiometric ratio for the salt between Compound II free base and salicylic acid was determined by $^1$H NMR as 1:1. XRPD (see Example 13, FIG. 16), DSC (see Example 13, FIG. 17), and TGA (see Example 13, FIG. 18) |
| Mesylate | The procedure to prepare the mesylate salt of Compound II was similar to that used in the preparation of the phosphate salt. 1.2 mL of Compound II free base (0.04M, 30.47 mg, 0.048 mmol, 1.0 eq.) in DCM/MeOH (2:1) was combined with methanesulfonic acid (0.05 mL, 1M in IPA, 1.04 eq.). The stoichiometric ratio for the salt between Compound II free base and methanesulfonic acid was determined by 1H NMR as 1:1. XRPD (see Example 14, FIG. 19), DSC (see Example 14, FIG. 20), and TGA (see Example 14, FIG. 21) |
| Esylate | The procedure to prepare the mesylate salt of Compound II was similar to that used in the preparation of the phosphate salt. 1.2 mL of Compound II free base (0.04M, 30.47 mg, 0.048 mmol, 1.0 eq.) in DCM/MeOH (2:1) ) was combined with ethanesulfonic acid (0.10 mL, 0.5M in IPA, 1.04 eq.). The stoichiometric ratio for the salt between Compound II free base and ethanesulfonic acid was determined by 1H NMR as 1:1. XRPD (see Example 15, FIG. 22), DSC (see Example 15, FIG. 23), and TGA (see Example 15, FIG. 24) |

Example 9. Solid State Characterization of Compound II Phosphate

X-Ray Powder Diffraction (XRPD) Studies for Compound II Phosphate

The phosphate salt of Compound II was characterized by XRPD. The XRPD was obtained from Rigaku MiniFlex X-ray Powder Diffractometer (XRPD). The general experimental procedures for XRPD were: (1) X-ray radiation from copper at 1.054056 Å with $K_\beta$ filter; (2) X-ray power at 30 KV, 15 mA; and (3) the sample powder was dispersed on a zero-background sample holder. The general measurement conditions for XRPD were: Start Angle 3 degrees; Stop Angle 45 degrees; Sampling 0.02 degrees; and Scan speed 2 degree/min.

The XRPD pattern of the phosphate salt of Compound II is shown in FIG. 4 and the XRPD data are provided in Table 3.

TABLE 3

| 2-Theta (°) | Height | H % |
|---|---|---|
| 3.8 | 87 | 21.8 |
| 5.3 | 194 | 48.6 |
| 6.5 | 69 | 17.3 |
| 9.1 | 203 | 50.9 |
| 11.2 | 79 | 19.8 |
| 12.3 | 135 | 33.8 |
| 12.9 | 102 | 25.6 |
| 14.9 | 399 | 100 |
| 15.8 | 394 | 98.7 |
| 17.5 | 194 | 48.6 |
| 19.3 | 290 | 72.7 |
| 21.1 | 98 | 24.6 |
| 21.4 | 111 | 27.8 |
| 22.4 | 163 | 40.9 |
| 23.9 | 68 | 17 |
| 24.4 | 144 | 36.1 |

TABLE 3-continued

| 2-Theta (°) | Height | H % |
|---|---|---|
| 25.6 | 86 | 21.6 |
| 28.3 | 39 | 9.8 |
| 32.7 | 33 | 8.3 |
| 33.9 | 68 | 17 |
| 40.3 | 42 | 10.5 |
| 43.4 | 50 | 12.5 |

Differential Scanning Calorimetry (DSC) Studies for Compound II Phosphate

The phosphate salt of Compound II was characterized by DSC. The DSC was obtained from TA Instruments Differential Scanning calorimetry, Model Q200 with autosampler. The DSC instrument conditions were as follows: 30-350° C. at 10° C./min; Tzero aluminum sample pan and lid; and nitrogen gas flow at 50 mL/min.

The DSC thermogram of Compound II phosphate is shown in FIG. 5. The DSC thermogram revealed a major endothermic event at an onset temperature of 252.6° C. with a peak temperature of 257.2° C. which is believed to be the melting/decomposition of the compound.

Thermogravimetric Analysis (TGA) Studies for Compound II Phosphate

The phosphate salt of Compound II was characterized by TGA. The TGA was obtained from TA Instrument Thermogravimetric Analyzer, Model Q500. The general experimental conditions for TGA were: ramp from 20° C. to 600° C. at 20° C./min; nitrogen purge, gas flow at 40 mL/min followed by balance of the purge flow; sample purge flow at 60 mL/min; platinum sample pan.

The TGA thermogram of Compound II phosphate is shown in FIG. 6. A weight loss of about 1.8% up to 200° C. was observed and believed to be associated with the loss of moisture or residual solvents. Significant weight loss above 230° C. was observed and believed to be associated with the decomposition of the compound.

Example 10. Solid State Characterization of Compound II Maleate

X-Ray Powder Diffraction (XRPD) Studies for Compound II Maleate

The maleate salt of Compound II was characterized by XRPD. The XRPD was obtained from Rigaku MiniFlex X-ray Powder Diffractometer (XRPD). The general experimental procedures for XRPD were: (1) X-ray radiation from copper at 1.054056 Å with $K_\beta$, filter; (2) X-ray power at 30 KV, 15 mA; and (3) the sample powder was dispersed on a zero-background sample holder. The general measurement conditions for XRPD were: Start Angle 3 degrees; Stop Angle 45 degrees; Sampling 0.02 degrees; and Scan speed 2 degree/min.

The XRPD pattern of the maleate salt of Compound II is shown in FIG. 7 and the XRPD data are provided in Table 4.

TABLE 4

| 2-Theta (°) | Height | H % |
|---|---|---|
| 4.5 | 366 | 19.9 |
| 6.5 | 836 | 45.4 |
| 8.9 | 185 | 10 |
| 10.1 | 339 | 18.4 |
| 10.5 | 30 | 1.6 |
| 13.3 | 214 | 11.6 |
| 14.1 | 505 | 27.4 |
| 14.9 | 49 | 2.7 |
| 16.3 | 73 | 4 |
| 16.7 | 77 | 4.2 |
| 17.6 | 40 | 2.2 |
| 18.3 | 61 | 3.3 |
| 19.9 | 86 | 4.7 |
| 21.6 | 109 | 5.9 |
| 22.0 | 288 | 15.6 |
| 24.0 | 607 | 32.9 |
| 27.5 | 87 | 4.7 |
| 28.2 | 1843 | 100 |

Differential Scanning Calorimetry (DSC) Studies for Compound II Maleate

The maleate salt of Compound II was characterized by DSC. The DSC was obtained from TA Instruments Differential Scanning calorimetry, Model Q200 with autosampler. The DSC instrument conditions were as follows: 30-300° C. at 10° C./min; Tzero aluminum sample pan and lid; and nitrogen gas flow at 50 mL/min.

The DSC thermogram of Compound II maleate is shown in FIG. 8. The DSC thermogram revealed two major endothermic events with the first one at an onset temperature of 183.4° C. and a peak temperature of 194.8° C. followed by a second event at an onset temperature of 233.4° C. and a peak temperature of 239.7° C.

Thermogravimetric Analysis (TGA) Studies for Compound II Maleate

The maleate salt of Compound II was characterized by TGA. The TGA was obtained from TA Instrument Thermogravimetric Analyzer, Model Q500. The general experimental conditions for TGA were: ramp from 20° C. to 600° C. at 20° C./min; nitrogen purge, gas flow at 40 mL/min followed by balance of the purge flow; sample purge flow at 60 mL/min; platinum sample pan.

The TGA thermogram of Compound II maleate is shown in FIG. 9. A weight loss of about 1.8% up to 125° C. was observed and believed to be associated with the loss of moisture or residual solvents. Significant weight loss above 175° C. was observed and believed to be associated with the decomposition of the compound.

Example 11. Solid State Characterization of Compound II Hemi-Sulfate

X-Ray Powder Diffraction (XRPD) Studies for Compound II Hemi-Sulfate

The hemi-sulfate salt of Compound II was characterized by XRPD. The XRPD was obtained from Rigaku MiniFlex X-ray Powder Diffractometer (XRPD). The general experimental procedures for XRPD were: (1) X-ray radiation from copper at 1.054056 Å with $K_\beta$ filter; (2) X-ray power at 30 KV, 15 mA; and (3) the sample powder was dispersed on a zero-background sample holder. The general measurement conditions for XRPD were: Start Angle 3 degrees; Stop Angle 45 degrees; Sampling 0.02 degrees; and Scan speed 2 degree/min. The XRPD pattern of the hemi-sulfate salt of Compound II is shown in FIG. 10 and the XRPD data are provided in Table 5.

TABLE 5

| 2-Theta (°) | Height | H % |
|---|---|---|
| 5.3 | 348 | 100 |
| 8.5 | 335 | 96.3 |
| 10.4 | 78 | 22.4 |
| 13.0 | 51 | 14.7 |
| 13.4 | 73 | 21 |
| 15.3 | 128 | 36.8 |
| 16.4 | 50 | 14.4 |
| 18.6 | 65 | 18.7 |
| 19.0 | 48 | 13.8 |
| 20.1 | 90 | 25.9 |
| 21.2 | 41 | 11.8 |
| 21.9 | 67 | 19.3 |
| 22.9 | 50 | 14.4 |
| 23.4 | 51 | 14.7 |
| 24.9 | 89 | 25.6 |
| 26.7 | 41 | 11.8 |

Differential Scanning Calorimetry (DSC) Studies for Compound II Hemi-Sulfate

The hemi-sulfate salt of Compound II was characterized by DSC. The DSC was obtained from TA Instruments Differential Scanning calorimetry, Model Q200 with autosampler. The DSC instrument conditions were as follows: 30-350° C. at 10° C./min; Tzero aluminum sample pan and lid; and nitrogen gas flow at 50 mL/min.

The DSC thermogram of Compound II hemi-sulfate is shown in FIG. 11. The DSC thermogram revealed a major endothermic event at an onset temperature of 283.8° C. with a peak temperature of 289.4° C. which is believed to be the melting/decomposition of the compound.

Thermogravimetric Analysis (TGA) Studies for Compound II Hemi-Sulfate

The hemi-sulfate salt of Compound II was characterized by TGA. The TGA was obtained from TA Instrument Thermogravimetric Analyzer, Model Q500. The general experimental conditions for TGA were: ramp from 20° C. to 600° C. at 20° C./min; nitrogen purge, gas flow at 40 mL/min followed by balance of the purge flow; sample purge flow at 60 mL/min; platinum sample pan.

The TGA thermogram of Compound II hemi-sulfate is shown in FIG. 12. A weight loss of about 1.5% up to 100° C. was observed and believed to be associated with the loss of moisture or residual solvents. Significant weight loss above 200° C. was observed in multiple steps and believed to be associated with the decomposition of the compound.

Example 12. Solid State Characterization of Compound II Hydrochloride

X-Ray Powder Diffraction (XRPD) Studies for Compound II Hydrochloride

The hydrochloride salt of Compound II was characterized by XRPD. The XRPD was obtained from Rigaku MiniFlex X-ray Powder Diffractometer (XRPD). The general experimental procedures for XRPD were: (1) X-ray radiation from copper at 1.054056 Å with $K_\beta$ filter; (2) X-ray power at 30 KV, 15 mA; and (3) the sample powder was dispersed on a zero-background sample holder. The general measurement conditions for XRPD were: Start Angle 3 degrees; Stop Angle 45 degrees; Sampling 0.02 degrees; and Scan speed 2 degree/min.

The XRPD pattern of the hydrochloride salt of Compound II is shown in FIG. 13 and the XRPD data are provided in Table 6.

TABLE 6

| 2-Theta (°) | Height | H % |
|---|---|---|
| 4.4 | 56 | 11.2 |
| 6.5 | 502 | 100 |
| 9.7 | 141 | 28.1 |
| 10.3 | 99 | 19.7 |
| 13.1 | 37 | 7.4 |
| 13.9 | 78 | 15.5 |
| 14.9 | 96 | 19.1 |
| 16.5 | 84 | 16.7 |
| 17.0 | 40 | 8 |
| 18.9 | 83 | 16.5 |
| 19.7 | 73 | 14.5 |
| 20.9 | 54 | 10.8 |
| 21.5 | 169 | 33.7 |
| 21.8 | 114 | 22.7 |
| 23.9 | 130 | 25.9 |
| 25.1 | 37 | 7.4 |
| 25.7 | 38 | 7.6 |
| 27.4 | 50 | 10 |
| 29.1 | 44 | 8.8 |

Differential Scanning Calorimetry (DSC) Studies for Compound II Hydrochloride

The hydrochloride salt of Compound II was characterized by DSC. The DSC was obtained from TA Instruments Differential Scanning calorimetry, Model Q200 with autosampler. The DSC instrument conditions were as follows: 30-300° C. at 10° C./min; Tzero aluminum sample pan and lid; and nitrogen gas flow at 50 mL/min.

The DSC thermogram of Compound II hydrochloride is shown in FIG. 14. The DSC thermogram revealed a major endothermic event at an onset temperature of 183.5° C. with a peak temperature of 190.0° C. which is believed to be the melting/decomposition of the compound.

Thermogravimetric Analysis (TGA) Studies for Compound II Hydrochloride

The hydrochloride salt of Compound II was characterized by TGA. The TGA was obtained from TA Instrument Thermogravimetric Analyzer, Model Q500. The general experimental conditions for TGA were: ramp from 20° C. to 600° C. at 20° C./min; nitrogen purge, gas flow at 40 mL/min followed by balance of the purge flow; sample purge flow at 60 mL/min; platinum sample pan.

The TGA thermogram of Compound II hydrochloride is shown in FIG. 15. A weight loss of about 5.9% up to 200° C. was observed and believed to be associated with the loss of moisture or residual solvents. Significant weight loss above 200° C. was observed and believed to be associated with the decomposition of the compound.

Example 13. Solid State Characterization of Compound II Salicylate

X-Ray Powder Diffraction (XRPD) Studies for Compound II Salicylate

The salicylate salt of Compound II was characterized by XRPD. The XRPD was obtained from Rigaku MiniFlex X-ray Powder Diffractometer (XRPD). The general experimental procedures for XRPD were: (1) X-ray radiation from copper at 1.054056 Å with $K_\beta$ filter; (2) X-ray power at 30 KV, 15 mA; and (3) the sample powder was dispersed on a zero-background sample holder. The general measurement conditions for XRPD were: Start Angle 3 degrees; Stop Angle 45 degrees; Sampling 0.02 degrees; and Scan speed 2 degree/min.

The XRPD pattern of the salicylate salt of Compound II is shown in FIG. 16 and the XRPD data are provided in Table 7.

TABLE 7

| 2-Theta (°) | Height | H % |
|---|---|---|
| 7.3 | 1345 | 100 |
| 10.1 | 111 | 8.3 |
| 11.8 | 80 | 5.9 |
| 12.2 | 91 | 6.8 |
| 13.3 | 300 | 22.3 |
| 14.4 | 514 | 38.2 |
| 15.1 | 370 | 27.5 |
| 15.7 | 382 | 28.4 |
| 17.6 | 135 | 10 |
| 18.3 | 55 | 4.1 |
| 18.9 | 222 | 16.5 |
| 19.9 | 492 | 36.6 |
| 21.9 | 444 | 33 |
| 22.7 | 289 | 21.5 |
| 23.6 | 220 | 16.4 |
| 24.2 | 63 | 4.7 |
| 25.3 | 325 | 24.2 |
| 25.9 | 139 | 10.3 |
| 27.3 | 133 | 9.9 |
| 28.5 | 96 | 7.1 |
| 29.9 | 128 | 9.5 |
| 31.9 | 78 | 5.8 |
| 32.5 | 79 | 5.9 |
| 34.4 | 56 | 4.2 |
| 35.6 | 61 | 4.5 |

Differential Scanning Calorimetry (DSC) Studies for Compound II Salicylate

The salicylate salt of Compound II was characterized by DSC. The DSC was obtained from TA Instruments Differential Scanning calorimetry, Model Q200 with autosampler. The DSC instrument conditions were as follows: 30-300° C. at 10° C./min; Tzero aluminum sample pan and lid; and nitrogen gas flow at 50 mL/min.

The DSC thermogram of Compound II salicylate is shown in FIG. 17. The DSC thermogram revealed 3 major endothermic events: the first one at an onset temperature of 176.0° C. with a peak temperature of 181.7° C., the second one at an onset temperature of 209.9° C. with a peak temperature of 224.9° C., and the third one at an onset temperature of 254.7° C. with a peak temperature of 264.5° C.

Thermogravimetric Analysis (TGA) Studies for Compound II Salicylate

The salicylate salt of Compound II was characterized by TGA The TGA was obtained from TA Instrument Thermogravimetric Analyzer, Model Q500. The general experimental conditions for TGA were: ramp from 20° C. to 600° C. at 20° C./min; nitrogen purge, gas flow at 40 mL/min followed by balance of the purge flow; sample purge flow at 60 mL/min; platinum sample pan.

The TGA thermogram of Compound II salicylate is shown in FIG. 18. A weight loss of about 8.1% up to 250° C. was observed in the first step. Significant weight loss above 300° C. was observed and believed to be associated with the decomposition of the compound.

Example 14. Solid State Characterization of Compound II Mesylate

X-Ray Powder Diffraction (XRPD) Studies for Compound II Mesylate

The mesylate salt of Compound II was characterized by XRPD. The XRPD was obtained from Rigaku MiniFlex X-ray Powder Diffractometer (XRPD). The general experimental procedures for XRPD were: (1) X-ray radiation from copper at 1.054056 Å with $K_\beta$ filter; (2) X-ray power at 30 KV, 15 mA; and (3) the sample powder was dispersed on a zero-background sample holder. The general measurement conditions for XRPD were: Start Angle 3 degrees; Stop Angle 45 degrees; Sampling 0.02 degrees; and Scan speed 2 degree/min.

The XRPD pattern of the mesylate salt of Compound II is shown in FIG. 19 and the XRPD data are provided in Table 8.

TABLE 8

| 2-Theta (°) | Height | H % |
|---|---|---|
| 5.0 | 106 | 23.7 |
| 8.2 | 447 | 100 |
| 13.2 | 76 | 17 |
| 16.9 | 141 | 31.5 |

Differential Scanning Calorimetry (DSC) Studies for Compound II Mesylate

The mesylate salt of Compound II was characterized by DSC. The DSC was obtained from TA Instruments Differential Scanning calorimetry, Model Q200 with autosampler. The DSC instrument conditions were as follows: 30-300° C. at 10° C./min; Tzero aluminum sample pan and lid; and nitrogen gas flow at 50 mL/min.

The DSC thermogram of Compound II mesylate is shown in FIG. 20. The DSC thermogram revealed a major endothermic event at an onset temperature of 166.3° C. with a peak temperature of 174.8° C. which is believed to be the melting/decomposition of the compound.

Thermogravimetric Analysis (TGA) Studies for Compound II Mesylate

The mesylate salt of Compound II was characterized by TGA. The TGA was obtained from TA Instrument Thermogravimetric Analyzer, Model Q500. The general experimental conditions for TGA were: ramp from 20° C. to 600° C. at 20° C./min; nitrogen purge, gas flow at 40 mL/min followed by balance of the purge flow; sample purge flow at 60 mL/min; platinum sample pan.

The TGA thermogram of Compound II mesylate is shown in FIG. 21. A weight loss of about 2.3% up to 100° C. was observed and believed to be associated with the loss of moisture or residual solvents. Significant weight loss above 200° C. was observed and believed to be associated with the decomposition of the compound.

Example 15. Solid State Characterization of Compound II Esylate

X-Ray Powder Diffraction (XRPD) Studies for Compound II Esylate

The esylate salt of Compound II was characterized by XRPD. The XRPD was obtained from Rigaku MiniFlex X-ray Powder Diffractometer (XRPD). The general experimental procedures for XRPD were: (1) X-ray radiation from copper at 1.054056 Å with $K_\beta$ filter; (2) X-ray power at 30 KV, 15 mA; and (3) the sample powder was dispersed on a zero-background sample holder. The general measurement conditions for XRPD were: Start Angle 3 degrees; Stop Angle 45 degrees; Sampling 0.02 degrees; and Scan speed 2 degree/min.

The XRPD pattern of the esylate salt of Compound II is shown in FIG. 22 and the XRPD data are provided in Table 9.

TABLE 9

| 2-Theta (°) | Height | H % |
|---|---|---|
| 4.9 | 168 | 12.1 |
| 7.6 | 1386 | 100 |
| 12.5 | 49 | 3.5 |
| 15.4 | 453 | 32.7 |
| 16.8 | 59 | 4.3 |
| 17.5 | 94 | 6.8 |
| 23.4 | 48 | 3.5 |

Differential Scanning calorimetry (DSC) Studies for Compound II Esylate

The esylate salt of Compound II was characterized by DSC. The DSC was obtained from TA Instruments Differential Scanning calorimetry, Model Q200 with autosampler. The DSC instrument conditions were as follows: 30-300° C. at 10° C./min; Tzero aluminum sample pan and lid; and nitrogen gas flow at 50 mL/min.

The DSC thermogram of Compound II esylate is shown in FIG. 23. The DSC thermogram revealed a major endothermic event at an onset temperature of 180.4° C. with a peak temperature of 187.7° C. which is believed to be the melting/decomposition of the compound.

Thermogravimetric Analysis (TGA) Studies for Compound II Esylate

The esylate salt of Compound II was characterized by TGA. The TGA was obtained from TA Instrument Thermogravimetric Analyzer, Model Q500. The general experimental conditions for TGA were: ramp from 20° C. to 600° C. at 20° C./min; nitrogen purge, gas flow at 40 mL/min followed by balance of the purge flow; sample purge flow at 60 mL/min; platinum sample pan.

The TGA thermogram of Compound II esylate is shown in FIG. 24. A weight loss of about 1.6% up to 100° C. was observed and believed to be associated with the loss of moisture or residual solvents. Significant weight loss above 200° C. was observed and believed to be associated with the decomposition of the compound.

Example 16. Preparation of Other Crystalline Forms of N-(4-(4-Amino-7-(1-isobutyrylpiperidin-4-yl)pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide maleate (Compound I Maleic Acid Salt, Forms II-V)

Experimental procedures for the formation of Compound I maleate salt Forms II, III, IV, and V are summarized in Table 10.

TABLE 10

Crystallization procedures for the formation of Compound I Maleate Solid Forms

| Procedure | Solid State Form after drying at 45-46° C. under vacuum for 8 h |
|---|---|
| Approximately 3.5 mL of saturated solution of Compound I maleate salt in chloroform were evaporated under air without stirring at 25 ± 1° C. and the obtained solid was analyzed by XRPD as Form II. XRPD (see Example 17, FIG. 25). | Form II |
| Approximately 4.0 mL of saturated solution of Compound I maleate salt in 1,4-dioxane were evaporated under air without stirring at 25 ± 1° C. and the obtained solid was analyzed by XRPD as Form III. XRPD (see Example 18, FIG. 26), DSC (see Example 18, FIG. 27), and TGA (see Example 18, FIG. 28) | Form III |
| Approximately 10 mL of saturated solution of Compound I maleate salt in n-BuOH were evaporated under air without stirring at 50 ± 1° C. and the obtained solid was analyzed by XRPD as Form IV. XRPD (see Example 19, FIG. 29), DSC (see Example 19, FIG. 30), and TGA (see Example 19, FIG. 31) | Form IV |
| Reverse addition from DCM/Hexane: to 3.0 mL of heptane was added 1 mL of saturated solution of Compound I maleate salt prepared in dichloromethane followed by stirring to give a solid, which was analyzed by XRPD as Form V. XRPD (see Example 20, FIG. 32), DSC (see Example 20, FIG. 33), and TGA (see Example 20, FIG. 34) | Form V |

Example 17. Solid State Characterization of Compound I Maleate Salt, Form II

X-Ray Powder Diffraction (XRPD) of Compound I Maleate Salt, Form II

The X-Ray Powder Diffraction (XRPD) was obtained from Rigaku MiniFlex X-ray Powder Diffractometer (XRPD). The general experimental procedures for XRPD were: (1) X-ray radiation from copper at 1.054056 Å with $K_\beta$ filter; (2) X-ray power at 30 KV, 15 mA; and (3) the sample powder was dispersed on a zero-background sample holder. The general measurement conditions for XRPD were: Start Angle 3 degrees; Stop Angle 45 degrees; Sampling 0.02 degrees; and Scan speed 2 degree/min.

The XRPD pattern of Form II of the maleic acid salt of Compound I is shown in FIG. 25 and the XRPD data are provided in Table 11.

TABLE 11

| 2-Theta (°) | Height | H % |
|---|---|---|
| 3.8 | 500 | 100 |
| 7.8 | 268 | 53.6 |
| 12.3 | 65 | 13 |
| 19.7 | 70 | 14 |
| 23.5 | 128 | 25.6 |
| 26.0 | 90 | 18 |
| 26.7 | 52 | 10.4 |

Example 18. Solid State Characterization of Compound I Maleate Salt, Form III

The X-Ray Powder Diffraction (XRPD) was obtained from Rigaku MiniFlex X-ray Powder Diffractometer (XRPD). The general experimental procedures for XRPD were: (1) X-ray radiation from copper at 1.054056 Å with $K_\beta$ filter; (2) X-ray power at 30 KV, 15 mA; and (3) the sample powder was dispersed on a zero-background sample holder. The general measurement conditions for XRPD were: Start Angle 3 degrees; Stop Angle 45 degrees; Sampling 0.02 degrees; and Scan speed 2 degree/min.

The XRPD pattern of Form III of the maleic acid salt of Compound I is shown in FIG. 26 and the XRPD data are provided in Table 12.

TABLE 12

| 2-Theta (°) | Height | H % |
|---|---|---|
| 3.8 | 719 | 100 |
| 7.7 | 654 | 91 |
| 8.5 | 61 | 8.5 |
| 10.8 | 50 | 7 |
| 11.5 | 44 | 6.1 |
| 12.1 | 320 | 44.5 |
| 13.8 | 84 | 11.7 |
| 14.9 | 57 | 7.9 |
| 15.4 | 88 | 12.2 |
| 16.2 | 57 | 7.9 |
| 16.9 | 93 | 12.9 |
| 18.3 | 75 | 10.4 |
| 18.9 | 335 | 46.6 |
| 19.6 | 60 | 8.3 |
| 20.6 | 196 | 27.3 |
| 21.6 | 71 | 9.9 |
| 23.1 | 192 | 26.7 |
| 25.3 | 139 | 19.3 |
| 25.8 | 162 | 22.5 |
| 29.1 | 58 | 8.1 |
| 30.4 | 42 | 5.8 |
| 37.0 | 39 | 5.4 |

Differential Scanning Calorimetry (DSC) Studies for Compound I Maleic Acid Salt, Form III Form III of the maleic acid salt of Compound I was characterized by DSC. The DSC was obtained from TA Instruments Differential Scanning calorimetry, Model Q200 with autosampler. The DSC instrument conditions were as follows: 30-300° C. at 10° C./min; Tzero aluminum sample pan and lid; and nitrogen gas flow at 50 mL/min.

The DSC thermogram of Compound I maleic acid salt, Form III is shown in FIG. 27. The DSC thermogram revealed two endothermic events: the first with an onset temperature of 143.9° C. with a peak temperature of 165.4° C. and a second with an onset temperature of 186.3 with a peak temperature of 195.4° C.

Thermogravimetric Analysis (TGA) Studies for Compound I Maleic Acid Salt, Form III Form III of the maleic acid salt of Compound I was characterized by TGA. The TGA was obtained from TA Instrument Thermogravimetric Analyzer, Model Q500. The general experimental conditions for TGA were: ramp from 20° C. to 600° C. at 20° C./min; nitrogen purge, gas flow at 40 mL/min followed by balance of the purge flow; sample purge flow at 60 mL/min; platinum sample pan.

The TGA thermogram of the maleic acid salt of Compound I, Form III is shown in FIG. 28.

Example 19. Solid State Characterization of Compound I Maleate Salt, Form IV The X-Ray Powder Diffraction (XRPD) was obtained from Rigaku MiniFlex X-ray Powder Diffractometer (XRPD). The general experimental procedures for XRPD were: (1) X-ray radiation from copper at 1.054056 Å with $K_\beta$ filter; (2) X-ray power at 30 KV, 15 mA; and (3) the sample powder was dispersed on a zero-background sample holder. The general measurement conditions for XRPD were: Start Angle 3 degrees; Stop Angle 45 degrees; Sampling 0.02 degrees; and Scan speed 2 degree/min.

The XRPD pattern of Form IV of the maleic acid salt of Compound I is shown in FIG. 29 and the XRPD data are provided in Table 13.

TABLE 13

| 2-Theta (°) | Height | H % |
|---|---|---|
| 3.9 | 1181 | 100 |
| 4.6 | 276 | 23.4 |
| 6.2 | 109 | 9.2 |
| 7.8 | 699 | 59.2 |
| 8.5 | 81 | 6.9 |
| 9.1 | 237 | 20.1 |
| 10.1 | 31 | 2.6 |
| 11.6 | 61 | 5.2 |
| 12.2 | 96 | 8.1 |
| 13.6 | 106 | 9 |
| 16.1 | 63 | 5.3 |
| 16.6 | 34 | 2.9 |
| 18.2 | 30 | 2.5 |
| 18.7 | 61 | 5.2 |
| 19.3 | 65 | 5.5 |
| 20.2 | 37 | 3.1 |
| 20.5 | 42 | 3.6 |
| 21.8 | 87 | 7.4 |
| 22.8 | 188 | 15.9 |
| 23.3 | 77 | 6.5 |
| 25.6 | 43 | 3.6 |
| 26.8 | 29 | 2.5 |
| 27.4 | 46 | 3.9 |
| 36.8 | 29 | 2.5 |

Differential Scanning Calorimetry (DSC) Studies for Compound I Maleic Acid Salt, Form IV Form IV of the maleic acid salt of Compound I was characterized by DSC. The DSC was obtained from TA Instruments Differential Scanning calorimetry, Model Q200 with autosampler. The DSC instrument conditions were as follows: 30-300° C. at 10° C./min; Tzero aluminum sample pan and lid; and nitrogen gas flow at 50 mL/min.

The DSC thermogram of Compound I maleic acid salt, Form IV is shown in FIG. 30. The DSC thermogram revealed two endothermic events: the first with an onset temperature of 145.7° C. with a peak temperature of 152.1° C. and a second with an onset temperature of 188.3 with a peak temperature of 202.6° C.

Thermogravimetric Analysis (TGA) Studies for Compound I Maleic Acid Salt, Form IV Form IV of the maleic acid salt of Compound I was characterized by TGA. The TGA was obtained from TA Instrument Thermogravimetric Analyzer, Model Q500. The general experimental conditions for TGA were: ramp from 20° C. to 600° C. at 20° C./min; nitrogen purge, gas flow at 40 mL/min followed by balance of the purge flow; sample purge flow at 60 mL/min; platinum sample pan.

The TGA thermogram of the maleic acid salt of Compound I, Form IV is shown in FIG. 31.

Example 20. Solid State Characterization of Compound I Maleate Salt, Form V

The X-Ray Powder Diffraction (XRPD) was obtained from Rigaku MiniFlex X-ray Powder Diffractometer (XRPD). The general experimental procedures for XRPD were: (1) X-ray radiation from copper at 1.054056 Å with $K_\beta$ filter; (2) X-ray power at 30 KV, 15 mA; and (3) the sample powder was dispersed on a zero-background sample holder. The general measurement conditions for XRPD were: Start Angle 3 degrees; Stop Angle 45 degrees; Sampling 0.02 degrees; and Scan speed 2 degree/min.

The XRPD pattern of Form V of the maleic acid salt of Compound I is shown in FIG. 32 and the XRPD data are provided in Table 14.

TABLE 14

| 2-Theta (°) | Height | H % |
|---|---|---|
| 4.1 | 423 | 95.3 |
| 8.3 | 444 | 100 |
| 8.8 | 140 | 31.5 |
| 10.7 | 43 | 9.7 |
| 12.5 | 35 | 7.9 |
| 13.0 | 34 | 7.7 |
| 15.6 | 44 | 9.9 |
| 18.0 | 130 | 29.3 |
| 20.5 | 41 | 9.2 |
| 23.1 | 53 | 11.9 |
| 23.5 | 122 | 27.5 |
| 24.1 | 38 | 8.6 |
| 27.3 | 150 | 33.8 |
| 28.4 | 42 | 9.5 |
| 29.4 | 36 | 8.1 |
| 31.4 | 43 | 9.7 |
| 35.5 | 49 | 11 |

Differential Scanning calorimetry (DSC) Studies for Compound I Maleic Acid Salt, Form V Form V of the maleic acid salt of Compound I was characterized by DSC. The DSC was obtained from TA Instruments Differential Scanning calorimetry, Model Q200 with autosampler. The DSC instrument conditions were as follows: 30-300° C. at 10° C./min; Tzero aluminum sample pan and lid; and nitrogen gas flow at 50 mL/min.

The DSC thermogram of Compound I maleic acid salt, Form V is shown in FIG. 33. The DSC thermogram revealed an endothermic event with an onset temperature of 189.1° C. with a peak temperature of 200.1° C.

Thermogravimetric Analysis (TGA) Studies for Compound I Maleic Acid Salt, Form V Form V of the maleic acid salt of Compound I was characterized by TGA. The TGA was obtained from TA Instrument Thermogravimetric Analyzer, Model Q500. The general experimental conditions for TGA were: ramp from 20° C. to 600° C. at 20° C./min; nitrogen purge, gas flow at 40 mL/min followed by balance of the purge flow; sample purge flow at 60 mL/min; platinum sample pan.

The TGA thermogram of the maleic acid salt of Compound I, Form V is shown in FIG. 34.

Example A

Axl Autophosphorylation Assay

Autophosphorylation of Axl was carried out by incubating the recombinant Axl protein (Life Technologies, PV4275) in buffer containing 50 mM Tris, pH7.5, 0.2 mg/ml Axl, 5 mM ATP, 20 mM $MgCl_2$ and 2 mM DTT at room temperature for 1 hour.

TAM Enzymatic Assay

The kinase assay buffer contained 50 mM HEPES, pH7.5, 10 mM MgCl2, 1 mM EGTA, 0.01% NP-40 and 2 mM DTT. 0.1 ul test compounds dissolved in DMSO were transferred from compound plates to white 384-well assay plates (Greiner LUMITRAC plates). The final concentration of DMSO was 1.25%. Enzyme solutions of 5.1 nM phosphor-Axl, or 0.0625 nM c-Mer (Carna Biosciences, 08-108), or 0.366 nM Tyro3 (Life Technologies, PR7480A) were prepared in assay buffer. A 1 mM stock solution of peptide substrate Biotin-EQEDEPEGDYFEWLE-amide SEQ ID NO: 1 (Quality Controlled Biochemicals, MA) dissolved in DMSO was diluted to 1 uM in assay buffer containing 2000 uM ATP. 4 ul enzyme solution (or assay buffer for the enzyme blank) was added to the appropriate wells in each plate, and then 4 ul/well substrate solution was added to initiate the reaction. The plate was protected from light and incubated at room temperature for 60 min. The reaction was stopped by adding 4 ul detection solution containing 50 mM Tris-HCl, pH7.8, 150 mM NaCl, 0.05% BSA, 45 mM EDTA, 180 nM SA-APC (Perkin Elmer, CR130-100) and 3 nM Eu-W1024 anti-phosphotyrosine PY20 (Perkin Elmer, AD0067). The plate was incubated for 1 h at room temperature, and HTRF (homogenous time resolved fluorescence) signal was measured on a PHERAstar FS plate reader (BMG labtech). Percentage of inhibition was calculated for each concentration and IC50 value was generated from curve fitting with GraphPad Prism software.

The compounds of Formulae I and II were found to be inhibitors of one or more of AXL, MER, and TYRO3. $IC_{50}$ data for the trifluoroacetic acid salts of the compounds of Formulae I and II are disclosed in U.S. application Ser. No. 15/469,975 and are provided below in Table 15. The symbol "†" indicates an $IC_{50}$ of ≤5 nM, "††" indicates an $IC_{50}$ of >5 nM but ≤10 nM. and "†††" indicates an $IC_{50}$ of >10 nM but ≤100 nM.

TABLE 15

| Compound | Axl $IC_{50}$ (nM) | Mer $IC_{50}$ (nM) | Tyro3 $IC_{50}$ (nM) |
|---|---|---|---|
| Compound I trifluoroacetic acid salt | † | † | ††† |
| Compound I maleic acid salt | † | † | ††† |
| Compound II trifluoroacetic acid salt | † | † | ††† |
| Compound II hemi-sulfuric acid salt | † | † | ††† |

Example B. Generation of BAF3-AXL, BAF3-MER and BAF3-TYRO3 Cells and Cell Proliferation Assay The cytoplasmic domain of AXL, MER, or TYRO3 fused with dimerization sequence and HA tag is cloned into pMSCV vector with puromycin-resistance marker to generate three constructs (pMSCV-AXL, pMSCV-MER and pMSCV-TYRO3). BAF3 cells are transfected with the three constructs individually by electroporation. Single clones that are IL3 independent and puromycin-resistant are selected and characterized. Cells with stable expression of AXL, MER, or TYRO3 are selected and designated BAF3-AXL, BAF3-MER and BAF3-TYRO3 cells.

BAF3, BAF3-AXL, BAF3-MER or BAF3-TYRO3 cells lines are maintained in RPMI1640 with 10% FBS (Gibco/Life Technologies, Carlsbad, Calif.). To measure the effect of test compounds on cell viability, 1000 cells/well are plated into 384 well tissue culture plates in growth medium with a serial dilution of compound or DMSO alone for 48 hours at 37° C. with 5% $CO_2$, cell viability is measured by ATP assay (CellTiter-Glo Assay, Promega) according to the manufacturer's procedure. The data are converted to percent inhibition relative to DMSO control and $IC_{50}$ curves are fitted using GraphPad Prism software.

Example C. BaF3-AXL ELISA and BaF3-MER ELISA

BaF3-AXL or BaF3-MER cells are maintained in culture medium RPMI with 10% FBS and puromycin (1 μg/ml, Gibco/Life Technologies, Carlsbad, Calif.). To measure the effect of test compounds on phosphor-AXL or phosphor-MER, the cells are plated ($5\times10^4$ cells/well) in a V-bottom polypropylene plate (Greiner bio-one) in the presence or absence of test compounds diluted in culture medium, and incubated for 1 hour at 37° C. with 5% $CO_2$. The cells are harvested by centrifugation, and lysed in 110 μl of ice cold lysis buffer (Cell Signaling) with protease and phosphatase inhibitors (Halts PI, Thermo Fisher) for 30 min on ice. The cell lysate is stored at −80° C. for ELISA. ELISA plates are prepared by incubating Costar plate with anti-HA antibody (1 μg/ml) for 1 hour at room temperature. The plates are washed and blocked with PBS with 3% BSA. Cell lysate are loaded onto ELISA plate and incubated at 4° C. overnight. The plates are washed and incubated with LANCE Eu-W1024 anti-phospho-tyrosine antibody (PY-20) (Perkin Elmer) in DELFIA assay buffer (Perkin Elmer) for 1 hour, and read on the Pherastar (BMG Labtech). The data is converted to percent inhibition relative to DMSO control and $IC_{50}$ determination is performed by fitting the curve of percent inhibition versus the log of the inhibitor concentration using GraphPad Prism.

Example D. 111299 Phospho-AXL ELISA

H1299 cells (ATCC), human non-small cell lung carcinoma cell line with Axl expression, are maintained in culture medium RPMI with 10% FBS (Gibco/Life Technologies, Carlsbad, Calif.). To measure the effect of test compounds on phosphor-AXL, the cells are plated (30000 cells/well) in 96 well tissue culture plates (Costar) and incubated overnight at 37° C. with 5% $CO_2$. Compounds at an appropriate concentration are added and incubated for 1 hour at 37° C. with 5% $CO_2$. rhGas6 (R&D Systems, 6 μg/ml) are added to each well. Plates are incubated at 37° C. with 5% $CO_2$ for 15 min. Cells are harvested and lysed in 110 μL of ice cold lysis buffer (Cell Signaling) with protease and phosphatase inhibitors (Halts PI, Thermo Fisher). The lysate is incubated for 1 hour on ice and stored at −80° C. for ELISA. ELISA plates are prepared by incubating Costar plate with anti-HA antibody (1 µg/ml) for 1 hour at room temperature. The plates are washed and blocked with PBS with 3% BSA. Cell lysate is loaded onto ELISA plates and incubated at 4° C. overnight. The plates are washed and incubated with LANCE Eu-W1024 anti-phospho-tyrosine antibody (PY-20) (Perkin Elmer) in DELFIA assay buffer (Perkin Elmer) for 1 hour, and read on the Pherastar (BMG Labtech). The data is converted to percent inhibition relative to DMSO control and $IC_{50}$ determination is performed by fitting the curve of percent inhibition versus the log of the inhibitor concentration using GraphPad Prism.

Example E. Whole Blood 111299 Phospho-AXL ELISA

H1299 Cells (ATCC) are maintained in culture medium RPMI with 10% FBS (Gibco/Life Technologies, Carlsbad, Calif.). To measure the effect of test compounds on phospho-AXL in whole blood, the cells are plated (30000 cells/well) in 96 well tissue culture plates (Costar) and incubated overnight at 37° C. with 5% $CO_2$. Blood obtained from normal donors is mixed with test compounds for 1 hour. Culture medium is removed from H1299 cells, and blood with compound is added to each well. After 1 hour incubation at 37° C. with 5% $CO_2$, rh-Gas6 (4 µg/ml, R&D Systems) is added to each well. The plate is incubated at 37° C. with 5% $CO_2$ for 15 min. The cells are washed with PBS, and lysed in 110 uL of ice cold lysis buffer (Cell Signaling) with protease and phosphatase inhibitors (Halts PI, Thermo Fisher) for 1 hour on ice. The plate is stored at −80° C. for ELISA. ELISA plates are prepared by incubating Costar plate with anti-HA antibody (1 ug/ml) for 1 hour at room temperature. The plates are washed and blocked with PBS with 3% BSA. Cell lysate are loaded onto ELISA plate and incubated at 4° C. overnight. The plates are washed and incubated with LANCE Eu-W1024 anti-phospho-tyrosine antibody (PY-20) (Perkin Elmer) in DELFIA assay buffer (Perkin Elmer) for 1 hour, and read on the Pherastar (BMG Labtech). The data is converted to percent inhibition relative to DMSO control and $IC_{50}$ determination is performed by fitting the curve of percent inhibition versus the log of the inhibitor concentration using GraphPad Prism.

Example F. G361 Phospho-Akt Cell Insight ELISA

G361 cells (ATCC), human malignant melanoma cell line expressing Mer, are maintained in culture medium RPMI with 10% FBS (Gibco/Life Technologies, Carlsbad, Calif.). To measure the effect of test compounds on MER signaling pathway, the cells are plated at $2 \times 10^4$ cells/well in 100 µL volume in 96 well CellBind surface plates (Corning), and incubated overnight at 37° C. with 5% $CO_2$. 20 µL of test compounds at appropriate concentrations are added to the cells and incubated for 1 hour. rhGas6 (4 µg/ml, R&D Systems) is added to each well, and incubated for 20 min. The cells are fixed by adding 50 uL 4% paraformaldehyde (Electron Microscopy Sciences) in PBS (Corning) for 30 min at room temperature. Plates are washed and incubated with 50 uL 0.2% triton X-100 (Sigma) in PBS for 10 minutes at room temperature. Plates are washed and incubated with 100 uL blocking buffer (0.1% BSA in PBS) for 30 min. Plates are washed and incubated with Phospho-AKT (Ser473) (D9E) rabbit mAb (Cell Signaling) diluted in 0.1% BSA (1:300 dilution) at 4° C. overnight. Plates are washed and incubated with 50 uL Alexaflour 488 F(ab')$^2$ fragment of goat anti-rabbit IgG (H+L) (Molecular Probes, 1:1000 dilution) and Hoechst 33342 (Thermo Fisher, 1:2000 dilution) in PBS at room temperature for 2 hours. Plates are washed with PBS, and read on Cell Insight CX5 (Thermo Fisher).

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A process of preparing a salt which is N-(4-(4-Amino-7-(1-isobutyrylpiperidin-4-yl)pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide maleic acid salt, comprising reacting a compound of Formula I:

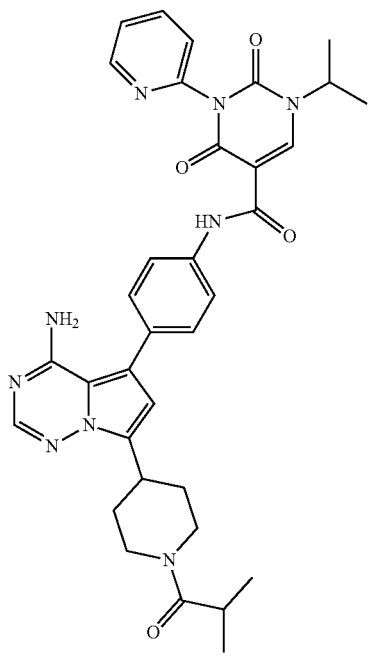

with maleic acid to form said salt.

2. The process of claim 1, wherein about 1 equivalent of maleic acid is used based on 1 equivalent of the compound of Formula I.

3. The process of claim 1, wherein said reacting of the compound of Formula I and maleic acid is conducted in the presence of a solvent component.

4. The process of claim 3, wherein said solvent component comprises methanol.

5. The process of claim 3, wherein said solvent component comprises dichloromethane.

6. The process of claim 3, wherein said solvent component comprises methanol and dichloromethane.

7. The process of claim 6, wherein the process further comprises removing a substantial portion of dichloromethane to precipitate said salt.

8. The process of claim 3, wherein said process further comprises, prior to said reacting, forming a solution of the compound of Formula I in a solvent component.

9. The process of claim 8, wherein the solution is formed by heating a slurry of the compound of Formula I in the solvent component to a temperature of from about 45° C. to about 55° C.

10. The process of claim 9, wherein said process further comprises stirring said solution; and filtering said solution to form a filtrate prior to said reacting of the compound of Formula I with maleic acid.

11. The process of claim 10, wherein said process further comprises adding activated carbon and silica gel to the solution after said step of heating said slurry to a temperature of from about 45° C. to about 55° C. to form a solution and before said step of stirring said solution.

12. A process of preparing a salt which is N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide hemi-sulfuric acid salt, comprising reacting a compound of Formula II:

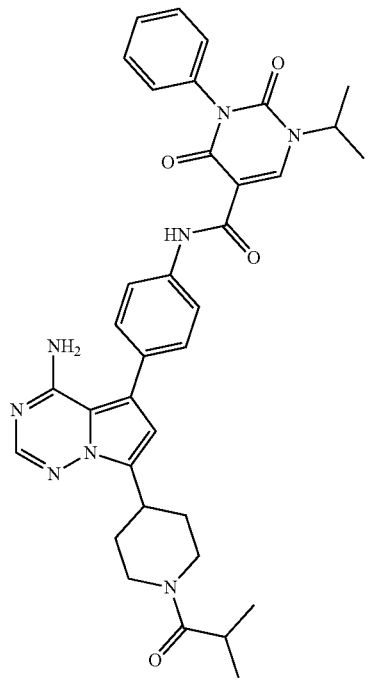

with sulfuric acid to form said salt.

13. The process of claim 12, wherein about 0.6 equivalents of sulfuric acid is used based on 1 equivalent of the compound of Formula II.

14. The process of claim 12, wherein the process comprises:
adding the compound of Formula II to a solvent component form a solution;
adding sulfuric acid to said solution at room temperature;
concentrating the solution to form a slurry;
stirring the slurry at a temperature of from about 60° C. to about 70° C.; and
cooling the slurry to a temperature of from about 15° C. to about 25° C. to precipitate said salt.

15. The process of claim 14, wherein the solvent component comprises methanol.

16. The process of claim 14, wherein the solvent component comprises dichloromethane.

17. The process of claim 14, wherein the solvent component comprises methanol and dichloromethane.

18. The process of claim 14, wherein the sulfuric acid is about 1M in water.

19. The process of claim 12, wherein the process comprises preparing N-(4-(4-Amino-7-(1-isobutyrylpiperidin-4-yl)pyrrolo [1,2-f][1,2,4]triazin-5-yl)phenyl)-1-isopropyl-2,4-dioxo-3-phenyl-1, 2,3, 4-tetrahydropyrimidine-5-carboxamide sulfuric acid salt.

20. The process of claim 19, wherein process of preparing a salt which is N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide sulfuric acid salt comprising reacting a compound of Formula II with about 1 equivalent of sulfuric acid based on 1 equivalent of the compound of Formula II.

21. The process of claim 19, wherein the process for preparing N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide sulfuric acid salt comprises:

adding the compound of Formula II to a first solvent component at room temperature to form a solution;
heating the solution to a temperature of from about 50° C. to about 60° C.;
adding sulfuric acid to said solution; and
removing solvent to precipitate the sulfuric acid salt.

22. The process of claim 21, wherein the first solvent comprises methanol.

23. The process of claim 21, wherein the sulfuric acid is added as a solution in water.

24. The process of claim 19, further comprising the steps of:

adding the N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide sulfuric acid salt to a second solvent component to form a slurry;
heating the slurry to a temperature of from about 30° C. to about 40° C.;
agitating the slurry; and
collecting the resulting hemi-sulfuric acid salt.

25. The process of claim 24, wherein the second solvent component comprises water.

26. The process of claim 24, further comprising preparing an amorphous form of the hemi-sulfuric acid salt, wherein the preparing an amorphous form of the hemi-sulfuric acid salt comprises the steps of:

adding the hemi-sulfuric acid salt to a third solvent component at room temperature to form a solution;
filtering the solution;
concentrating the filtrate; and
drying the resulting solid resulting in the amorphous hemi-sulfuric acid salt.

27. The process of claim 26, wherein the third solvent component comprises acetone and methanol.

28. The process of claim 1, wherein the salt is crystalline.

29. The process of claim 28, wherein the salt has at least one XRPD peak, in terms of 2-theta, selected from about 4.3°, about 8.4°, about 12.6°, about 13.2°, and about 18.5°.

30. The process of claim 28, wherein the salt has at least two XRPD peaks, in terms of 2-theta, selected from about 4.3°, about 8.4°, about 12.6°, about 13.2°, and about 18.5°.

31. The process of claim 28, wherein the salt has at least three XRPD peaks, in terms of 2-theta, selected from about 4.3°, about 8.4°, about 12.6°, about 13.2°, and about 18.5°.

32. The process of claim 12, wherein the salt is crystalline.

33. The process of claim 32, wherein the salt has at least one XRPD peak, in terms of 2-theta, selected from about 5.3°, about 8.5°, about 15.3°, about 20.1°, and about 24.9°.

34. The process of claim 32, wherein the salt has at least two XRPD peaks, in terms of 2-theta, selected from about 5.3°, about 8.5°, about 15.3°, about 20.1°, and about 24.9°.

35. The process of claim 32, wherein the salt has at least three XRPD peaks, in terms of 2-theta, selected from about 5.3°, about 8.5°, about 15.3°, about 20.1°, and about 24.9°.

* * * * *

SEQUENCE LISTING

```
<160> NUMBER OF SEQ ID NOS: 1

<210> SEQ ID NO 1
<211> LENGTH: 15
<212> TYPE: PRT
<213> ORGANISM: Artificial
<220> FEATURE:
<223> OTHER INFORMATION: synthetic polypeptide

<400> SEQUENCE: 1

Glu Gln Glu Asp Glu Pro Glu Gly Asp Tyr Phe Glu Trp Leu Glu
1               5                   10                  15
```